(12) United States Patent
Wang et al.

(10) Patent No.: US 10,240,163 B2
(45) Date of Patent: Mar. 26, 2019

(54) INCREASING THE CONTENT OF LONG CHAIN FATTY ACIDS IN SEED OIL

(71) Applicants: Donald Danforth Plant Science Center, St. Louis, MO (US); The Curators of the University of Missouri, Columbia, MO (US)

(72) Inventors: Xuemin Wang, St. Louis, MO (US); Maoyin Li, St. Louis, MO (US)

(73) Assignees: Donald Danforth Plant Science Center, St. Louis, MO (US); The Curators of the University of Missouri, Columbia, MO (US)

( * ) Notice: Subject to any disclaimer, the term of this patent is extended or adjusted under 35 U.S.C. 154(b) by 312 days.

(21) Appl. No.: 14/866,125

(22) Filed: Sep. 25, 2015

(65) Prior Publication Data
US 2016/0083741 A1    Mar. 24, 2016

Related U.S. Application Data

(63) Continuation of application No. PCT/US2014/032009, filed on Mar. 27, 2014.

(60) Provisional application No. 61/805,773, filed on Mar. 27, 2013.

(51) Int. Cl.
| | |
|---|---|
| *C12N 15/82* | (2006.01) |
| *C12N 9/20* | (2006.01) |
| *C07C 69/604* | (2006.01) |
| *C12P 7/64* | (2006.01) |

(52) U.S. Cl.
CPC ........ *C12N 15/8247* (2013.01); *C07C 69/604* (2013.01); *C12N 9/20* (2013.01); *C12P 7/6463* (2013.01); *C12Y 301/01* (2013.01)

(58) Field of Classification Search
None
See application file for complete search history.

(56) References Cited

U.S. PATENT DOCUMENTS 5,750,871 A * 5/1998 Moloney ............ C12N 15/8205
435/252.2
2004/0005604 A1   1/2004 Gramatikova et al.

OTHER PUBLICATIONS

Huang et al, Plant Physiology 125: 573-584, Feb. 2001.*
Bafor et al., "Ricinoleic Acid Biosynthesis and Triacylglycerol Assembly in Microsomal Preparations from Developing Castor-Bean (Ricinus communis) Endosperm", Biochemical Journal, 1991, pp. 507-514, vol. 280.
Bassel et al, "Elucidating the Germination Transcriptional Program Using Small Molecules", Plant Physiology, May 2008, pp. 143-155, vol. 147.
Bates et al., "Acyl Editing and Headgroup Exchange are the Major Mechanisms that Direct Polyunsaturated Fatty Acid Flux into Triacylglycerols", Plant Physiology, Nov. 2012, pp. 1530-1539, vol. 160.
Bates et al., "Analysis of Acyl Fluxes Through Multiple Pathways of Triacylglycerol Synthesis in Developing Soybeans Embryos", Plant Physiology, May 2009, pp. 55-72, vol. 150.
Bates et al., "Incorporation of Newly Synthesized Fatty Acids into Cytosolic Glycerolipids in Pea Leaves Occurs via Editing", The Journal of Biological Chemistry, Oct. 26, 2007, pp. 31206-31216, vol. 282, No. 43.
Bates et al., "The Pathway of Triacylglycerol Synthesis Through Phosphatidylcholine in Arabidopsis Produces a Bottleneck for the Accumulation of Unusual Fatty Acids in Transgenic Seeds", The Plant Journal, 2011, pp. 387-399, vol. 68.
Bates et al., "The Significance of Different Diacyglycerol Synthesis Pathways on Plant Oil Composition and Bioengineering", Frontiers in Plant Science, Jul. 2012, pp. 1-11, vol. 3, Article 147.
Bourgis et al., "Comparative Transcriptome and Metabolite Analysis of Oil Palm and Date Palm Mesocarp that Differ Dramatically in Carbon Partitioning", Proceedings of the National Academy of Sciences, Jul. 26, 2011, pp. 12527-12532, vol. 108, No. 30.
Chapman et al., "Compartmentation of Triacylglycerol Accumulation in Plants", The Journal of Biological Chemistry, Jan. 20, 2012, pp. 2288-2294, vol. 287, No. 4.
Dyer et al., "High-Value Oils from Plants", The Plant Journal, 2008, pp. 640-655, vol. 54.
Fan et al., "Subcellular Distribution and Tissue Expression of Phospholipase Da, Db, and Dg in *Arabidopsis*", Plant Physiology, Apr. 1999, pp. 1371-1378, vol. 119.
Han et al., Quantitative Analysis and Molecular Species Fingerprinting of Triacylglyceride Molecular Species Directly from Lipid Extracts of Biological Smaples by Electrospray Ionization Tandem Mass Spectrometry, Analytical Biochemistry, 2001, pp. 88-100, vol. 295.
Han et al., "The Cytochrome P450 CYP86A22 Is a Fatty Acyl-CoA w-Hydroxylase Essential for Estolide Synthesis inthe Stigma of Petunia Hybrida", The Journal of Biological Chemistry, Feb. 5, 2010, pp. 3986-3996, vol. 285, No. 6.
Joubés et al., "The VLFCA Elongase Gene Family in *Arabidopsis thaliana*: Phylogenetic Analysis, 3D Modelling and Expression Profiling", Plant Molecular Biology, 2008, pp. 547-566, vol. 66.

(Continued)

*Primary Examiner* — Elizabeth F McElwain
(74) *Attorney, Agent, or Firm* — Thompson Coburn LLP; William A. Holtz

(57) ABSTRACT

Provided are plants that express, or overexpress, a pPLAIIIδ protein. Constitutive or seed-specific expression of pPLAIIIδ protein in *Arabidopsis* increases seed oil content, the amount of C20 and C22 fatty acids, and the amount of C56, C58, and C60 triacylglycerols, effectively resulting in significantly higher oil yield per plant. Use of pPLAIIIδ is therefore an effective biotechnological tool to significantly increase plant yield, including oil, and the amount of high value long chain fatty acids in agricultural and horticultural crops, especially oilseed crops.

9 Claims, 36 Drawing Sheets
Specification includes a Sequence Listing.

(56) References Cited

OTHER PUBLICATIONS

La Camera et al., "A Pathogen-Inducible Patatin-Like Lipid Acyl Hydrolase Facilitates Fungal and Bacterial Host Colonization in *Arabidopsis*", The Plant Journal, 2005, pp. 810-825, vol. 44.

Lee et al., "Enhanced Seed Viability and Lipid Compositional Changes During Natural Ageing by Suppressing Phospholipase Da in Soybean Seed", Plant Biotechnology Journal, 2012, pp. 164-173, vol. 10.

Lee et al., "Phospholipid and Triacylglycerol Profiles Modified by PLD Suppression in Soybean Seed", Plant Biotechnology Journal, 2011, pp. 359-372, vol. 9.

Li et al., "Double Knockouts of Phospholipases Dz1 and Dz2 in *Arabidopsis* Affect Root Elongation During Phosphate-Limited Growth but Do Not Affect Root Hair Patterning", Plant Physiology, Feb. 2006, pp. 761-770, vol. 140.

Li et al., "Patatin-Related Phospholipase pPLAIIIbeta-Induced Changes in Lipid Metabolism Alter Cellulose Content end Cell Elongation in *Arabidopsis*", Plant Cell, Mar. 2011, pp. 1107-1123, vol. 23, No. 3.

Li et al., "Patatin-Related Phospholipase pPLAIIIdelta Increases Seed Oil Content with Long-Chain Fatty Acids in *Arabidopsis*", Plant Physiology, May 2013, pp. 39-51, vol. 162, No. 1.

Li_Beisson et al., "Acyl-Lipid Metabolism", The *Arabidopsis* Book, Jul. 11, 2010, 65 pages.

Loewen et al., "Phospholipid Metabolism Regulated by a Transcription Factor Sensing Phosphatidic Acid", Science Magazine, Jun. 11, 2004, pp. 1644-1647, vol. 304.

Lu et al., "An Enzyme Regulating Triacylglycerol Composition is Encoded by the ROD1 Gene of *Arabidopsis*", Proceedings of the National Academy of Sciences, Nov. 3, 2009, pp. 18837-18842, vol. 106, No. 44.

Magnes et al., "LC/MS/MS Method for Quantitative Determination of Long-Chain Fatty Acyl-CoAs", Analytical Chemistry, May 1, 2005, pp. 2889-2894, vol. 77.

Murakami et al., "Recent Progress in Phospholipase A2 Research: From Cells to Animals to Humans", Progress in Lipid Research, 2011, pp. 152-192, vol. 50.

Pappan et al., "Evidence for and Characterization of Ca2+ Binding to the Catalytic Region of *Arabidopsis thaliana* Phospholipase Db*", The Journal of Biological Chemistry, Nov. 12, 2004, pp. 47833-47839, vol. 279, No. 46.

Pidkowich et al., "Modulating Seed b-ketoacyl-acyl Carrier Protein Synthase II Level Converts the Composition of a Temperate Seed Oil to that of a Plam-Like Tropical Oil", Proceedings of the National Academy of Sciences, Mar. 13, 2007, pp. 4742-4747, vol. 104, No. 11.

Rietz et al., "Expression of the Patatin-Related Phospholipase A Gene AtPLA IIA in *Arabidopsis thaliana* is Up-Regulated by Salicylic Acid, Wounding, Ethylene, and Iron and Phosphate Deficiency", Planta, 2004, pp. 743-753, vol. 219.

Rietz et al., "Roles of *Arabidopsis patatin*-Related Phospholipases A in Root Development Are Related to Auxin Responses and Phosphate Deficiency", Molecular Plant, May 2010, pp. 524-538, vol. 3, No. 3.

Rogalski et al., "Engineering Plastid Fatty Acid Biosynthesis to Improve Food Quality and Biofuel Production in Higher Plants", Plant Biotechnology Journal, 2011, pp. 554-564, vol. 9.

Scherer et al., "Patatin-Related Phospholipase: A Nomenclature, Subfamilies and Functions in Plants", Trends in Plant Science, Dec. 2010, pp. 693-700, vol. 15, No. 12.

Stewart et al., "A Rapid CTAB DNA Isolation Technique Useful RAPD Fingerprinting and other PCR Applications", Biotechniques, May 1993, pp. 748-750, vol. 14, No. 5.

Stymne et al., "Evidence for the Reversibility of the acyl-CoA : Lysophosphatidylcholine Acyltransferase in Microsomal Preparations from Developing Safflower (*Carthamus tinctorius* L.) Cotyledons and Rat Liver", Biochemical Journal, 1984, pp. 305-314, vol. 223.

Tamura et al., "MEGA5: Molecular Evolutionary Genetics Analysis Using Maximum Likelihood, Evolutionary Distance, and Maximum Parsimony Methods", Molecular Biology and Evolution, 2011, pp. 27031-2739, vol. 28, No. 10.

Tjellström et al., "Rapid Kinetic Labeling of *Arabidopsis* Cell Suspension Cultures: Implications for Models of Lipid Export form Plastids", Plant Physiology, Feb. 2012, pp. 601-611, vol. 158.

Wang et al., "Chloroplast Lipid Synthesis and Lipid Trafficking Through ER-Plastid Membrane Contact Sites", Biochemical Society Transactions, 2012, pp. 457-463, vol. 40.

Wang et al., "Metabolic Interactions Between the Lands Cycle and the Kennedy Pathway of Glycerolipid Synthesis in *Arabidopsis* Developing Seeds", The Plant Cell, Nov. 2012, pp. 4652-4669, vol. 24.

Wang et al., "TGD4 Involved in Endoplasmic Reticulum-to-Chloroplast Lipid Trafficking is a Phosphatidic Acid Binding Protein", The Plant Journal, 2012, pp. 614-623, vol. 70.

Welti et al., "Profiling Membrane Lipids in Plant Stress Responses: Role of Phospholipase Da in Freezing-Induced Lipid Changes in *Arabidopsis*", The Journal of Biological Chemistry, Aug. 30, 2002, pp. 31994-32002, vol. 277, No. 35.

Weselake et al., "Increasing the Flow of Carbon into Seed Oil", Biotechnology Advances, 2009, pp. 866-878, vol. 27.

Winter et al., "An "Electronic Fluorescent Pictograph" Browser for Exploring and Analyzing Large-Scale Biological Data Sets", PLoS One, Aug. 2007, pp. e718, Issue 8, 12 pages.

Xiao et al., "Overexpression of *Arabidopsis* Acyl-CoA Binding Protein ACBP3 Promotes Starvation-Induced and Age-Dependent Leaf Senescence", The Plant Cell, May 2010, pp. 1463-1482, vol. 22.

Yang et al., "AtPLAI Is an Acyl Hydrolase Involved in Basal Jasmonic Acid Production and *Arabidopsis* Resistance to Botrytis Cinerea", The Journal of Biological Chemistry, Jun. 22, 2007, pp. 18116-18128, vol. 282, No. 25.

Yang et al., "The Patatin-Containing Phospholipase A pPLAIIa Modulates Oxylipin Formation and Water Loss in *Arabidopsis thaliana*", Molecular Plant, Mar. 2012, pp. 452-460, vol. 5, No. 2.

\* cited by examiner

INCREASING THE CONTENT OF LONG CHAIN FATTY ACIDS IN SEED OIL

CROSS-REFERENCE TO RELATED APPLICATIONS

This application is a Continuation of PCT/US2014/32009, filed Mar. 27, 2014, that claims the benefit of priority of U.S. Provisional Application Ser. No. 61/805,773, filed Mar. 27, 2013, the contents of both of which are herein incorporated by reference in their entireties.

STATEMENT REGARDING FEDERALLY SPONSORED RESEARCH OR DEVELOPMENT

This invention was made with government support under Award # DE-SC0001295 from the U.S. Department of Energy (DOE), Office of Science, Office of Basic Energy Sciences (BES), Materials Sciences and Engineering Division; MCB-0922879 from the National Science Foundation; and 30900787 from the National Natural Science Foundation of China. Instrument acquisition and method development at the Kansas Lipidomics Research Center was supported by grants MCB-0920663, DBI-0521587 from the National Science Foundation, and a Kansas Experimental Program to Stimulate Competitive Research Award EPS-0236913 subaward. The U.S. government has certain rights in the invention.

INCORPORATION OF SEQUENCE LISTING

A sequence listing is contained in the file named "DDPSC0050_401_PC20140326_Substitute_Sequence-Listing.txt" which is 17,927 bytes (measured in MS-Windows) and was created on Apr. 9, 2018. The listing contains SEQ ID NOs: 1 to 58. This electronic sequence listing is electronically filed herewith and is incorporated herein by reference.

BACKGROUND

Field

This disclosure relates to the areas of plant biochemistry and metabolism, and provides biotechnological tools that enable modification of the oil content, fatty acid composition, and triacylglyercol composition of vegetable oils useful for improved nutrition, biofuel, and industrial applications.

Introduction

Lipids play essential structural, metabolic, and regulatory roles in plant growth, development, and stress responses. In addition, plant lipids are a major source of food and renewable materials for various industrial and energy applications (Dyer et al., 2008; Hayden et al., 2011; Rogalski and Carrer, 2011; Bates and Browse, 2012). Substantial progress has been made toward a basic understanding of the biochemical reactions of lipid biosynthesis in plants, but many fundamental questions about lipid metabolism remain unanswered (Weselake et al., 2009; Chapman and Ohlrogge, 2012). Recent results suggest that the metabolism of phosphatidylcholine (PC) plays multiple, important roles in glycerolipid production. An increasing line of research shows that storage lipid triacylglycerols (TAG) are not synthesized primarily via the Kennedy pathway, but are derived from PC through acyl editing (Bates et al., 2009; 2012; Tjellstrom et al., 2012). PC is also hypothesized to be involved in trafficking of fatty acids from the plastid to the endoplasmic reticulum (ER), where glycerolipids, including TAG, are assembled (Wang and Benning, 2012). It is proposed that plastidial fatty acids are transferred to lysophosphatidylcholine (LPC) to form PC, which serves as a substrate for fatty acid desaturation and modification. While the importance of PC metabolism in TAG production is clear, the specific enzymes involved in PC turnover are not well elucidated (Chapman and Ohlrogge, 2012; Bates et al., 2012), and the impact of PC turnover on TAG accumulation remains to be determined.

Phospholipase A (PLA) hydrolyzes PC to produce LPC and a free fatty acid. This reaction has been implicated in various cellular functions, including the production of lipid mediators, carbon partitioning, and cell elongation.

Patatin-containing PLA, pPLA, is a major family of intracellular acyl-hydrolyzing enzymes in plants (Scherer et al., 2010; Murakami et al., 2011). The ten-gene pPLA family in Arabidopsis is grouped into three subfamilies, pPLAI, pPLAII ($\alpha$, $\beta$, $\gamma$, $\delta$, $\epsilon$), and pPLAIII ($\alpha$, $\beta$, $\gamma$, $\delta$). pPLAIII$\delta$ is also known in the literature as Patatin-like protein 9, PLAIIIB, AtPLA-IIIB, PLP9, and STURDY. Sequence AtPLA-IIIB was isolated by Huang et al. (2001), who showed that it is expressed most highly in roots, less in flowers and stems, and least in leaves. No data on expression in seeds were reported.

pPLAI has been shown to contribute to the resistance to Botrytis cinerea, possibly by mediating the basal levels of jasmonate production (Yang et al., 2007), whereas pPLAII$\alpha$ negatively modulates both plant response to bacterial pathogens (La Camera et al., 2005) and oxylipin production (Yang et al., 2012). pPLAII$\beta$ impacts root elongation during phosphate deficiency, and pPLAII$\gamma$ and pPLAII$\delta$ have been implicated in auxin responses (Rietz et al., 2004; 2010).

Activation-tagging of pPLAIII$\delta$ in Arabidopsis resulted in plants exhibiting a stiff infloresecence stem, an increase in cell number in the inflorescence stem, thicker leaves, shorter siliques, larger seeds, round-shaped flowers, and delayed growth, and reduced lodging compared to wild-type plants. No effects on seed oil content or composition were reported. (Huang et al., 2001). Overexpression of pPLAIII$\beta$ in Arabidopsis resulted in decreased cell elongation and stunted growth (Li et al., 2011). These results indicate that the pPLA family plays important, diverse roles in plant growth and stress responses, but their role in seed oil production is not known.

Lin et al. (2011) discloses that Arabidopsis overexpressing Oncidium Patatin-like protein OSAG78 exhibited higher lipase activity than wild-type control, higher free linoleic acid (C18) and linolenic acid (C18) than in wild-type control, altered phenotypes including smaller leaves and rounder flowers, and delayed flowering due to reduced gibberellin synthesis that could be rescued by gibberellin $A_3$.

One enigma from recent genomic analysis of Arabidopsis has been that there are as many genes annotated as being involved in lipid catabolism as there are in lipid synthesis (Li-Beisson et al., 2010). While the functions for many genes involved in lipid biosynthesis have been documented, little is known about the role of lipid-hydrolyzing enzymes in lipid metabolism and oil production. A recent study compared the transcriptomes of mesocarp from oil palm and date palm that accumulate approximately 90% and 1% oil, respectively (Bourgis et al., 2011). The mRNA level of key genes in fatty acid synthesis in oil palm mesocarp is 2 to 44 fold higher than in date palm. The mRNA level of palm pPLAIII$\beta$ is 22 fold higher in oil palm compared to date palm mesocarp (Bourgis et al., 2011), but the role for pPLAIII in oil accumulation remains to be determined. Patatin-related enzymes typically contain a catalytic center with the esterase box GXSXG and other specific motifs including a catalytic dyad motif, which typically contains DGG (Scherer et al., 2010). The pPLAIII subfamily differs from pPLAI and pPLAII in that it does not contain the canonical esterase GXSXG motif, but instead has the sequence GXGXG (Scherer et al., 2010). Recent analysis of pPLAIIIβ shows that pPLAIIIβ hydrolyzes PC to produce LPC and free fatty acids (Li et al., 2011). Moreover, overexpression of pPLAIIIβ increases membrane glycerolipid content in vegetative tissues whereas its gene knockout has the opposite effect.

Triacylglycerol (TAG) is composed of three fatty acyl groups esterified to a glycerol backbone at the sn-1, sn-2 and sn-3 positions. In higher plants, TAG is the predominant component of the oil of the seeds or fruits of oleaginous plants. Seed lipids comprising TAGs are structurally similar to long chain hydrocarbons derived from petroleum. TAGs provide a source of highly reduced carbon for both food and non-food applications, such as supplying feedstocks for the production of petrochemical alternatives. Consequently, plants are excellent renewable resources for the production of high value oleochemicals, including fatty acids, and have the potential to fulfill market needs in a wide range of industrial sectors, including food, health, cosmetics, pharmaceuticals, and the chemical industry. In view of the economic importance of vegetable oils and their expanding use as a renewable feedstock, there is considerable interest in increasing total seed oil yield and optimizing the fatty acid and TAG composition of industrially important oils in high-yield crops. Depending on the use of the oil, different fatty acid compositions are needed, and a major objective for plant breeders and biotechnologists is to customize and optimize the diversity of plant fatty acids to produce oils having desirable fatty acid compositions.

Thus, there is a need for a detailed understanding of fatty acid biosynthesis and TAG assembling pathways in plants and a need in the art for methods that facilitate enhancing the oil content of seeds and modifying the fatty acid and TAG composition of such oil for use in a variety of different industrial applications.

SUMMARY OF THE DISCLOSURE

The foregoing observations prompted the present inventors to determine the role of pPLAIIIs in seed oil production. Here they show for the first time that pPLAIIIδ promotes TAG production with increased accumulation of long chain fatty acids in *Arabidopsis* seeds, permitting modification of seed oil content and composition in oilseed crops via transgene technology to increase the proportion of very long chain fatty acids (VLCFAs: C18 and greater).

The polyunsaturated fatty acids (PUFAs) linoleic acid (18:2) and α-linolenic acid (18:3) in triacylglycerols (TAG) are major factors affecting the quality of plant oils for human health, as well as for biofuels and other renewable applications. These PUFAs are essential fatty acids for animals and plants, but also are the source of unhealthy trans fats during the processing of many foodstuffs.

Accordingly, the present disclosure provides useful biotechnological tools for improving the oil content of seeds, especially those of traditional oil seed crops, as well as modifying (improving) the fatty acid profiles of vegetable oils to include higher levels of long chain fatty acids, for both human health and industrial applications.

Therefore, among its many embodiments, the present disclosure includes, in a first set of embodiments, the following:

1. A method of increasing the content of triacylglycerol and 20- and 22-carbon fatty acids in a seed, comprising overexpressing phospholipase pPLAIIIδ in said seed.

2. The method of 1, wherein said pPLAIIIδ is overexpressed in an embryo of said seed.

3. The method of 1 or 2, wherein said overexpression of said pPLAIIIδ increases oil content in said seed.

4. The method of any one of 1-3, wherein said phospholipase pPLAIIIδ is *Arabidopsis* phospholipase pPLAIIIδ.

5. The method of 4, wherein said *Arabidopsis* phospholipase pPLAIIIδ is encoded by the *Arabidopsis* genomic sequence of pPLAIIIδ.

6. The method of 5, wherein said *Arabidopsis* genomic sequence of pPLAIIIδ is obtainable by PCR using Col-0 *Arabidopsis* genomic DNA as a template and primers listed in Table 1.

7. The method of any one of 1-6, wherein expression of said phospholipase pPLAIIIδ is under the control of the 35S cauliflower mosaic virus promoter or a seed-specific promoter.

8. The method of 7, wherein said seed-specific promoter is the soybean β-conglycinin promoter.

9. The method of any one of 1-8, wherein said seed is an *Arabidopsis thaliana* seed.

In a further set of embodiments, the present disclosure includes:

1. A transgenic plant, other than *Arabidopsis*, the genome of which comprises a heterologous nucleotide sequence that encodes a pPLAIIIδ protein, which heterologous nucleotide sequence is expressed or overexpressed.

2. The transgenic plant, other than *Arabidopsis*, of 1, which is an oilseed plant.

3. The transgenic oilseed plant other than *Arabidopsis* of 2, which is selected from the group consisting of:
  (i) a transgenic oilseed plant that produces an enhanced amount of oil in seeds of said plant compared to the amount of oil produced in seeds by an otherwise identical control oilseed plant grown under the same conditions;
  (ii) a transgenic oilseed plant that produces oil in seeds of said plant containing an enhanced amount of C20 and C22 fatty acids compared to the amount of C20 and C22 fatty acids in oil produced in seeds by an otherwise identical control oilseed plant grown under the same conditions;
  (iii) a transgenic oilseed plant that produces oil in seeds of said plant containing an enhanced amount of C56, C58, and C60 triacylglycerols compared to the amount of C56, C58, and C60 triacylglycerols in oil produced in seeds by an otherwise identical control oilseed plant grown under the same conditions;
  (iv) a transgenic oilseed plant that produces an enhanced amount of oil in seeds of said plant containing an enhanced amount of C20 and C22 fatty acids compared to the amount of oil and C20 and C22 fatty acids produced in seeds by an otherwise identical control oilseed plant grown under the same conditions;
  (v) a transgenic oilseed plant that produces an enhanced amount of oil in seeds of said plant containing an enhanced amount of C56, C58, and C60 triacylglycerols compared to the amount of oil and C56, C58, and C60 triacylglycerols produced in seeds by an otherwise identical control oilseed plant grown under the same conditions;

(vi) a transgenic oilseed plant that produces an enhanced amount of oil in seeds of said plant containing an enhanced amount of C20 and C22 fatty acids and an enhanced amount of C56, C58, and C60 triacylglycerols compared to the amount of oil, C20 and C22 fatty acids, and C56, C58, and C60 triacylglycerols, respectively, produced in seeds by an otherwise identical control oilseed plant grown under the same conditions; and (vii) a transgenic oilseed plant that produces enhanced levels of mRNA transcripts for genes in the Kennedy pathway in seeds of said plant compared to the levels of mRNA transcripts for genes in the Kennedy pathway produced in seeds by an otherwise identical control oilseed plant grown under the same conditions.

4. The transgenic oilseed plant of 2 or 3,
wherein said pPLAIIIδ protein has at least 95% sequence similarity to *Arabidopsis* pPLAIIIδ protein comprising the amino acid sequence encoded by *Arabidopsis* Genome Initiative Database Accession At3g63200, and
wherein said pPLAIIIδ protein exhibits enzymatic activity in the range of from about 75% to about 125% or more of the enzymatic activity of said *Arabidopsis* pPLAIIIδ protein.

5. The transgenic oilseed plant of any one of 2-4, wherein said pPLAIIIδ protein comprises the amino acid sequence encoded by *Arabidopsis* Genome Initiative Database Accession At3g63200.

6. The transgenic oilseed plant of any one of 2-5, wherein said heterologous nucleotide sequence that encodes said pPLAIIIδ protein is expressed under the control of a constitutive or seed-specific promoter.

7. The transgenic oilseed plant of any one of 2-6, wherein said constitutive promoter is selected from the group consisting of CaMV35S, FMV35S, enhanced or duplicate CaMV35S, enhanced or duplicate FMV35S, the CaMV 19S promoter, the NOS promoter, the OCS promoter, the maize ubiquitin promoter, and the rice Act1 promoter, and said seed-specific promoter is selected from the group consisting of the β-conglycinin promoter, the Cim1 (cytokinin-induced message) promoter, the cZ19B1 (maize 19 KDa zein) promoter, the mi1ps (myo-inositol-1-phosphate synthase) promoter, the celA (cellulose synthase) promoter, the end1 (*Hordeum verlgase* mRNA clone END1) promoter, the imp3 (myo-inositol monophosphate-3) promoter, the phaseolin promoter, the napin promoter, the soybean lectin promoter, the oleosin promoter, and the napin promoter.

8. The transgenic oilseed plant of any one of 2-7, which is selected from the group consisting of plants of the genera *Brassica* (e.g., rapeseed/canola (*Brassica napus; Brassica carinata; Brassica nigra; Brassica oleracea*), *Camelina, Miscanthus*, and *Jatropha*; Jojoba (*Simmondsia chinensis*), coconut; cotton; peanut; rice; safflower; sesame; soybean; mustard other than *Arabidopsis*; wheat; flax (linseed); sunflower; olive; corn; palm; palm kernel; sugarcane; castor bean; switchgrass; *Borago officinalis; Echium plantagineum; Cuphea hookeriana; Cuphea pulcherrima; Cuphea lanceolata; Ricinus communis; Coriandrum sativum; Crepis alpina; Vernonia galamensis; Momordica charantia;* and *Crambe abyssinica*.

9. The transgenic oilseed plant of any one of 2-8, wherein said enhanced amount of oil is about 5% higher than that compared to the amount of oil in seeds of an otherwise identical control oilseed plant grown under the same conditions.

10. The transgenic oilseed plant of any one of 2-9, wherein said C20 fatty acids comprise C20:0, C20:1, C20:2, and said C22 fatty acid is C22:1.

11. The transgenic oilseed plant of any one of 2-10, wherein said enhanced amount of said C20 and C22 fatty acids in said oil is increased by about 10% to about 20% compared to the amount of said fatty acids in seed oil produced by an otherwise identical control oilseed plant grown under the same conditions.

12. The transgenic oilseed plant of any one of 2-11, wherein said enhanced amount of C56, C58, and C60 triacylglycerols is about 10% to about 20% higher than that compared to the amount of C56, C58, and C60 triacylglycerols produced by an otherwise identical control oilseed plant grown under the same conditions.

13. The transgenic oilseed plant of any one of 2-12, wherein said enhanced levels of mRNA transcripts for genes in the Kennedy pathway are in the range of from about two-fold to about ten-fold higher compared to the levels of mRNA transcripts for genes in the Kennedy pathway in an otherwise identical control oilseed crop plant grown under the same conditions.

14. The transgenic oilseed plant of 13, wherein said mRNA transcripts comprise transcripts of AAPT, AAPT1, AAPT2, CCT, CCT1, CCT2, GPAT, LPAT, LPAT2, LPAT3, LPCAT1, PAH, PAP, PDAT1, DGAT, and DGAT1.

15. The transgenic oilseed plant of any one of 2-14, wherein said enhanced amount of oil is about 5% higher, and said enhanced amount of C20 and C22 fatty acids is about 10% to about 20% higher, than that compared to the amount of oil or C20 and C22 fatty acids, respectively, produced by an otherwise identical control oilseed plant grown under the same conditions.

16. The transgenic oilseed plant of any one of 2-15, wherein said enhanced amount of oil is about 5% higher, and said enhanced amount of C56, C58, and C60 triacylglycerols is about 10% to about 20% higher, than that compared to the amount of oil or C56, C58, and C60 triacylglycerols, respectively, produced by an otherwise identical control oilseed plant grown under the same conditions.

17. The transgenic oilseed plant of any one of 2-16, wherein the amounts of C50, C52, and C54 triacylglyercols in said oil are lower than the amounts of C50, C52, and C54 triacylglyercols in oil produced by an otherwise identical control oilseed plant grown under the same conditions.

18. A method selected from the group consisting of:
(i) producing an enhanced amount of oil in seeds of an oilseed plant compared to the amount of oil produced in seeds by an otherwise identical control oilseed plant grown under the same conditions;
(ii) producing oil in seeds of an oilseed plant containing an enhanced amount of C20 and C22 fatty acids compared to the amount of C20 and C22 fatty acids in oil produced in seeds by an otherwise identical control oilseed plant grown under the same conditions;
(iii) producing oil in seeds of an oilseed plant containing an enhanced amount of C56, C58, and C60 triacylglycerols compared to the amount of C56, C58, and C60 triacylglycerols in oil produced in seeds by an otherwise identical control oilseed plant grown under the same conditions;
(iv) producing an enhanced amount of oil in seeds of an oilseed plant containing an enhanced amount of C20 and C22 fatty acids compared to the amount of oil and C20 and C22 fatty acids produced in seeds by an otherwise identical control oilseed plant grown under the same conditions;

(v) producing an enhanced amount of oil in seeds of an oilseed plant containing an enhanced amount of C56, C58, and C60 triacylglycerols compared to the amount of oil and C56, C58, and C60 triacylglycerols produced in seeds by an otherwise identical control oilseed plant grown under the same conditions;

(vi) producing an enhanced amount of oil in seeds of an oilseed plant containing an enhanced amount of C20 and C22 fatty acids and an enhanced amount of C56, C58, and C60 triacylglycerols compared to the amount of oil, C20 and C22 fatty acids, and C56, C58, and C60 triacylglycerols, respectively, produced in seeds by an otherwise identical control oilseed plant grown under the same conditions; and (vii) producing enhanced levels of mRNA transcripts for genes in the Kennedy pathway in seeds of an oilseed plant compared to the levels of mRNA transcripts for genes in the Kennedy pathway produced in seeds by an otherwise identical control oilseed plant grown under the same conditions, wherein said oilseed plant is a plant other than *Arabidopsis*, wherein said method comprises expressing or overexpressing a protein having at least 95% sequence similarity to *Arabidopsis* pPLAIIIδ protein comprising the amino acid sequence encoded by *Arabidopsis* Genome Initiative Database Accession At3g63200 in said oilseed plant, and wherein said pPLAIIIδ protein exhibits enzymatic activity in the range of from about 75% to about 125% or more of the enzymatic activity of said *Arabidopsis* pPLAIIIδ protein.

19. The method of 18, wherein said protein is *Arabidopsis* pPLAIIIδ comprising the amino acid sequence encoded by *Arabidopsis* Genome Initiative Database Accession At3g63200.

20. The method of 18 or 19, wherein said heterologous nucleotide sequence that encodes said pPLAIIIδ protein is expressed under the control of a constitutive or seed-specific promoter.

21. The method of claim 20, wherein said constitutive promoter is selected from the group consisting of CaMV35S, FMV35S, enhanced or duplicate CaMV35S, enhanced or duplicate FMV35S, the CaMV 19S promoter, the NOS promoter, the OCS promoter, the maize ubiquitin promoter, and the rice Act1 promoter, and said seed-specific promoter is selected from the group consisting of the β-conglycinin promoter, the Cim1 (cytokinin-induced message) promoter, the cZ19B1 (maize 19 KDa zein) promoter, the miIps (myo-inositol-1-phosphate synthase) promoter, the celA (cellulose synthase) promoter, the end1 (*Hordeum verlgase* mRNA clone END1) promoter, the imp3 (myo-inositol monophosphate-3) promoter, the phaseolin promoter, the napin promoter, the soybean lectin promoter, the oleosin promoter, and the napin promoter.

22. The method of any one of 18-21, wherein said oilseed plant is selected from the group consisting of plants of the genera *Brassica* (e.g., rapeseed/canola (*Brassica napus*; *Brassica carinata*; *Brassica nigra*; *Brassica oleracea*), *Camelina*, *Miscanthus*, and *Jatropha*; Jojoba (*Simmondsia chinensis*), coconut; cotton; peanut; rice; safflower; sesame; soybean; mustard other than *Arabidopsis*; wheat; flax (linseed); sunflower; olive; corn; palm; palm kernel; sugarcane; castor bean; switchgrass; *Borago officinalis*; *Echium plantagineum*; *Cuphea hookeriana*; *Cuphea pulcherrima*; *Cuphea lanceolata*; *Ricinus communis*; *Coriandrum sativum*; *Crepis alpina*; *Vernonia galamensis*; *Momordica charantia*; and *Crambe abyssinica*.

23. The method of any one of 18-22, wherein said enhanced amount of oil is about 5% higher than that compared to the amount of oil in seeds of an otherwise identical control oilseed plant grown under the same conditions.

24. The method of any one of 18-23, wherein said C20 fatty acids comprise C20:0, C20:1, C20:2, and said C22 fatty acid is C22:1.

25. The method of any one of 18-24, wherein said enhanced amount of said C20 and C22 fatty acids in said oil is increased by about 10% to about 20% compared to the amount of said fatty acids in seed oil produced by an otherwise identical control oilseed plant grown under the same conditions.

26. The method of any one of 18-25, wherein said enhanced amount of C56, C58, and C60 triacylglycerols is about 10% to about 20% higher than that compared to the amount of C56, C58, and C60 triacylglycerols produced by an otherwise identical control oilseed plant grown under the same conditions.

27. The method of any one of 18-26, wherein said enhanced levels of mRNA transcripts for genes in the Kennedy pathway are in the range of from about two-fold to about ten-fold higher compared to the levels of mRNA transcripts for genes in the Kennedy pathway in an otherwise identical control oilseed crop plant grown under the same conditions.

28. The method of 27, wherein said mRNA transcripts comprise transcripts of AAPT, AAPT1, AAPT2, CCT, CCT1, CCT2, GPAT, LPAT, LPAT2, LPAT3, LPCAT1, PAH, PAP, PDAT1, DGAT, and DGAT1.

29. The method of any one of 18-28, wherein said enhanced amount of oil is about 5% higher, and said enhanced amount of C20 and C22 fatty acids is about 10% to about 20% higher, than that compared to the amount of oil or C20 and C22 fatty acids, respectively, produced by an otherwise identical control oilseed plant grown under the same conditions.

30. The method of any one of 18-29, wherein said enhanced amount of oil is about 5% higher, and said enhanced amount of C56, C58, and C60 triacylglycerols is about 10% to about 20% higher, than that compared to the amount of oil or C56, C58, and C60 triacylglycerols, respectively, produced by an otherwise identical control oilseed plant grown under the same conditions.

31. The method of any one of 18-30, wherein the amounts of C50, C52, and C54 triacylgyercols in said oil are lower than the amounts of C50, C52, and C54 triacylglyercols in oil produced by an otherwise identical control oilseed plant grown under the same conditions.

32. A method of making a transgenic plant, or transgenic oilseed plant, other than *Arabidopsis*, of any one of 1-17, or the method of producing oil of any one of 18-31, comprising expressing or overexpressing a heterologous nucleotide sequence that encodes a pPLAIIIδ protein in said plant or said oilseed plant.

33. The methods of 32, wherein said pPLAIIIδ protein has at least 95% sequence similarity to *Arabidopsis* pPLAIIIδ protein comprising the amino acid sequence encoded by *Arabidopsis* Genome Initiative Database Accession At3g63200, and wherein said pPLAIIIδ protein exhibits enzymatic activity in the range of from about 75% to about 125% or more of the enzymatic activity of said *Arabidopsis* pPLAIIIδ protein.

34. The methods of 32 or 33, wherein said pPLAIIIδ protein comprises the amino acid sequence encoded by *Arabidopsis* Genome Initiative Database Accession At3g63200.

35. The methods of any one of 32-34, wherein said heterologous nucleotide sequence that encodes said pPLAIIIδ protein is expressed under the control of a constitutive or seed-specific promoter.

36. The methods of any one of 32-35, wherein said constitutive promoter is selected from the group consisting of CaMV35S, FMV35S, enhanced or duplicate CaMV35S, enhanced or duplicate FMV35S, the CaMV 19S promoter, the NOS promoter, the OCS promoter, the maize ubiquitin promoter, and the rice Act1 promoter, and said seed-specific promoter is selected from the group consisting of the β-conglycinin promoter, the Cim1 (cytokinin-induced message) promoter, the cZ19B1 (maize 19 KDa zein) promoter, the mi1ps (myo-inositol-1-phosphate synthase) promoter, the celA (cellulose synthase) promoter, the end1 (*Hordeum verlgase* mRNA clone END1) promoter, the imp3 (myo-inositol monophosphate-3) promoter, the phaseolin promoter, the napin promoter, the soybean lectin promoter, the oleosin promoter, and the napin promoter.

37. The methods of any one of 32-36, wherein said oilseed plant is selected from the group consisting of plants of the genera *Brassica* (e.g., rapeseed/canola (*Brassica napus; Brassica carinata; Brassica nigra; Brassica oleracea*), *Camelina, Miscanthus*, and *Jatropha*; Jojoba (*Simmondsia chinensis*), coconut; cotton; peanut; rice; safflower; sesame; soybean; mustard other than *Arabidopsis*; wheat; flax (linseed); sunflower; olive; corn; palm; palm kernel; sugarcane; castor bean; switchgrass; *Borago officinalis; Echium plantagineum; Cuphea hookeriana; Cuphea pulcherrima; Cuphea lanceolata; Ricinus communis; Coriandrum sativum; Crepis alpina; Vernonia galamensis; Momordica charantia*; and *Crambe abyssinica*.

38. A method of obtaining a composition or compound selected from the group consisting of oil; a C20 or C22 fatty acid; and a C56, C58, or C60 triacylglycerol from seeds of an oilseed plant other than *Arabidopsis*, comprising the steps of:
    expressing or overexpressing a heterologous nucleotide sequence that encodes a pPLAIIIδ protein in said oilseed plant, and
    recovering said oil, said C20 or C22 fatty acid, or said C56, C58, or C60 triacylglycerol, respectively, from said seeds,
    wherein the amount of said oil, said C20 or C22 fatty acid, or said C56, C58, or C60 triacylglycerol, respectively, obtained from said oilseed plant is greater than that obtained from an otherwise identical control oilseed plant grown under the same conditions.

39. The method of claim 38,
    wherein said pPLAIIIδ protein has at least 95% sequence similarity to *Arabidopsis* pPLAIIIδ protein comprising the amino acid sequence encoded by *Arabidopsis* Genome Initiative Database Accession At3g63200, and
    wherein said pPLAIIIδ protein exhibits enzymatic activity in the range of from about 75% to about 125% or more of the enzymatic activity of said *Arabidopsis* pPLAIIIδ protein.

40. The method of 38 or 39, wherein said pPLAIIIδ protein comprises the amino acid sequence encoded by *Arabidopsis* Genome Initiative Database Accession At3g63200.

41. The method of any one of 38-40, wherein said heterologous nucleotide sequence that encodes said pPLAIIIδ protein is expressed under the control of a constitutive or seed-specific promoter.

42. The method of 41, wherein said constitutive promoter is selected from the group consisting of CaMV35S, FMV35S, enhanced or duplicate CaMV35S, enhanced or duplicate FMV35S, the CaMV 19S promoter, the NOS promoter, the OCS promoter, the maize ubiquitin promoter, and the rice Act1 promoter, and said seed-specific promoter is selected from the group consisting of the β-conglycinin promoter, the Cim1 (cytokinin-induced message) promoter, the cZ19B1 (maize 19 KDa zein) promoter, the mi1ps (myo-inositol-1-phosphate synthase) promoter, the celA (cellulose synthase) promoter, the end1 (*Hordeum verlgase* mRNA clone END1) promoter, the imp3 (myo-inositol monophosphate-3) promoter, the phaseolin promoter, the napin promoter, the soybean lectin promoter, the oleosin promoter, and the napin promoter.

43. The method of any one of 38-42, wherein said oilseed plant is selected from the group consisting of plants of the genera *Brassica* (e.g., rapeseed/canola (*Brassica napus; Brassica carinata; Brassica nigra; Brassica oleracea*), *Camelina, Miscanthus*, and *Jatropha*; Jojoba (*Simmondsia chinensis*), coconut; cotton; peanut; rice; safflower; sesame; soybean; mustard other than *Arabidopsis*; wheat; flax (linseed); sunflower; olive; corn; palm; palm kernel; sugarcane; castor bean; switchgrass; *Borago officinalis; Echium plantagineum; Cuphea hookeriana; Cuphea pulcherrima; Cuphea lanceolata; Ricinus communis; Coriandrum sativum; Crepis alpina; Vernonia galamensis; Momordica charantia*; and *Crambe abyssinica*.

44. The transgenic plant, or transgenic oilseed plant, other than *Arabidopsis*, of any one of 1-17, produced by a method comprising, or the method of any one of 18-43, comprising:
    a) inserting into the genome of a plant cell or oilseed plant cell, other than an *Arabidopsis* cell, a recombinant, double-stranded DNA molecule comprising, operably linked for expression:
        (i) said promoter, that functions in plant cells to cause the transcription of an adjacent coding sequence to RNA;
        (ii) said heterologous nucleotide sequence that encodes said pPLAIIIδ protein;
        (iii) a 3' non-translated sequence that functions in plant cells to cause transcriptional termination and the addition of polyadenylate nucleotides to the 3' end of said transcribed RNA;
    b) obtaining a transformed plant cell or transformed oilseed plant cell; and
    c) regenerating from said transformed plant cell, or said transformed oilseed plant cell, a genetically transformed plant or oilseed plant, cells of which express or overexpress said pPLAIIIδ protein.

45. A transgenic plant or oilseed plant, other than *Arabidopsis*, produced by the method of 44.

46. Oil, a C20 or C22 fatty acid, or a C56, C58, or C60 triacylglycerol, obtained from seeds of said transgenic plant, or said transgenic oilseed plant, of any one of 1-17 or 44-45.

47. Oil, a C20 or C22 fatty acid, or a C56, C58, or C60 triacylglycerol, produced by the method of any one of 18-43.

48. A method of obtaining an edible or industrially useful oil, comprising extracting and recovering oil produced by a transgenic plant or transgenic oilseed plant of any one of 1-17 or 44-45, or which is produced by the method of any one of 18-43.

49. The method of 48, wherein said edible oil is selected from the group consisting of a cooking oil, a baking oil, a frying oil, a salad oil, and a nutritional supplement.

50. A method of producing a food product containing oil, a fatty acid, or a triacylglycerol, comprising incorporating oil, a fatty acid, or a triacylglycerol, respectively, obtained from a transgenic plant or transgenic oilseed plant of any one of 1-17 or 44-45 into said food product.

51. A food product made by the method of 50.

52. A method of producing a product selected from the group consisting of a cosmetic, a food supplement, a soap, a biofuel, a paint, a medicinal product, an aromatherapy product, a perfume or fragrance, a drying oil, a lubricant, an industrial oil, and a cleaning product, comprising incorporating oil, a fatty acid, or a triacylglycerol obtained from a transgenic plant or transgenic oilseed plant of any one of 1-17 or 44-45 into said product.

53. A product made by the method of 52.

54. The transgenic plant or transgenic oilseed plant, other than *Arabidopsis*, of any one of claim 1-17 or 44-45, or the method of any one of 18-43, wherein said pPLAIIIδ protein is expressed or overexpressed in embryos of seeds of said plants.

55. The transgenic plant or transgenic oilseed plant, other than *Arabidopsis*, of any one of 1-17 or 44-45, or the method of any one of 18-43, wherein expression of said heterologous nucleotide sequence that encodes said pPLAIIIδ protein is under the control of the 35S cauliflower mosaic virus promoter or β-conglycinin promoter.

56. Progeny of said transgenic plant or transgenic oilseed plant, other than *Arabidopsis*, of any one of 1-17 or 44-45.

57. The progeny of 56, which are produced sexually.

58. The progeny of 56, which are produced asexually.

59. The progeny of 58, which are produced asexually from cuttings.

60. A part of said plant or progeny of any one of 1-17, 44-45, 54-55, or 56-59, respectively.

61. The part of said plant or progeny of 60, which is selected from the group consisting of a protoplast, a cell, a tissue, an organ, a cutting, and an explant.

62. The part of said plant or progeny of 60, which is selected from the group consisting of an inflorescence, a flower, a sepal, a petal, a pistil, a stigma, a style, an ovary, an ovule, an embryo, a receptacle, a seed, a fruit, a stamen, a filament, an anther, a male or female gametophyte, a pollen grain, a meristem, a terminal bud, an axillary bud, a leaf, a stem, a root, a tuberous root, a rhizome, a tuber, a stolon, a corm, a bulb, an offset, a cell of said plant in culture, a tissue of said plant in culture, an organ of said plant in culture, and a callus.

Further scope of the applicability of the presently disclosed embodiments will become apparent from the detailed description and drawing(s) provided below. However, it should be understood that the detailed description and specific examples, while indicating preferred embodiments of this disclosure, are given by way of illustration only since various changes and modifications within the spirit and scope of these embodiments will become apparent to those skilled in the art from this detailed description.

BRIEF DESCRIPTION OF THE DRAWINGS

The above and other aspects, features, and advantages of the present disclosure will be better understood from the following detailed descriptions taken in conjunction with the accompanying drawing(s), all of which are given by way of illustration only, and are not limitative of the presently disclosed embodiments, in which:

FIG. 1(A-C) shows generation of knockout, overexpression, and complementation mutants of pPLAIIIs:

FIG. 2(A-E) shows that alterations of pPLAIIIδ change *Arabidopsis* seed oil content:

Values are means±SE (n=3). $^H$Significantly higher and $^L$Signifcantly lower, each at P<0.05 compared with the WT, based on Student's t test.

Figure 3A:
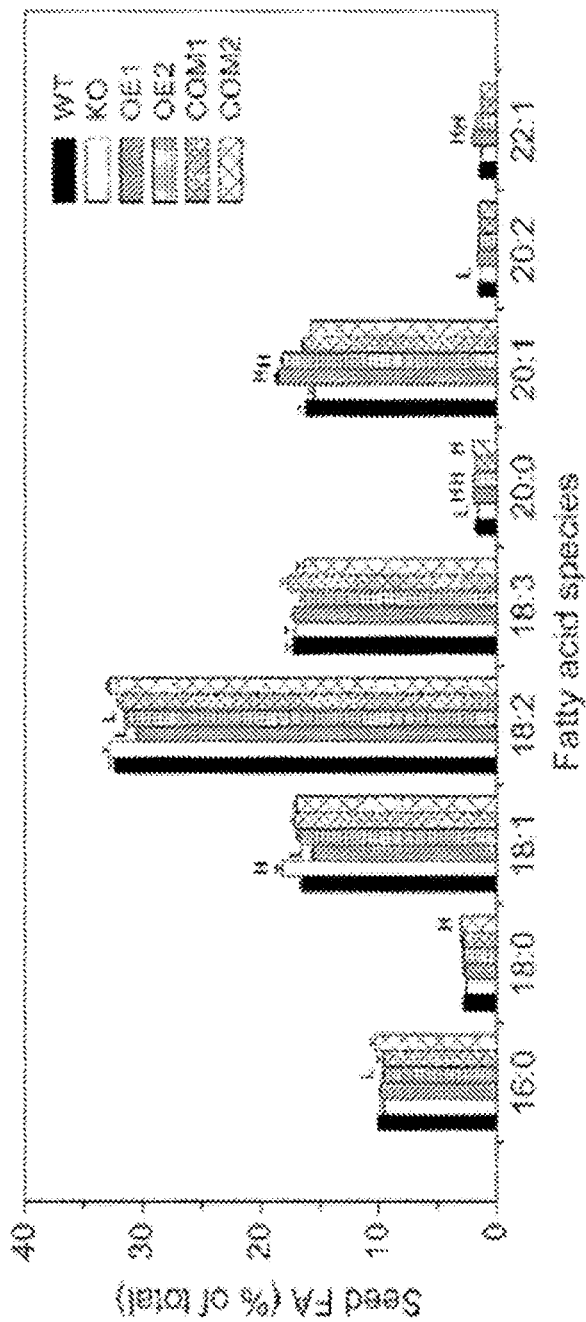
FIG. 3(A) Fatty acid compositions of pPLAIIIδ-KO, OE, COM, and WT seeds.
Figure 3B:
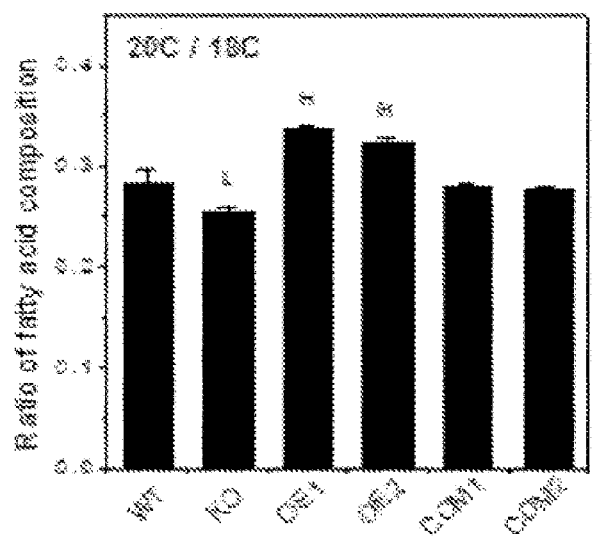
FIG. 3(A-B) shows that pPLAIIIδ increases 20C fatty acid content at the expense of 18C fatty acids.

FIG. 3(B) 20C/18C ratio in pPLAIIIδ-KO, OE, COM, and WT seeds. 20C/18C denotes fatty acids with 20 carbons over fatty acids with 18 carbons. Values are means±SE (n=3). $^H$Significantly higher and $^L$Signifcantly lower, each at P<0.05 compared with the WT, based on Student's t test.

Figure 4A:
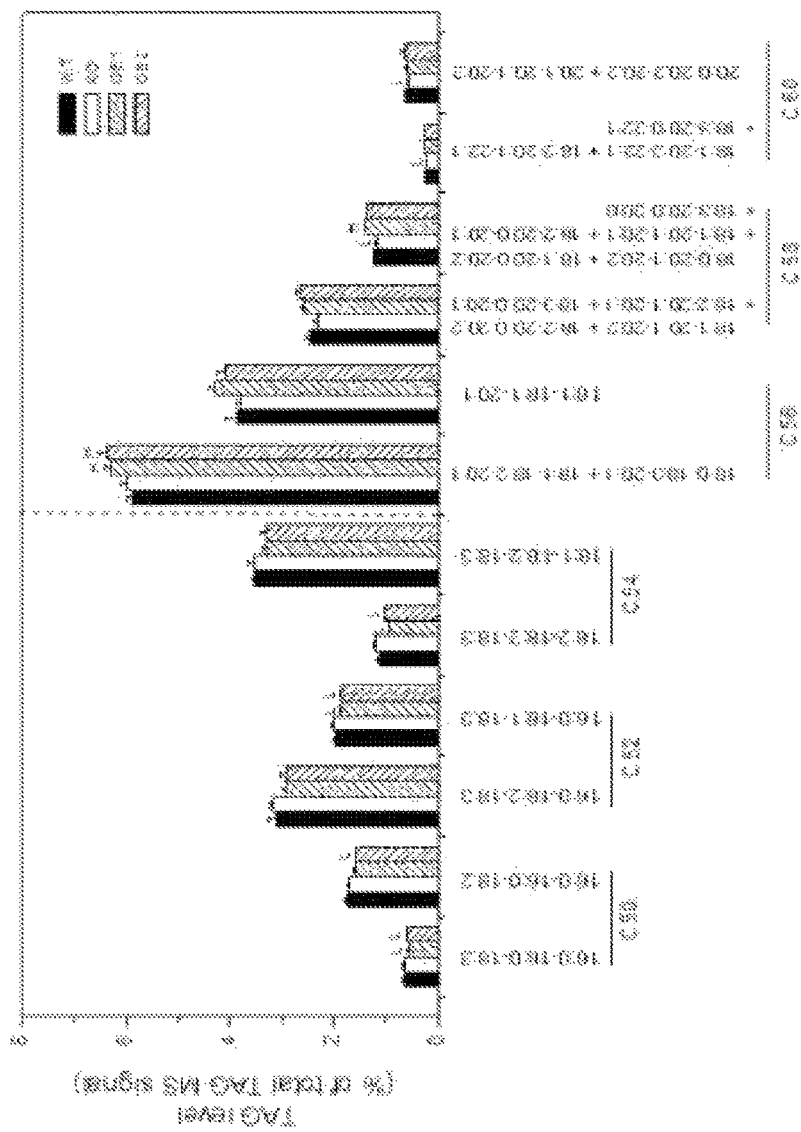

FIG. 4(A-B) shows that pPLAIIIδ promotes the accumulation of 20C-containing TAG species:

FIG. 4(A) Normalized mass spectra (as % of total) from TAG species with indicated fatty acyl combinations in WT, KO, and OE seeds. The fatty acids making up each molecular species are indicated, but no positional specificity is implied. The TAG species shown on left side of the dashed lines contain only 16- and 18-carbon chains, while those on the right include one or more 20-carbon chains. Values are means±SE (n=5). $^H$Significantly higher and $^L$Signifcantly lower, each at P<0.05 compared with the WT, based on Student's t test.

Figure 4B:
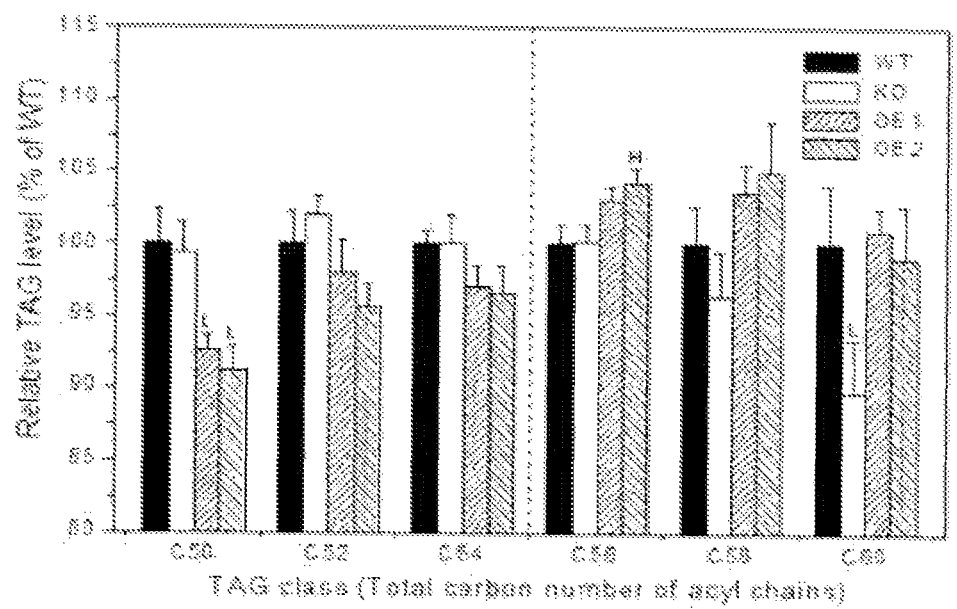

FIG. 4(B) Normalized mass spectra (as % of WT) from TAGs, grouped by total acyl carbons, were classified as C50, C52, C54, C56, C58, and C60. The major components in C50, C52, and C54 are 18C fatty acyl-containing TAGs, while C56, C58, and C60 are TAGs containing one or more 20C fatty acyl-containing TAGs. Values are means±SE (n=5). $^H$Significantly higher and $^L$Signifcantly lower, each at P<0.05 compared with the WT, based on Student's t test.

FIG. 5(A-F) shows that pPLAIIIδ promotes increased levels of 20C fatty acyl-containing TAG over 18C fatty acyl-containing TAG in *Arabidopsis* seeds, as determined by mass spectral analysis.

Figure 5A:
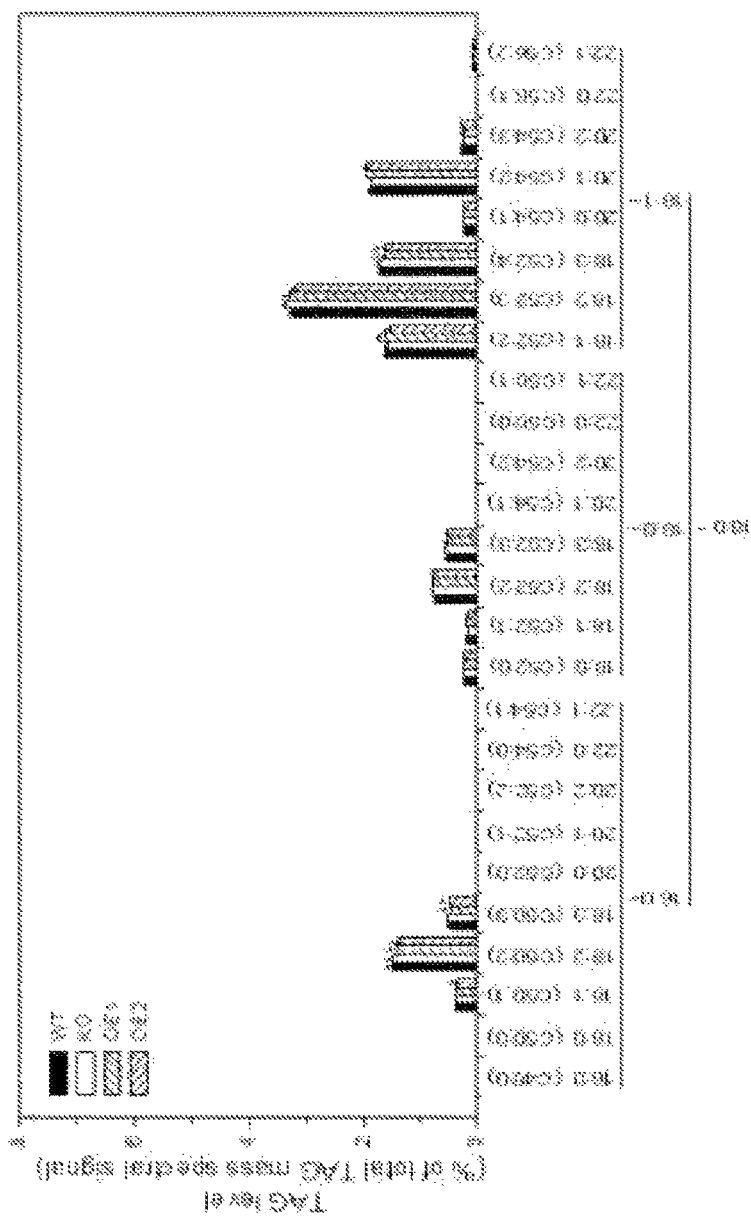

FIG. 5(A) shows levels of 120 individual TAG species in seeds of WT, KO, and OE mutants. Values are means±SE (n=5). $^H$Significantly higher and $^L$Signifcantly lower, each at P<0.05 compared with the WT, based on Student's t test.

Figure 5B:
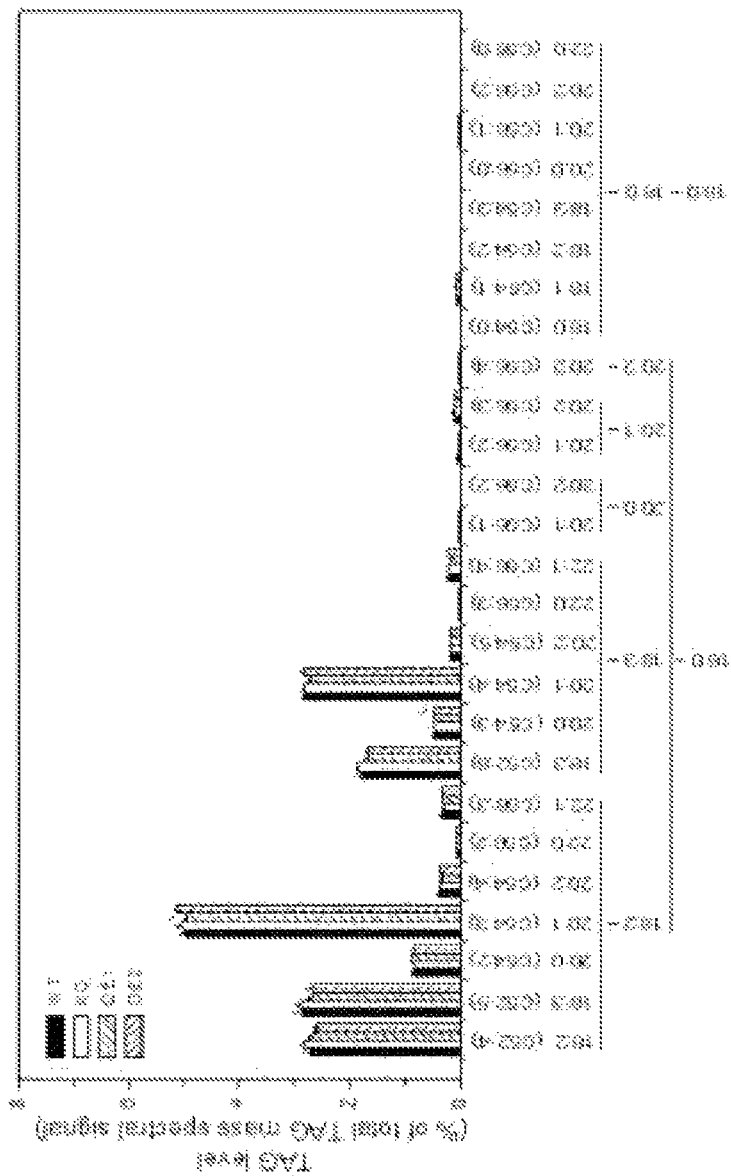

FIG. 5(B) shows levels of 120 individual TAG species in seeds of WT, KO, and OE mutants. Values are means±SE (n=5). $^H$Significantly higher and $^L$Signifcantly lower, each at P<0.05 compared with the WT, based on Student's t test.

Figure 5C:
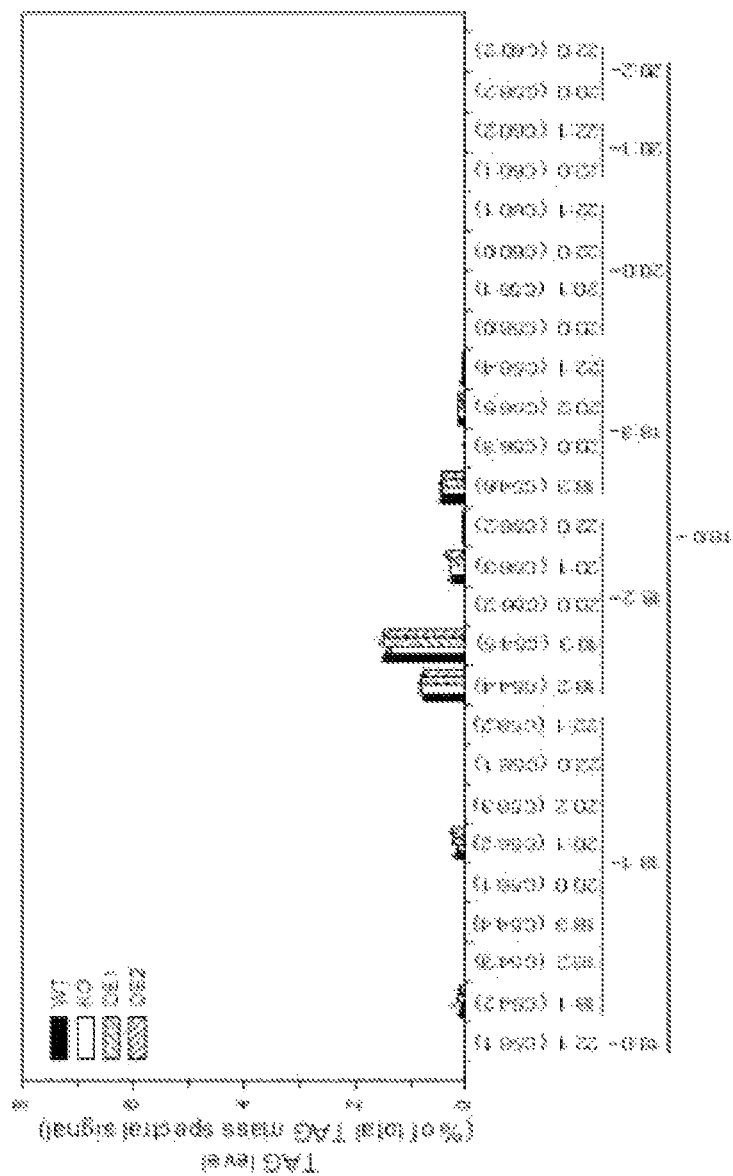

FIG. 5(C) shows levels of 120 individual TAG species in seeds of WT, KO, and OE mutants. Values are means±SE (n=5). $^H$Significantly higher and $^L$Signifcantly lower, each at P<0.05 compared with the WT, based on Student's t test.

Figure 5D:
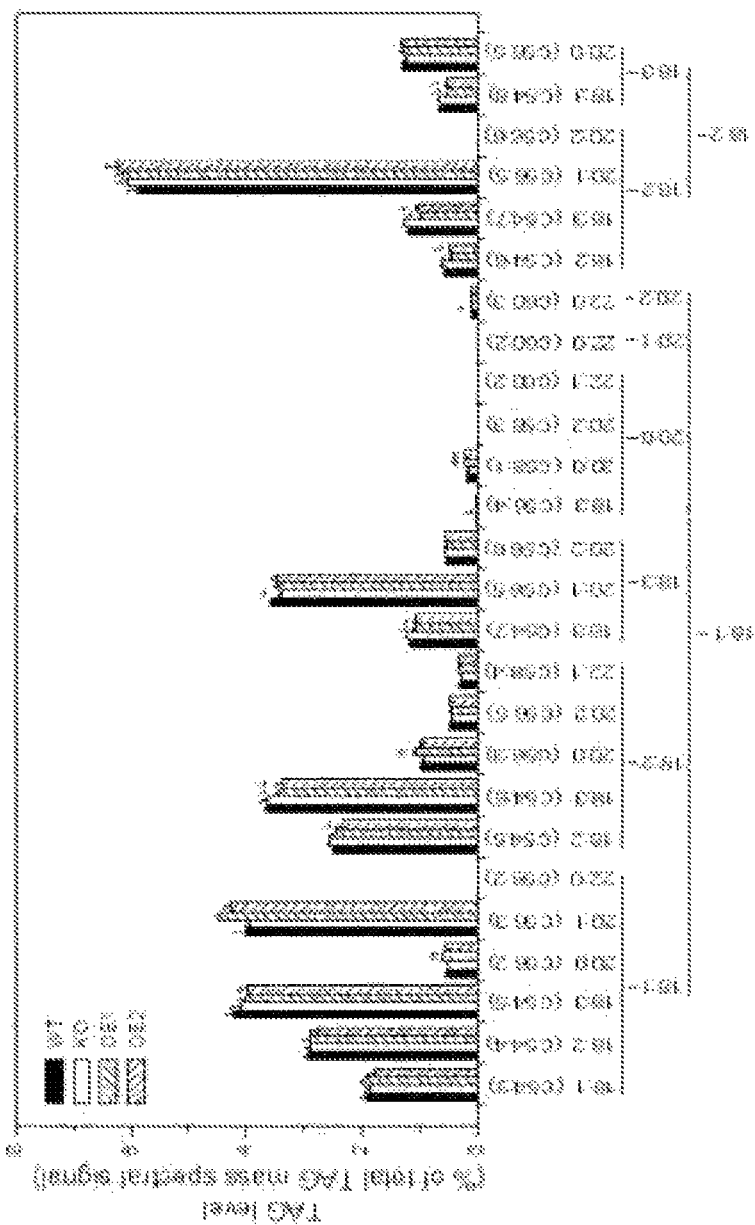

FIG. 5(D) shows levels of 120 individual TAG species in seeds of WT, KO, and OE mutants. Values are means±SE (n=5). $^H$Significantly higher and $^L$Signifcantly lower, each at P<0.05 compared with the WT, based on Student's t test.

Figure 5E:
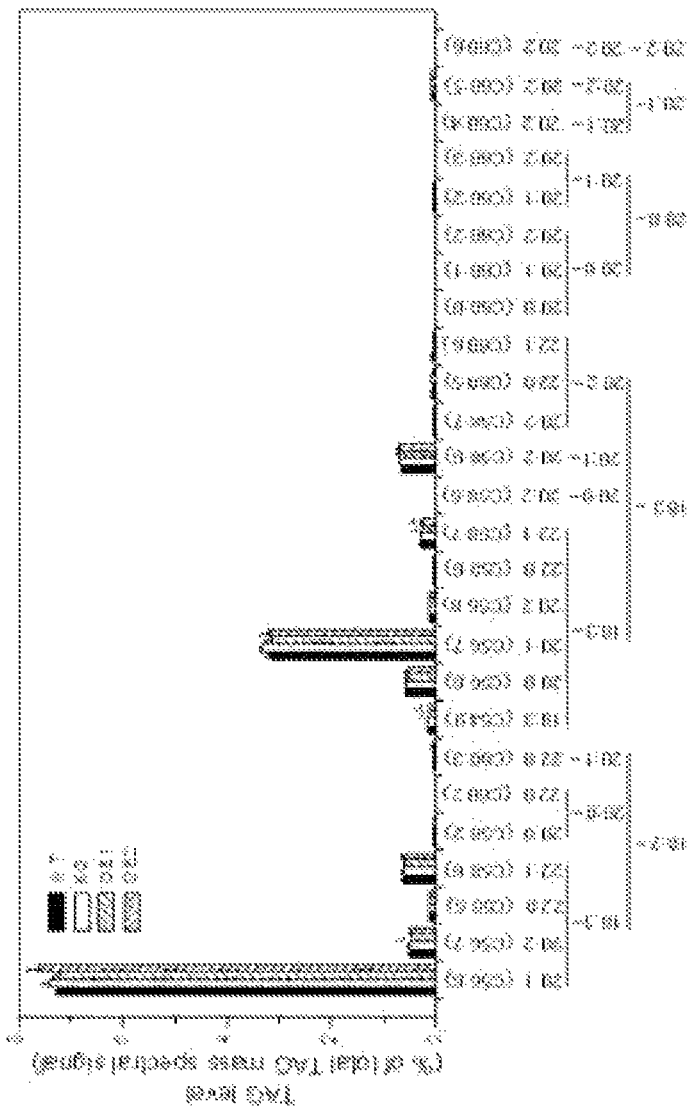

FIG. 5(E) shows levels of 120 individual TAG species in seeds of WT, KO, and OE mutants. Values are means±SE (n=5). $^H$Significantly higher and $^L$Signifcantly lower, each at P<0.05 compared with the WT, based on Student's t test.

Figure 5F:
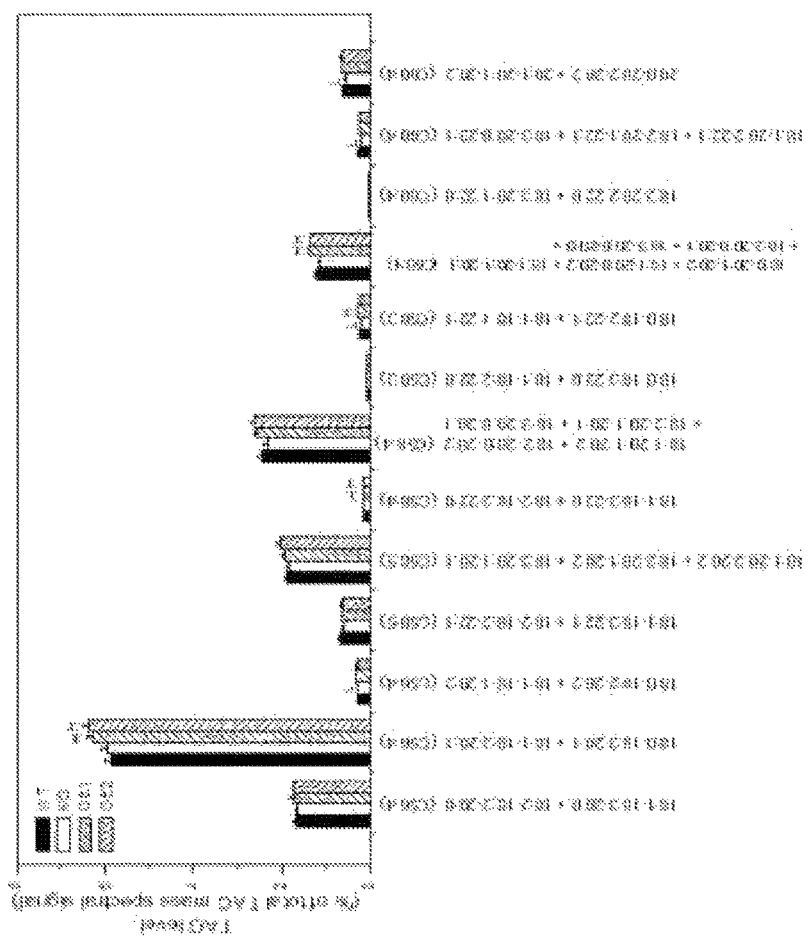

FIG. 5(F) shows levels of 120 grouped TAG species in seeds of WT, KO, and OE mutants. Values are means±SE (n=5). $^H$Significantly higher and $^L$Signifcantly lower, each at P<0.05 compared with the WT, based on Student's t test.

FIG. 6(A-B) shows that pPLAIIIδ increases the RNA level of genes in TAG and PC synthesis in siliques.

Figure 6A:
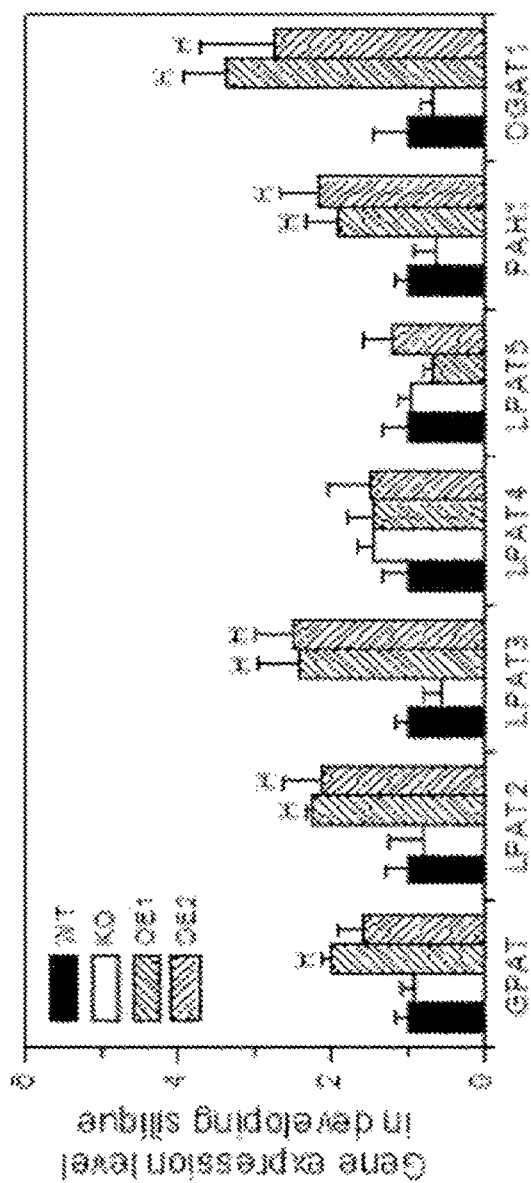

FIG. 6(A) RNA levels were determined by real time PCR and normalized in comparison to UBQ10. Values are means±SE (n=3 technical replicates). $^H$Significantly higher at P<0.05 compared with the WT, based on Student's t test. GPAT, Glycerol phosphate acyltransferase; LPAT, lysophosphatidic acid acyltransferase; PAH, PA phosphatase; DGAT, diacylglycerol acyltransferase; PDAT, phospholipid: diacylglycerol acyltransferase; LPCAT, LPC acyltransferase; AAPT, aminoalcohol-phosphotransferase; CCT, choline phosphate: CTP cytidylyltransferase.

Figure 6B:
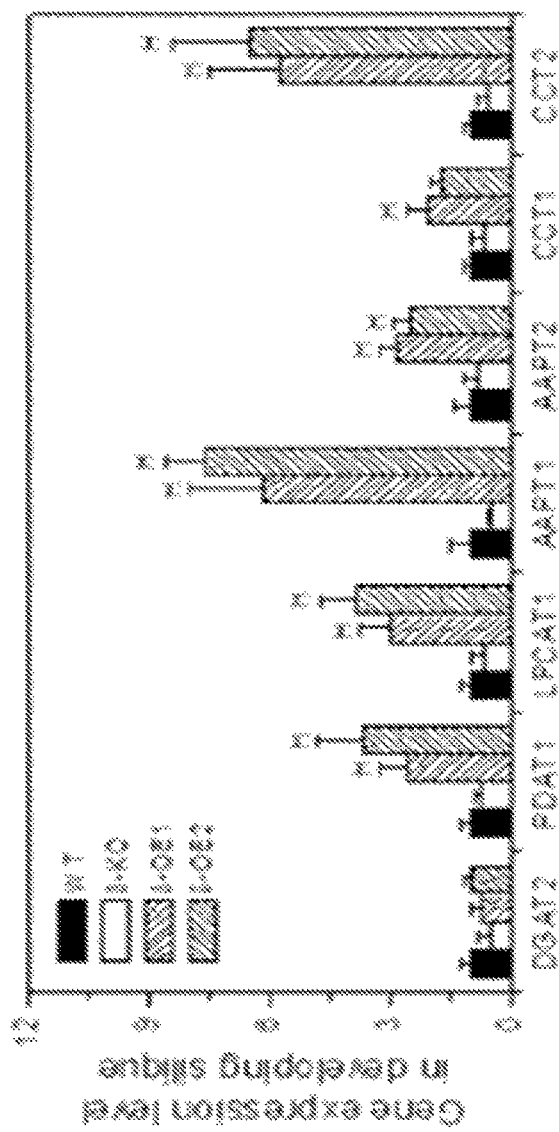

FIG. 6(B) RNA levels were determined by real time PCR and normalized in comparison to UBQ10. Values are means±SE (n=3 technical replicates). $^H$Significantly higher at P<0.05 compared with the WT, based on Student's t test. GPAT, Glycerol phosphate acyltransferase; LPAT, lysophosphatidic acid acyltransferase; PAH, PA phosphatase; DGAT, diacylglycerol acyltransferase; PDAT, phospholipid: diacylglycerol acyltransferase; LPCAT, LPC acyltransferase; AAPT, aminoalcohol-phosphotransferase; CCT, choline phosphate: CTP cytidylyltransferase.

Figure 7A:
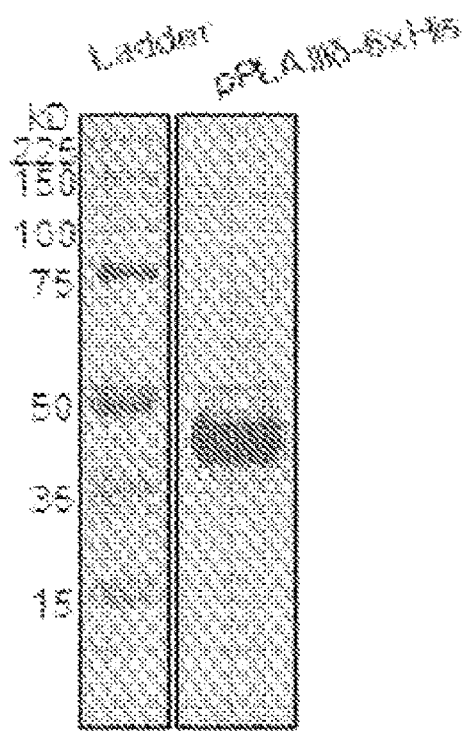

FIG. 7(A-C) shows the purification of pPLAIIIδ and that it hydrolyzes PC at the sn-1 and sn-2 positions:

FIG. 7(A) Coomassie blue staining of an 8% SDS-PAGE gel loaded with affinity purified pPLAIIIδ-6×His from *E. coli*.

Figure 7B:
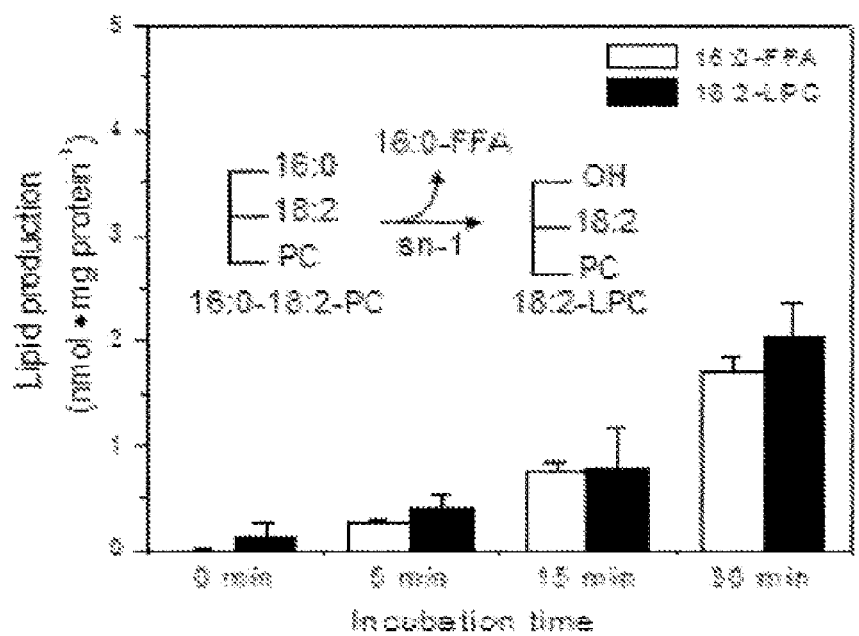

FIG. 7(B) Production of 16:0-free fatty acid and 18:2-lysophosphatidylcholine (18:2-LPC) from hydrolysis of 16:0-18:2 PC at the sn-1 position (inset). Values are means±SE (n=3 separate samples).

Figure 7C:
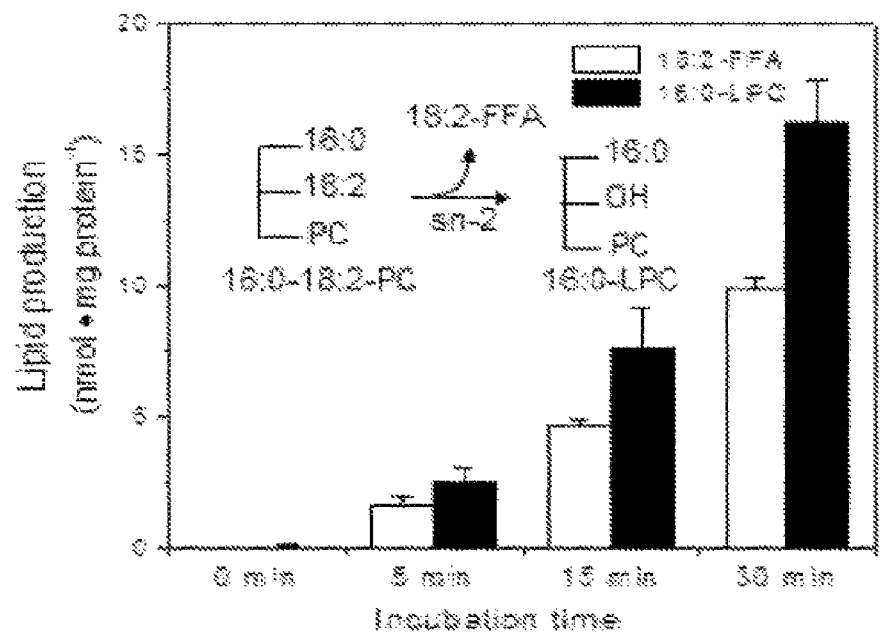

FIG. 7(C) Production of 18:2-free fatty acid and 16:0-LPC from hydrolysis of 16:0-18:2 PC at the sn-2 position (inset). Values are means±SE (n=3).

Figure 8A:
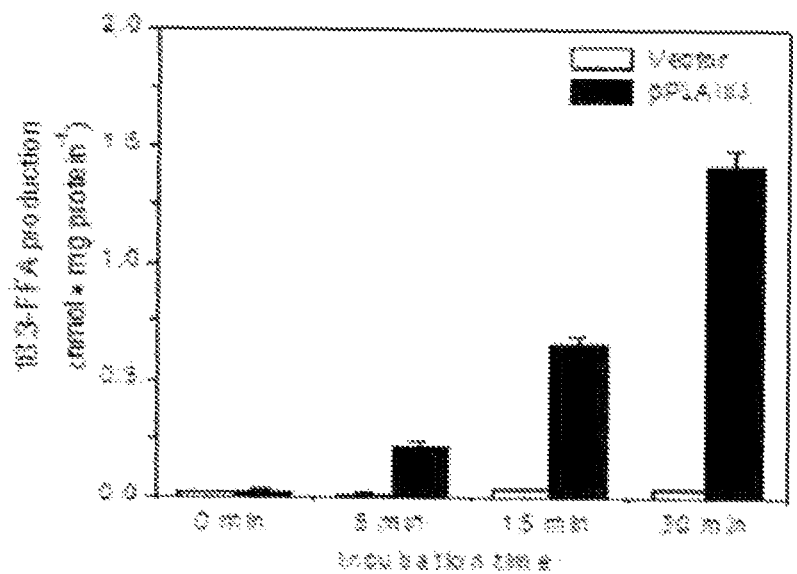

FIG. 8(A-C) shows that pPLAIIIδ hydrolyzes acyl-CoA and affects acyl-CoA levels in *Arabidopsis*:

FIG. 8(A) Free fatty acid 18:3 (18:3-FFA) released from 18:3-CoA in 16:0-18:2 PC vesicles by purified pPLAIIIδ. Vector refers to a control in which proteins from *E. coli* transformed with an empty vector were isolated using the same immunoaffinity procedure for purifying pPLAIIIδ-6×His. Values are means±SE (n=3).

Figure 8B:
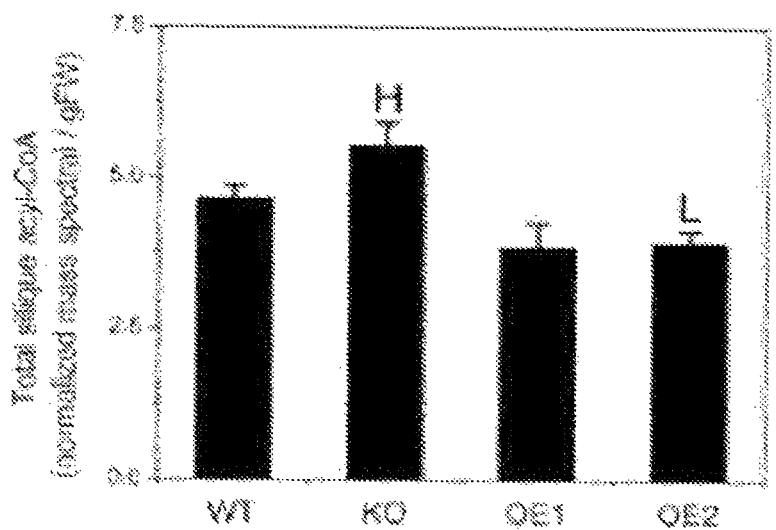

FIG. 8(B) Total acyl-CoA content in developing *Arabidopsis* siliques of WT, pPLAIIIδ-KO, OE, and COM plants.

Figure 8C:
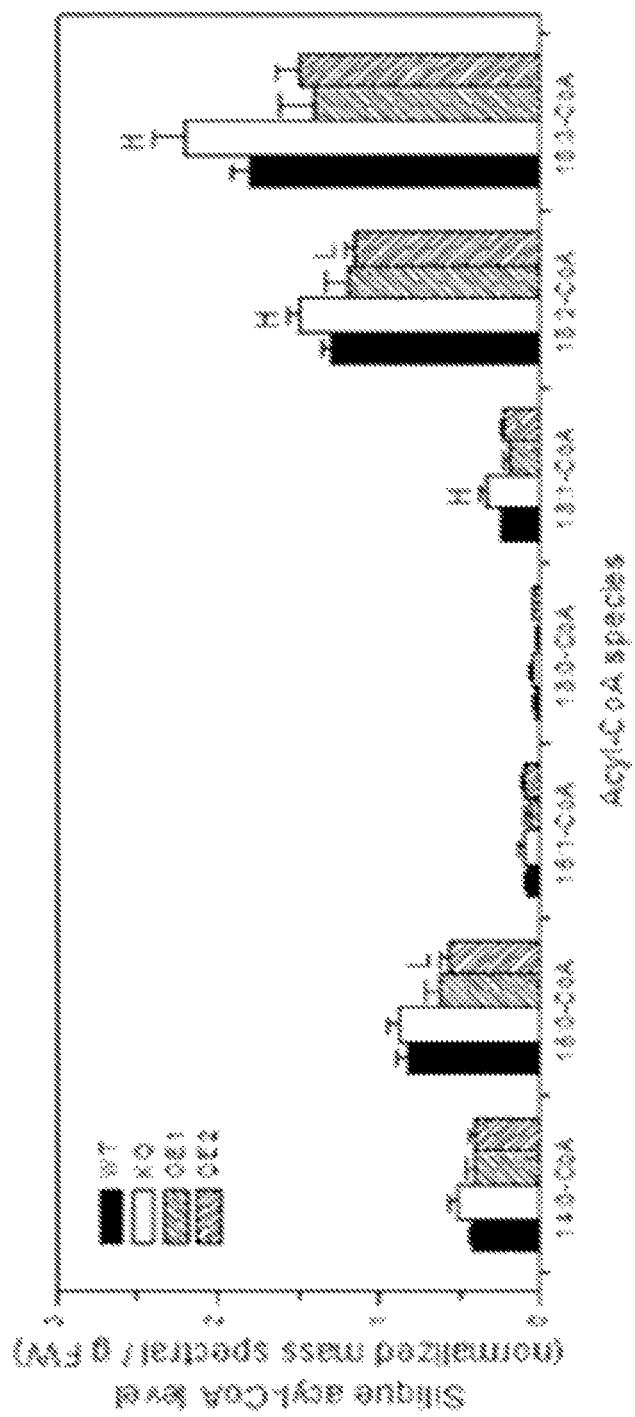

FIG. 8(C) Level of acyl-CoA molecular species in developing siliques of WT, pPLAIIIδ-KO, OE, and COM plants.

Acyl-CoAs were extracted from developing siliques 7 days post-pollination and analyzed by LC-ESI-MS/MS. Values are means±SE (n=5). $^H$Significantly higher and $^L$Signifcantly lower, each at P<0.05 compared with the WT, based on Student's t test.

Figure 9A:
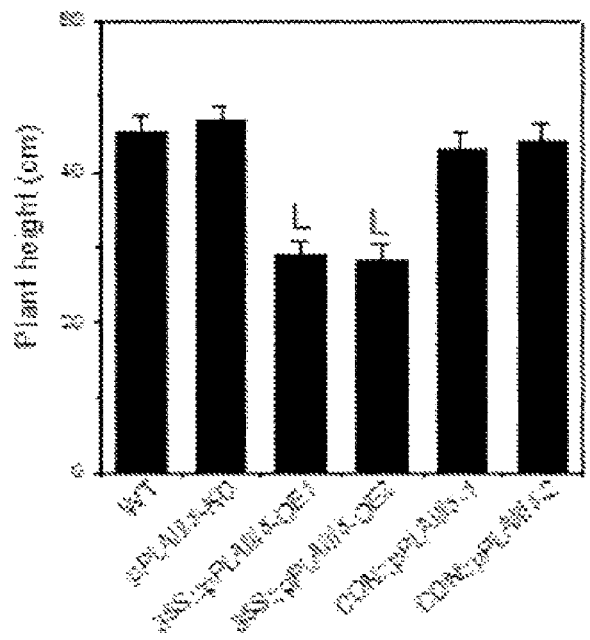

FIG. 9(A-E) shows that seed-specific overexpression of pPLAIIIδ increases oil content without compromising seed production:

FIG. 9(A) Plant heights of mature WT, pPLAIIIδ-KO, 35S::pPLAIIIδ, and CON::pPLAIIIδ plants. 35S represents cauliflower mosaic virus 35S promoter and CON represents the promoter of soybean β-conglycinin. Values are means±SE (n=5).

Figure 9B:
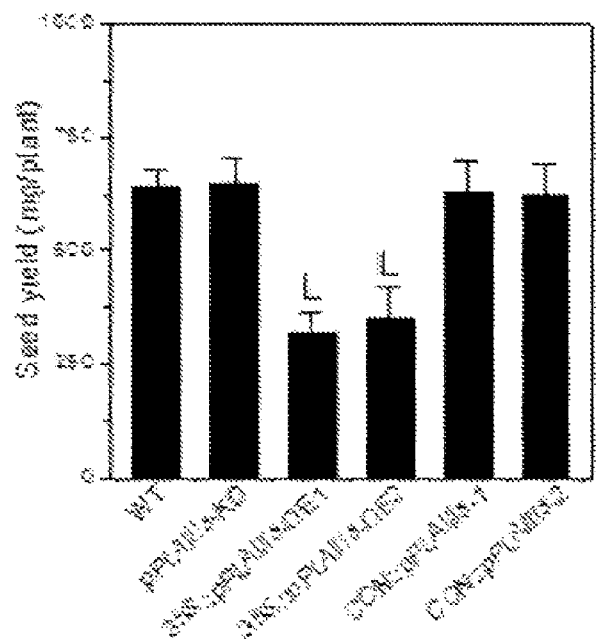

FIG. 9(B) Seed yield per plant of WT, pPLAIIIδ-KO, 35S::pPLAIIIδ, and CON::pPLAIIIδ plants. Values are means±SE (n=5).

Figure 9C:
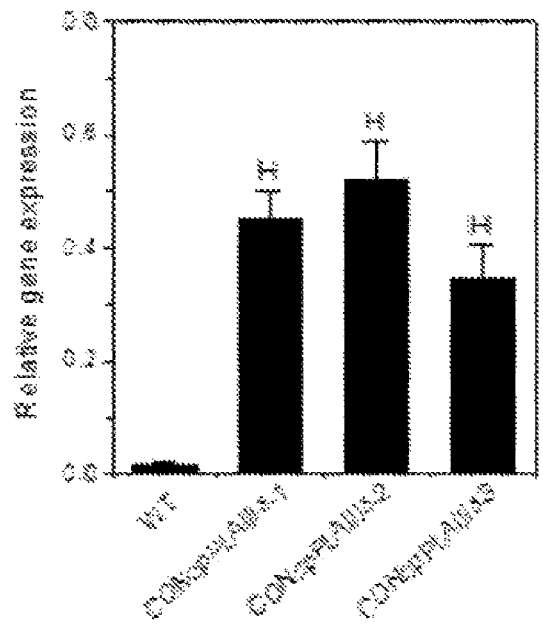

FIG. 9(C) Transcript levels of pPLAIIIδ in developing siliques of WT and three independent CON::pPLAIIIδ lines. The RNA level was determined by real time PCR and normalized in comparison to UBQ10. Values are means±SE (n=3).

Figure 9D:
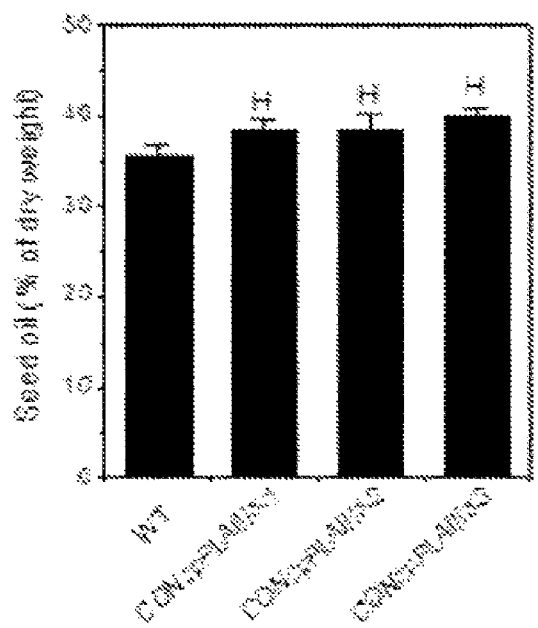

FIG. 9(D) Seed oil content in WT and three independent CON::pPLAIIIδ lines. Values are means±SE (n=3).

Figure 9E:
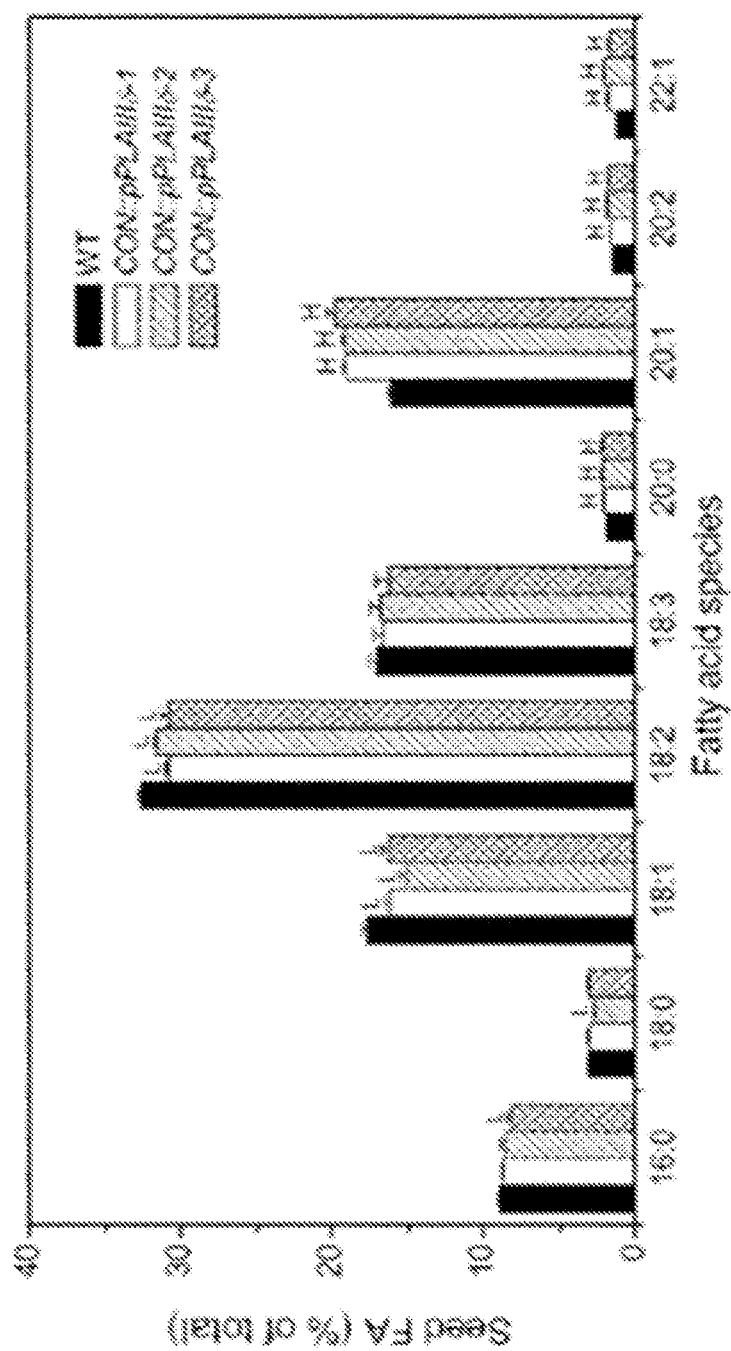

FIG. 9(E) Fatty acid compositions in WT and CON::pPLAIIIδ seeds. Values are means±SE (n=3). $^H$Significantly higher and $^L$Signifcantly lower, each at P<0.05 compared with the WT, based on Student's t test.

Figure 10A:

FIG. 10(A-D) shows seed specific overexpression of pPLAIIIδ in *Arabidopsis*:

FIG. 10(A) Constructs for generating seed specific expression mutants of pPLAIIIδ. *Arabidopsis* pPLAIIIδ genomic DNA cloned from start codon to stop codon (stop codon removed) was driven by soybean β-conglycinin promoter and tagged on C-terminus by green fluorescence protein and 6×Histidine tag. The resulting transgenic *Arabidopsis* were designated as CON::pPLAIIIδ. Ten independent lines of T3 generation mutants were obtained. The growth of the CON::pPLAIIIδ mutants was comparable with that of wild-type.

Figure 10B:
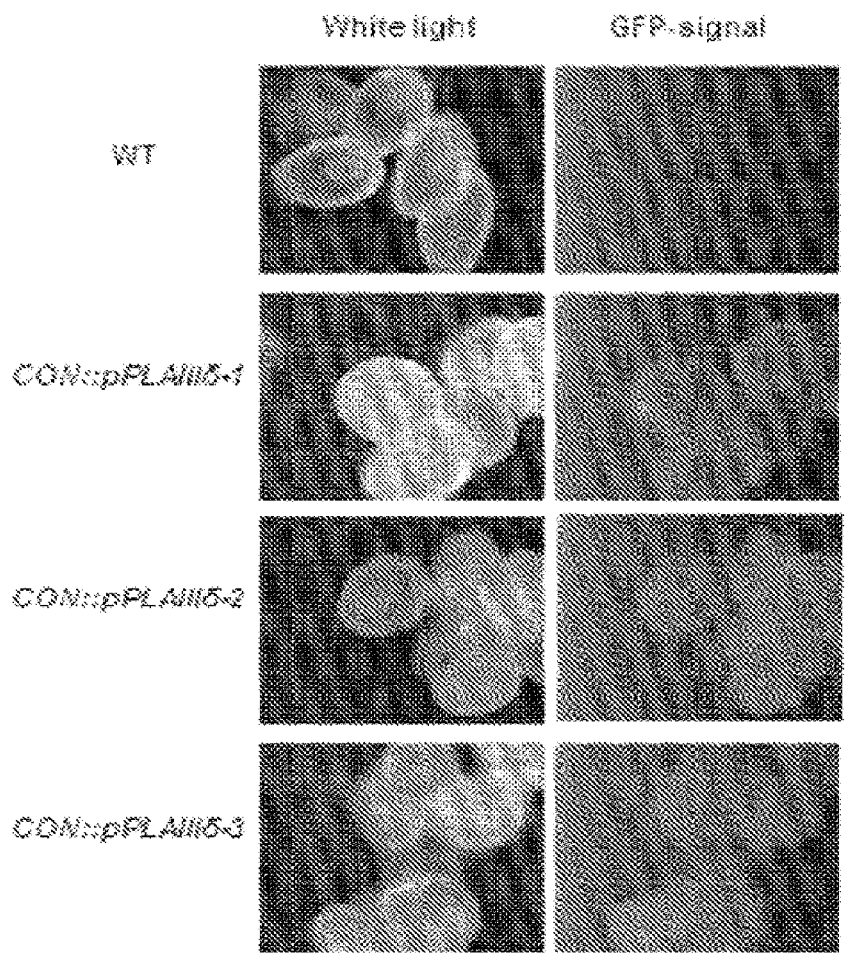

FIG. 10(B) Detection of the green fluorescence signal in developing seeds of CON::pPLAIIIδ mutants. Developing seeds from *Arabidopsis* siliques were imaged using a Nikon Eclipse 800 widefield microscope and a X60 differential interference contrast, 1.2-numerical aperture objective, with mercury lamp excitation and a 492/18 BP excitation filter and a 535/40 B emission filter.

Figure 10C:
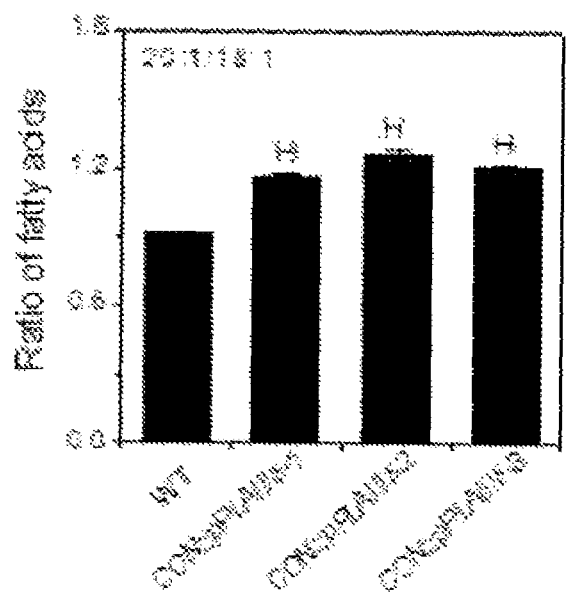

FIG. 10(C) Ratio of the level of fatty acids of 20:1 over 18:1 in seeds of WT and CON::pPLAIIIδ mutants. Values are means±SE (n=3). $^H$Significantly higher at P<0.05 compared with the WT, based on Student's t test.

Figure 10D:
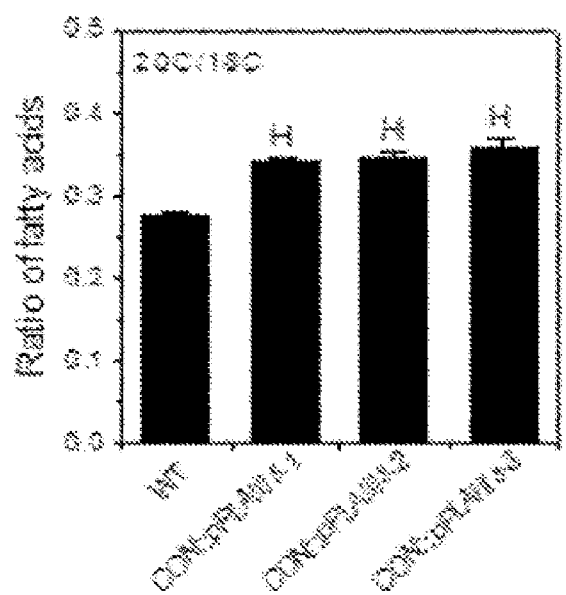

FIG. 10(D) Ratio of the level of fatty acids with 20 carbons over 18 carbons in seeds of WT and CON::pPLAIIIδ mutants. Values are means±SE (n=3). $^H$Significantly higher at P<0.05 compared with the WT, based on Student's t test.

Figure 11:
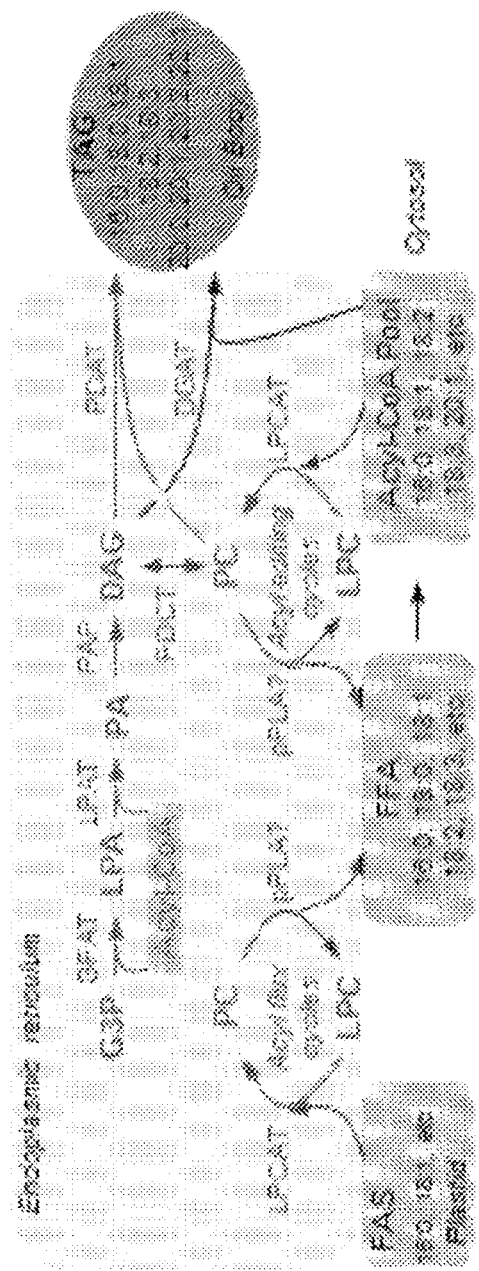

FIG. 11 shows the potential function of pPLAIIIδ on fatty acyl flux from plastid to ER and fatty acyl editing in ER.

Fatty acids are exclusively synthesized in plastids whereas glycerolipids are assembled in ER. In *Arabidopsis*, the fatty acids exported from plastids are majorly 16:0 and 18:1 but seed TAG are enriched in 18:2, 18:3, and 20:1. Therefore, fatty acyl flux and fatty acyl editing are needed in seed oil accumulation. pPLA may hydrolyze PC to generate LPC and FFA, where LPC can be re-used by LPCAT to form PC and FFA can be esterified to form acyl-CoA. pPLA may also hydrolyze acyl-CoA to FFA. PC and acyl-CoA are the sites for fatty acyl editing, such as desaturation and elongation.

DETAILED DESCRIPTION

The following detailed description is provided to aid those skilled in the art in practicing the various embodiments of the present disclosure described herein, including all the methods, uses, compositions, etc., described herein. Even so, the following detailed description should not be construed to unduly limit the present disclosure, as modifications and variations in the embodiments herein discussed may be made by those of ordinary skill in the art without departing from the spirit or scope of the present inventive discoveries.

The contents of all publications, patent applications, patents, and other references mentioned herein are incorporated by reference herein in their entirety. In case of conflict, the present specification, including explanations of terms, will control.

Any feature, or combination of features, described herein is(are) included within the scope of the present disclosure, provided that the features included in any such combination are not mutually inconsistent as will be apparent from the context, this specification, and the knowledge of one of ordinary skill in the art. Additional advantages and aspects of the present disclosure are apparent in the following detailed description and claims.

ABBREVIATIONS

The following abbreviations are defined for convenience to aid the reader in more easily understanding the ensuing discussion:

Acyl-CoA: acyl-Coenzyme A; DAG: diacylglycerol; DGAT: diacylglycerol acyltransferase; ER: endoplasmic reticulum; FFA: free fatty acids; G3P:glycerol-3-phosphate; GPAT: Glycerol phosphate acyltransferase; LPA: lysophosphatidic acid; LPAT: lysophosphatidic acid acyltransferase; LPC: lysophosphatidic acid; LPCAT: LPC acyltransferase; PA: phosphatidic acid; PAP: PA phosphatase; PC: phosphatidylcholine; PDAT: phospholipid: diacylglycerol acyltransferase; PDCT: PC:DAG cholinephosphotransferase; pPLAIII: group 3 of patatin-related phospholipase A, including pPLAIIIδ; TAG: triacylglycerol; pPLAIIIδ-COM: complementation lines; KO: knockout; OE: overexpressing; "VLCFAs" refers to very long chain fatty acids, i.e., fatty acids containing more than 18 carbon atoms.

OVERVIEW OF THE DISCLOSURE

The data presented herein demonstrate that pPLAIIIδ positively impacts seed oil content as well as fatty acid and TAG composition. Whereas pPLAIIIδ-KO decreases seed oil content, pPLAIIIδ-OE, driven either by a constitutive or seed-specific promoter, increases seed oil content. pPLAIIIδ hydrolyzes PC to generate FFA and LPC. pPLAIIIδ may accelerate acyl flux from the plastid to ER and therefore enhance glycerolipid synthesis. Fatty acids in higher plants are synthesized exclusively in the plastid and have to be exported to the ER where glycerolipids are synthesized (FIG. 11). Lipid trafficking between organelles is a fundamental, yet poorly understood, process in plants. In recent years, excellent progress has been made toward the understanding lipid transport from the ER to the plastid for the synthesis of galactolipids (Wang et al., 2012). PA is imported into the plastid through a protein complex (Wang and Benning, 2012). In contrast, the metabolic and regulatory mechanism by which fatty acids in the plastid are trafficked to the ER is unknown.

Plant oils represent an important renewable natural resource, and are primarily composed of TAG esters containing three fatty acids having chain lengths of C8-C24, with C16 and C18 predominating. The five most common fatty acids are palmitate (16:0), stearate (18:0), oleate (18:1), linoleate (18:2), and linolenate (18:3), although longer or shorter fatty acids may also be major constituents, depending on the particular plant species. These fatty acids differ from each other in terms of acyl chain length and number of double bonds, which impart different physical properties. Consequently, the properties of oil derived from a mixture of fatty acids are dependent on that composition, and altering the fatty acid profile can therefore improve the properties of the oil for use in different applications.

The majority of vegetable oils are produced from just four crops, i.e., oil palm, soybeans, rapeseed, and sunflower, which together account for approximately 79% of the total production. About 14% of the fats and oils are used chemically, and about 6% are used as feed material.

Dyer et al. ((2008) *The Plant Journal* 54:640-655) have reviewed the field of high-value oils from plants, including the biochemical and molecular mechanisms underlying seed oil production, and methods for the rational design and engineering of crop plants to optimize production of high-value oils in plant seeds.

Palmitic acid (16:0) and oleic acid (18:1) are two major FAs exported from the plastid in *Arabidopsis* (Pidkowich et al., 2007; Andersson and Kelly, 2010). Free FAs are thought to be able to cross membrane bilayers through diffusion and possibly protein-mediated translocation (Wang and Benning, 2012). After reaching the plastid outer envelope, long chain acyl-CoA synthetases (LACS) convert these FAs to acyl-CoA. In the conventional Kennedy pathway, acyl-CoA is used for sequential acylation of G3P→LPA→PA→DAG→TAG (FIG. 11). However, kinetic labeling data indicate that FAs exported from the plastid are first incorporated into PC and then channeled to TAG in soybean embryos (Bates et al., 2009; 2011; 2012). The presence of highly active LPCAT on the *Arabidopsis* plastid outer envelope membrane is consistent with the formation of PC using FAs from the plastids (Tjellstrom et al., 2012; Wang et al., 2012). Recent data indicate that LPCAT1 and LPCAT2 catalyze incorporation of fatty acids into PC in *Arabidopsis* seeds (Bates et al., 2012; Wang et al., 2012). However, knowledge is lacking about what enzyme produces LPC that impact TAG synthesis. PDAT can transfer a fatty acid from PC to DAG to produce TAG and LPC, but its role in TAG production in seeds remain unclear (Chapman and Ohlrogge, 2012). pPLAIIIδ could be one of the enzymes that hydrolyze PC to produce a free fatty acid and LPC that LPCAT uses to accept fatty acids from the plastid (FIG. 11). The combined activity of pPLAIII and LPCATs may modulate the rate of FA trafficking from the plastid to ER in *Arabidopsis* seeds.

Fatty acids, such as 18:1, released from PC by pPLAIIIδ, may enter the acyl-CoA pool for elongation (FIG. 11). As shown below, knockout and overexpression of the pPLAIIIδ gene displayed opposite effects on the levels of 18:1 and 20:1 fatty acids in seed oil. Detailed profiling of TAG molecules also shows the opposite effects on the levels of 18:1-containing and 20:1-containing TAGs by knockout and overexpression of pPLAIIIδ gene. In *Arabidopsis*, the major fatty acids exported from plastids to the ER are 16:0, 18:0, and 18:1. In the ER, 18:1 on PC is desaturated to 18:2 and 18:3 (Nishida and Bates, 2010), whereas acyl-CoA is used for FA elongation to form longer chain fatty acids, such as 20:1 (Joubès et al., 2008; Rowland and Bird, 2010). The effect of pPLAIIIδ on fatty acid composition is distinctively different from that of the recently described PC:DAG cholinephosphotransferase (PDCT) that transfers phosphocholine from PC to DAG, and a mutation of PDCT decreases the 18:2 and 18:3 level in *Arabidopsis* seed TAG by 40% (Lu et al., 2009). Thus, the increased pPLAIIIδ expression may facilitate the release of 18:1 from PC for 20:1 production (FIG. 11).

As shown below, compared to wild-type, plants overexpressing pPLAIIIδ had a lower acyl-CoA pool size in developing siliques, and higher seed oil content. The decrease in the acyl-CoA pool size could result from the thioesterase activity of pPLAIIIδ and/or increased PC turnover and TAG synthesis. The exchange of modified acyl groups between PC and the acyl-CoA pool requires extensive acyl editing cycles (Harwood, 1996). Through the acyl editing cycles, modified FAs enter the acyl-CoA pool to be utilized for glycerolipid synthesis, and acyl-CoA can be channeled into PC for further modification and directly for TAG production (Stymne and Stobart, 1984; Bafor et al., 1991; Bates et al., 2007; 2009). The inverse association between acyl-CoA pool and TAG contents could mean that the pPLAIIIδ-catalyzed turnover of acyl-CoA and PC promotes seed oil accumulation.

The enhanced mRNA level of genes, such as AAPT and CCT, in PC-biosynthesis in pPLAIIIδ-OE plants shown below indicates that increased pPLAIIIδ-mediated PC hydrolysis leads to an increase in PC biosynthesis and, thus increased PC turnover. Meanwhile, RNA levels are higher for genes in the Kennedy pathway, such as GPAT (glycerol-3-phosphate acyltransferase), LPAT, PAP (phosphatidic acid phosphohydrolase), and DGAT (diacylglycerol acyltransferase) in developing pPLAIIIδ-OE siliques. The increased transcript levels of glycerolipid-producing genes may be a feed-forward stimulation by enhanced substrate supplies as the increased pPLAIIIδ expression leads to elevated levels of FFAs and LPC. How the metabolic changes in FFAs and LPC is connected to the altered mRNA levels and potentially gene expression requires further investigation. In yeast, it has been shown that the transcriptional factor directly binds to PA, senses cellular PA levels, and regulates the expression of many genes involved in membrane lipid synthesis (Loewen et al., 2004). In addition, there is an increase in the mRNA level of LPC:acyl-CoA acyltransferase (LPCAT) which catalyzes the acylation of LPC using fatty acids from the plastid. This could mean an increase in fatty acid trafficking from the plastid to the ER, where glycerolipids are synthesized. Further studies are needed to determine the mechanism by which increased pPLAIIIδ expression promotes TAG production. Such investigation of how a lipid-hydrolyzing enzyme, such as pPLAIIIδ, promotes lipid accumulation has the potential to better our understanding of lipid metabolism and accumulation in plants.

In summary, the data presented herein show that pPLAIIIδ hydrolyzes PC to generate FFA and LPC, and genetic alterations of pPLAIIIδ expression change seed oil content and fatty acid and TAG composition in *Arabidopsis* seeds. The large scale of TAG species analysis reveals that pPLAIIIδ promotes the production of 20:1-TAG. We propose that pPLAIIIδ plays a role in fatty acyl flux from the plastid to ER and/or PC fatty acyl remodeling for TAG synthesis. Furthermore, the present results indicate that the use of seed-specific expression or overexpression of pPLAIIIδ has the potential to improve seed oil production in crops to produce both edible and industrially useful oils, fatty acids, and triacylglycerols.

pPLAIIIδ protein-encoding nucleotide sequences, and promoter nucleotide sequences used to drive their expression, can be genomic or non-genomic nucleotide sequences. Non-genomic nucleotide sequences encoding pPLAIIIδ and promoters include, for example, naturally-occurring mRNA, synthetically produced mRNA, naturally-occurring pPLAIIIδ DNA, or synthetically produced pPLAIIIδ DNA. Synthetic nucleotide sequences can be produced by means well known in the art, including by chemical or enzymatic synthesis of oligonucleotides, and include, for example, cDNA, codon-optimized sequences for efficient expression in different transgenic plants and transgenic oilseed plants reflecting the pattern of codon usage in such plants, variants containing conservative (or non-conservative) amino acid substitutions that do not adversely affect their normal activity, PCR-amplified nucleotide sequences, etc.

DEFINITIONS

The following definitions are provided to aid the reader in understanding the various aspects of the present disclosure. Unless defined otherwise, all technical and scientific terms used herein have the same meaning as commonly understood by those of ordinary skill in the art to which the disclosure pertains.

The singular terms "a", "an", and "the" include plural referents unless context clearly indicates otherwise. Similarly, the word "or" is intended to include "and" unless the context clearly indicates otherwise. Hence, comprising A or B means including A, or B, or A and B.

The term "about" as used herein is a flexible word with a meaning similar to "approximately" or "nearly". "About" indicates that exactitude is not claimed, but rather a contemplated variation of a stated value that varies by ±30%, ±25%, ±20%, ±15%, ±10%, ±9%, ±8%, ±7%, ±6%, ±5%, ±4%, ±3%, ±2%, or ±1% compared to that stated value.

The endpoints of all ranges disclosed herein directed to the same component or property are inclusive and independently combinable (e.g., ranges of "up to about 25 wt. %, or, more specifically, about 5 wt. % to about 20 wt. %," is inclusive of the endpoints and all intermediate values of the ranges of "about 5 wt. % to about 25 wt. %," etc.).

The term "control plant" refers to a plant without introduced trait-improving recombinant DNA. A control plant is used as a standard against which to measure and compare trait improvement in a transgenic plant comprising such trait-improving recombinant DNA. One suitable type of control plant is a non-transgenic plant of the parental line that was used to generate a transgenic plant, i.e., an otherwise identical wild-type plant. Another type of suitable control plant is a transgenic plant that comprises recombinant DNA without the specific trait-producing DNA, e.g., simply an empty vector.

The terms "enhance", "enhanced", "increase", or "increased" refer to a statistically significant increase. For the avoidance of doubt, these terms generally refer to about a 5% increase in a given parameter or value, about a 10% increase, about a 15% increase, about a 20% increase, about a 25% increase, about a 30% increase, about a 35% increase, about a 40% increase, about a 45% increase, about a 50% increase, about a 55% increase, about a 60% increase, about a 65% increase, about 70% increase, about a 75% increase, about an 80% increase, about an 85% increase, about a 90% increase, about a 95% increase, about a 100% increase, or more over the control value. These terms also encompass ranges consisting of any lower indicated value to any higher indicated value, for example "from about 5% to about 50%", etc.

The term "comprising" as used in a claim herein is open-ended, and means that the claim must have all the features specifically recited therein, but that there is no bar on additional features that are not recited being present as well. The term "comprising" leaves the claim open for the inclusion of unspecified ingredients even in major amounts. The term "consisting essentially of" in a claim means that the invention necessarily includes the listed ingredients, and is open to unlisted ingredients that do not materially affect the basic and novel properties of the invention. A "consisting essentially of" claim occupies a middle ground between closed claims that are written in a closed "consisting of" format and fully open claims that are drafted in a "comprising' format". These terms can be used interchangeably herein if, and when, this may become necessary.

Furthermore, the use of the term "including", as well as other related forms, such as "includes" and "included", is not limiting.

"A pPLAIIIδ protein" refers to a protein exhibiting enzymatic activity similar or identical to the enzymatic activity of *Arabidopsis* pPLAIIIδ protein comprising the amino acid sequence encoded by *Arabidopsis* Genome Initiative Database Accession At3g63200 (SEQ ID NO: 58). Several enzymatic activities of this *Arabidopsis* pPLAIIIδ are described below in Example 4, and include PC-hydrolyzing activity at both sn-1 and sn-2 positions and preferential release of 18:2 from the sn-2 position, as well as acyl-CoA thioesterase activity. "Similar" pPLAIIIδ enzymatic activity of a protein can be in the range of from about 75% to about 125% or more of the enzymatic activity of *Arabidopsis* pPLAIIIδ protein when equal amounts of both proteins are assayed as described in Example 4 under identical conditions.

The term "heterologous" refers to a nucleic acid fragment or protein that is foreign to its surroundings. In the context of a nucleic acid fragment, this is typically accomplished by introducing such fragment, derived from one source, into a different host. Heterologous nucleic acid fragments, such as coding sequences that have been inserted into a host organism, are not normally found in the genetic complement of the host organism. As used herein, the term "heterologous" also refers to a nucleic acid fragment derived from the same organism, but which is located in a different, e.g., non-native, location within the genome of this organism. Thus, the organism can have more than the usual number of copy(ies) of such fragment located in its(their) normal position within the genome and in addition, in the case of plant cells, within different genomes within a cell, for example in the nuclear genome and within a plastid or mitochondrial genome as well. A nucleic acid fragment that is heterologous with respect to an organism into which it has been inserted or transferred is sometimes referred to as a "transgene."

A "heterologous" pPLAIIIδ protein-encoding nucleotide sequence can be one or more additional copies of an endogenous pPLAIIIδ protein-encoding nucleotide sequence, or a nucleotide sequence from another plant or other source. Furthermore, these can be genomic or non-genomic nucleotide sequences. Non-genomic nucleotide sequences encoding pPLAIIIδ include, for example, mRNA, and synthetically produced pPLAIIIδ DNA including, for example, cDNA and codon-optimized sequences for efficient expression in different transgenic plants and transgenic oilseed plants reflecting the pattern of codon usage in such plants.

A "transgenic" organism, such as a transgenic plant, is a host organism that has been genetically engineered to contain one or more heterologous nucleic acid fragments, including nucleotide coding sequences, expression cassettes, vectors, etc. Introduction of heterologous nucleic acids into a host cell to create a transgenic cell is not limited to any particular mode of delivery, and includes, for example, microinjection, adsorption, electroporation, particle gun bombardment, whiskers-mediated transformation, liposome-mediated delivery, *Agrobacterium*-mediated transfer, the use of viral and retroviral vectors, etc., as is well known to those skilled in the art.

The term "genome" can collectively refer to the totality of different genomes within plant cells, i.e., nuclear genome, plastid (especially chloroplast genome), and mitochondrial genome, or separately to the each of these individual genomes when specifically indicated. As used herein, the term "genome" refers to the nuclear genome unless indicated otherwise. The preferred "genome" for expression of the pPLAIIIδ proteins employed in the present recombinant methods and plants is the nuclear genome. However, expression in a plastid genome, e.g., a chloroplast genome, or targeting of a pPLAIIIδ protein to a plastid genome such as a chloroplast via the use of a plastid targeting sequence, is also encompassed by the present disclosure.

Promoters

A variety of different promoters can be used in the practice of the present methods depending upon the desired location of pPLAIIIδ protein expression within a plant, level of expression, timing of expression, developmental stage of expression, response to environmental stimuli, etc.

Overexpression of pPLAIIIδ protein can be achieved by methods well known in the art such as the use of strong promoters, constitutive promoters, use of multiple copies of the pPLAIIIδ gene, etc.

The following are representative non-limiting examples of promoters that can be used in the expression cassettes of the present invention.

Constitutive Promoters: Constitutive promoters typically provide for the constant and substantially uniform production of proteins in all tissues. For example, the promoter can be a viral promoter such as a CaMV35S or FMV35S promoter. The CaMV35S and FMV35S promoters are active in a variety of transformed plant tissues and most plant organs (e.g., callus, leaf, seed, and root). Enhanced or duplicate versions of the CaMV35S and FMV35S promoters are particularly useful in the practice of this invention (U.S. Pat. No. 5,378,619, incorporated herein by reference in its entirety). Other useful promoters include the nopaline synthase (NOS) and octopine synthase (OCS) promoters (which are carried on tumor-inducing plasmids of *A. tumefaciens*), the cauliflower mosaic virus (CaMV) 19S promoters, a maize ubiquitin promoter, the rice Act1 promoter, and the Figwort Mosaic Virus (FMV) 35S promoter (see, e.g., U.S. Pat. No. 5,463,175, incorporated herein by reference in its entirety).

Other exemplary constitutive promoters include, for example, the core promoter of the Rsyn7 (U.S. patent application Ser. No. 08/661,601), the core CaMV 35S promoter (Odell et al. (1985) Nature 313:810-812); rice actin (McElroy et al. (1990) Plant Cell 2:163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. patent application Ser. No. 08/409,297), and the like. Other constitutive promoters include, for example, those disclosed in U.S. Pat. Nos. 5,608,149; 5,608,144; 5,604,121; 5,569,597; 5,466,785; 5,399,680; 5,268,463; and 5,608,142.

Tissue-Specific and developmentally regulated promoters: Examples of useful tissue-specific, developmentally regulated promoters include, but are not limited to, the β-conglycinin 7S promoter (Doyle et al., 1986), seed-specific promoters (Lam and Chua, 1991), and promoters associated with napin, phaseolin, zein, soybean trypsin inhibitor, ACP, stearoyl-ACP desaturase, or oleosin genes. Tissue-specific promoters also include those described in Yamamoto et al. (1997) Plant J. 12(2):255-265; Kawamata et al. (1997) Plant Cell Physiol. 38(7):792-803; Hansen et al. (1997) Mol. Gen. Genet. 254(3):337-343; Russell et al. (1997) Transgenic Res. 6(2):157-168; Rinehart et al. (1996) Plant Physiol. 112(3):1331-1341; Van Camp et al. (1996) Plant Physiol. 112(2):525-535; Canevascini et al. (1996) Plant Physiol. 112(2):513-524; Yamamoto et al. (1994) Plant Cell Physiol. 35(5):773-778; Lam (1994) Results Probl. Cell Differ. 20:181-196; Orozco et al. (1993) Plant Mol. Biol. 23(6):1129-1138; Matsuoka et al. (1993) Proc. Natl. Acad. Sci. U.S.A. 90(20):9586-9590; and Guevara-Garcia et al. (1993) Plant J. 4(3):495-505.

Seed-specific promoters: These include both promoters active during seed development as well as seed-germinating promoters (those promoters active during seed germination). Such promoters include β-conglycinin, (Fujiwara & Beachy (1994) Plant. Mol. Biol. 24 261-272); Cim1 (cytokinin-induced message); cZ19B1 (maize 19 KDa zein); milps (myo-inositol-1-phosphate synthase); celA (cellulose synthase); end1 (*Hordeum verlgase* mRNA clone END1); and imp3 (myo-inositol monophosphate-3). For dicots, particular promoters include phaseolin, napin, β-conglycinin, soybean lectin, and the like. For monocots, particular promoters include maize 15 Kd zein, 22 KD zein, 27 kD zein, waxy, shrunken 1, shrunken 2, globulin 1, etc. In certain embodiments the DNA constructs, transgenic plants and methods can employ the oleosin promoter and/or napin promoter.

The promoter of choice can be excised from its source by restriction enzymes, but can alternatively be PCR-amplified using primers that carry appropriate terminal restriction sites.

Nomenclature of Fatty Acids

"C" plus the number before a colon indicates the total number of carbon atoms in a fatty acid chain. Thus, C18 refers to a fatty acid containing 18 carbon atoms. The number after the colon represents the number of double bonds in the fatty acid carbon chain, and the number after Δ indicates the position of the double bond with respect to the carboxyl end of the fatty acid. Thus, for example, oleic acid is represented as C18:1Δ$^9$, i.e., an 18-carbon long fatty acid containing a single double bond at the Δ$^9$ position. Double bonds are in the cis configuration unless otherwise indicated.

By "very long chain fatty acid," as used herein is meant a saturated fatty acid, unsaturated fatty acid, or mixture thereof. Very long chain fatty acids may have one or more points of unsaturation, giving rise to the terms "monounsaturated" and "polyunsaturated," respectively. In one embodiment, very long chain fatty acids have from 18 to 24 or more carbons. In another embodiment, very long chain fatty acids have between 18 and 24 carbon atoms.

The terms "oilseed plant" or "oil crop plant", or the like, refer to plants that produce seeds or fruit with oil content in the range of from about 1 to 2%, e.g., wheat, to about 20%, e.g., soybeans, to over 40%, e.g., sunflowers and rapeseed (canola). These include major and minor oil crops, as well as wild plant species. Exemplary oil seed or oil crop plants useful in practicing the methods disclosed herein include, but are not limited to, plants of the genera *Brassica* (e.g., rapeseed/canola (*Brassica napus*; *Brassica carinata*; *Brassica nigra*; *Brassica oleracea*), *Camelina*, *Miscanthus*, and *Jatropha*; Jojoba (*Simmondsia chinensis*), coconut; cotton; peanut; rice; safflower; sesame; soybean; mustard; wheat; flax (linseed); sunflower; olive; corn; palm; palm kernel; sugarcane; castor bean; switchgrass; *Borago officinalis*; *Echium plantagineum*; *Cuphea hookeriana*; *Cuphea pulcherrima*; *Cuphea lanceolata*; *Ricinus communis*; *Coriandrum sativum*; *Crepis alpina*; *Vernonia galamensis*; *Momordica charantia*; and *Crambe abyssinica*.

A non-limiting example of a tuber that accumulates significant amounts of reserve lipids is the tuber of *Cyperus esculentus* (chufa or tigernuts), which has been proposed as an oil crop for biofuel production. In the case of chufa, use of a constitutive or tuber-specific promoter would be useful in the methods disclosed herein.

As used herein "operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence. Similarly, "control elements compatible with expression in a subject" are those which are capable of effecting the expression of the coding sequence in that subject.

The terms "sequence homology" or "sequence similarity" are used to describe a mathematically based comparison of sequence similarities which is used to identify genes or proteins with similar functions or motifs. The nucleic acid and protein sequences of the present invention can be used as a "query sequence" to perform a search against public databases to, for example, identify other family members; related sequences, such as those containing conservative amino acid substitutions replacing corresponding amino acids in a query sequence ("sequence similarity"); or homologs.

One of ordinary skill in the art will appreciate that these sequence identity ranges are provided for guidance only; it is entirely possible that strongly significant similarity could be obtained that fall outside of the ranges provided. Nucleic acid sequences that do not show a high degree of identity can nevertheless encode similar amino acid sequences, due to the degeneracy of the genetic code. It is understood that changes in nucleic acid sequence can be made using this degeneracy to produce multiple nucleic acid molecules that all encode substantially the same protein. Means for making this adjustment are well-known to those of skill in the art. When percentage of sequence identity is used in reference to amino acid sequences it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity.

Sequence identity (or similarity) can be readily calculated by known methods, including but not limited to those described in: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Optimal alignment of sequences for comparison can be conducted, for example, by the local homology algorithm of Smith & Waterman, by the homology alignment algorithms, by the search for similarity method or, by computerized implementations of these algorithms (GAP, BESTFIT, PASTA, and TFASTA in the GCG Wisconsin Package, available from Accelrys, Inc., San Diego, Calif., United States of America), or by visual inspection. See generally, (Altschul, S. F. et al., J. Mol. Biol. 215: 403-410 (1990) and Altschul et al. Nucl. Acids Res. 25: 3389-3402 (1997)).

One example of an algorithm that is suitable for determining percent sequence identity and sequence similarity is the BLAST algorithm, which is described in (Altschul, S., et al., NCBI NLM NIH Bethesda, Md. 20894; & Altschul, S., et al., J. Mol. Biol. 215: 403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Nat'l. Acad. Sci. USA 90: 5873-5877 (1993)). One measure of similarity provided by the BLAST algorithm is the smallest sum probability (P(N)), which provides an indication of the probability by which a match between two nucleotide or amino acid sequences would occur by chance. BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, Comput. Chem., 17: 149-163 (1993)) and XNU (Claverie and States, Comput. Chem., 17: 191-201 (1993)) low-complexity filters can be employed alone or in combination.

The terms "homolog" or "homologous" refer to the relationship between two polypeptides or proteins that possess a "common evolutionary origin", including proteins from superfamilies (e.g., the immunoglobulin superfamily) in the same species of animal, as well as homologous proteins from different species of animal (for example, myosin light chain polypeptide, etc.; see Reeck et al., (1987) *Cell*, 50:667). Such proteins (and their encoding nucleic acids) have sequence homology, as reflected by their sequence similarity, whether in terms of percent identity or by the presence of specific residues or motifs and conserved positions.

Similarly, in particular embodiments of the present disclosure, two amino acid sequences are "substantially homologous" or "substantially similar" when at least 90%, 91%, 92%, 93%, 94%, 95%, 96%, 97%, 98%, or 99% of the amino acid residues are identical or represent interchangeable conservative amino acids that do not significantly adversely affect the enzymatic function exhibited by the query sequence, which in the present case is *Arabidopsis* pPLAIIIδ protein comprising the amino acid sequence encoded by *Arabidopsis* Genome Initiative Database Accession At3g63200. Two sequences are functionally identical when greater than about 95% of the amino acid residues are similar. The similar or homologous polypeptide sequences can be identified by alignment using, for example, the GCG (Genetics Computer Group, Version 7, Madison, Wis.) pileup program, or using any of the programs and algorithms described above. The program may use the local homology algorithm of Smith and Waterman with the default values: Gap creation penalty=−(1+1/k), k being the gap extension number, Average match=1, Average mismatch=−0.333.

Conservative Amino Acid Substitutions

It is well known that certain amino acids can be substituted for other amino acids in a protein structure without appreciable loss of biochemical or biological activity. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. Thus, various changes can be made in the amino acid sequences disclosed herein, or in the corresponding DNA sequences that encode these amino acid sequences, without appreciable loss of their biological utility or activity.

Polypeptides and proteins biologically functionally equivalent to *Arabidopsis* pPLAIIIδ protein comprising the amino acid sequence encoded by *Arabidopsis* Genome Initiative Database Accession At3g63200 disclosed herein include amino acid sequences containing conservative amino acid changes in the fundamental amino acid sequence. In such amino acid sequences, one or more amino acids in the fundamental sequence can be substituted, for example, with another amino acid(s), the charge and polarity of which is similar to that of the native amino acid, i.e., a conservative amino acid substitution, resulting in a silent change.

It should be noted that there are a number of different classification systems in the art that have been developed to describe the interchangeability of amino acids for one another within peptides, polypeptides, and proteins. The following discussion is merely illustrative of some of these systems, and the present disclosure encompasses any of the "conservative" amino acid changes that would be apparent to one of ordinary skill in the art of peptide, polypeptide, and protein chemistry from any of these different systems.

As disclosed in U.S. Pat. No. 5,599,686, certain amino acids in a biologically active peptide, polypeptide, or protein can be replaced by other homologous, isosteric, and/or isoelectronic amino acids, wherein the biological activity of the original molecule is conserved in the modified peptide, polypeptide, or protein. The following list of amino acid replacements is meant to be illustrative and is not limiting:

| Original Amino Acid | Replacement Amino Acid(s) |
|---|---|
| Ala | Gly |
| Arg | Lys, ornithine |
| Asn | Gln |
| Asp | Glu |
| Glu | Asp |
| Gln | Asn |
| Gly | Ala |
| Ile | Val, Leu, Met, Nle (norleucine) |
| Leu | Ile, Val, Met, Nle |

| Original Amino Acid | Replacement Amino Acid(s) |
|---|---|
| Lys | Arg |
| Met | Leu, Ile, Nle, Val |
| Phe | Tyr, Trp |
| Ser | Thr |
| Thr | Ser |
| Trp | Phe, Tyr |
| Tyr | Phe, Trp |
| Val | Leu, Ile, Met, Nle |

In another system, substitutes for an amino acid within a fundamental sequence can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine. and glutamine; (4) neutral nonpolar (hydrophobic) amino acids such as alanine, leucine, isoleucine, valine, proline, phenylalanine, tryptophan, and methionine.

Conservative amino acid changes within a fundamental peptide, polypeptide, or protein sequence can be made by substituting one amino acid within one of these groups with another amino acid within the same group.

Some of the other systems for classifying conservative amino acid interchangeability in peptides, polypeptides, and proteins applicable to the sequences of the present disclosure include, for example, the following:

1. Functionally defining common properties between individual amino acids by analyzing the normalized frequencies of amino acid changes between corresponding proteins of homologous organisms (Schulz, G. E. and R. H. Schirmer (1979) *Principles of Protein Structure* (Springer Advanced Texts in Chemistry), Springer-Verlag). According to such analyses, groups of amino acids can be defined where amino acids within a group exchange preferentially with each other, and therefore resemble each other most in their impact on overall protein structure;

2. Making amino acid changes based on the hydropathic index of amino acids as described by Kyte and Doolittle (1982) *J. Mol. Biol.* 157(1):105-32. Certain amino acids can be substituted by other amino acids having a similar hydropathic index or score and still result in a protein with similar biological activity, i.e., still obtain a biological functionally equivalent protein. In making such changes, the substitution of amino acids whose hydropathic indices are within +2 is preferred, those that are within +1 are particularly preferred, and those within +0.5 are even more particularly preferred;

3. Substitution of like amino acids on the basis of hydrophilicity. U.S. Pat. No. 4,554,101 states that the greatest local average hydrophilicity of a protein, as governed by the hydrophilicity of its adjacent amino acids, correlates with a biological property of the protein. As detailed in this patent, the following hydrophilicity values have been assigned to amino acid residues: arginine (+3.0); lysine (+3.0); aspartate (+3.0.±0.1); glutamate (+3.0.±0.1); serine (+0.3); asparagine (+0.2); glutamine (+0.2); glycine (0); threonine (−0.4); proline (−0.5.±0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

4. Betts and Russell ((2003), "Amino Acid Properties and Consequences of Substitutions", *Bioinformatics for Geneticists*, Michael R. Barnes and Ian C. Gray, Eds., John Wiley & Sons, Ltd, Chapter 14, pp. 289-316) review the nature of mutations and the properties of amino acids in a variety of different protein contexts with the purpose of aiding in anticipating and interpreting the effect that a particular amino acid change will have on protein structure and function. The authors point out that features of proteins relevant to considering amino acid mutations include cellular environments, three-dimensional structure, and evolution, as well as the classifications of amino acids based on evolutionary, chemical, and structural principles, and the role for amino acids of different classes in protein structure and function in different contexts. The authors note that classification of amino acids into categories such as those shown in FIG. 14.3 of their review, which involves common physico-chemical properties, size, affinity for water (polar and non-polar; negative or positive charge), aromaticity and aliphaticity, hydrogen-bonding ability, propensity for sharply turning regions, etc., makes it clear that reliance on simple classifications can be dangerous, and suggests that alternative amino acids could be engineered into a protein at each position. Criteria for interpreting how a particular mutation might affect protein structure and function are summarized in section 14.7 of this review, and include first inquiring about the protein, and then about the particular amino acid substitution contemplated.

Biologically/enzymatically functional equivalents of *Arabidopsis* pPLAIIIδ protein comprising the amino acid sequence encoded by *Arabidopsis* Genome Initiative Database Accession At3g63200 can have 10 or fewer conservative amino acid changes, more preferably seven or fewer conservative amino acid changes, and most preferably five or fewer conservative amino acid changes, i.e., 10, 9, 8, 7, 6, 5, 4, 3, 2, or 1 conservative amino acid changes. The encoding nucleotide sequence (e.g., gene, plasmid DNA, cDNA, codon-optimized DNA, or other synthetic DNA) will thus have corresponding base substitutions, permitting it to code for the biologically functionally equivalent form of pPLAIIIδ. Due to the degeneracy of the genetic code, i.e., the existence of more than one codon for most of the amino acids naturally occurring in proteins, other DNA (and RNA) sequences that contain essentially the same genetic information as these nucleic acids, and which encode the same amino acid sequence as that encoded by these nucleic acids, can be used in the methods disclosed herein. This principle applies as well to any of the other nucleotide sequences disclosed herein.

Industrial Uses of Fatty Acids

The methods disclosed herein permit maximizing crop value by facilitating the modulation of oil composition in plants and developing oil seed crops as biorefineries and as bioindustrial oils crop platforms using molecular techniques. Plant-produced VLCFA oils provide renewable, biodegradable, non-fossil fuel feedstocks for the production of polymers, plastics, waxes, pharmaceutical and edible/nutraceutical oils.

Very long chain fatty acids (VLCFA) containing more than 18 carbon atoms are common components of seed oils and plant waxes in a number of plant families, including the Cruciferaceae, Limnanthaceae, Simmondsiaceae, and Tropaeolaceae, and represent valuable feedstock for diverse industrial applications.

For example, erucic acid (cis-docosa-13-enoic acid, 22:1 Δ13) is the major VLCFA in the seed oil from HEAR (high erucic acid rapeseed) *B. napus* cultivars. HEAR cultivars are of great interest since C22:1 is a valuable feedstock with more than 1,000 patented industrial applications.

In the biofuels field, HEAR oil and its derivatives have been shown to possess a higher energy potential than low erucic acid oil and are therefore more suitable for biodiesel production than low erucic *Brassica* oils because the iodine value is lower in HEAR oil (i.e., lower proportion of polyunsaturated fatty acids in the oil) and within the European Union specifications.

VLCFAs are used as surface-active additives in coatings and in the production of plastic films as an anti-block or slip-promoting agent. Other applications include use as industrial feedstocks, in lubricants, detergents, photographic film-processing agents, coatings, cosmetics, pharmaceuticals, dietary supplements similar to arachidonic acid, docosahexaenoic acid, and conjugated linoleic acids, for the promotion of human and animal health.

Non-limiting examples of some of the many industrial and health-dietary supplement-related uses of VLCFA oils, including fatty acids and derivatives, fatty acid methyl esters, fatty alcohols and derivatives, and drying oils, are as follows:

Examples of Industrial Applications of Oils Highly-Enriched in VLCFAs:

Alkyd resins, Anti-block or slip-promoting agents, Biofuels and biodiesel, Biopesticides, Biopolymers from oil, Chemical feedstocks, Coatings and adhesives, Cosmetic formulations, Composite materials, Detergents and soaps, Food and feed products; dietary supplements for humans and animals, Intermediates in the production of alcohols, Lubricants, including high temperature lubricants, Industrial feedstocks, Modified epoxide gels and resins, Nylon 13,13 or Nylon 15,15, Paints, Paving bed polymers, Petroleum additives, Pharmaceutical formulations, Photographic film processing agents, Polyurethanes, plastics, and foams, Rubber, Synthetic resins, Solvents, Surface-active additives, Surfactants for enhanced oil recovery, Use in the textile, leather, and paper industries, Viscoelastic surfactants; high molecular weight anionic surfactants Use of Fatty Acids in the Pharmaceutical and Personal Hygiene Industries Fatty acids are widely used as inactive ingredients (excipients) in drug preparations, including the use of lipid formulations as carriers for active pharmaceutical substances. The largest amount of lipids used in pharmaceuticals is in the production of fat emulsions, mainly for clinical nutrition, but also as drug vehicles. Another lipid formulation is the liposome, which is a lipid carrier particle for other active ingredients. In addition, there has been an increase in the use of lipids as formulation ingredients owing to their functional effects (fatty acids have several biological effects) and their biocompatible nature. For instance, very long chain n-3 polyunsaturated fatty acids may be used as a drug to reduce plasma triacylglycerol concentration and to reduce inflammation among patients with rheumatoid arthritis. Moreover, fatty acids themselves, or as part of complex lipids, are frequently used in cosmetics such as soaps, fat emulsions, and liposomes.

Edible and Multipurpose Plant Oils

Plant (or vegetable) oils are triglycerides obtained from plants. Most, but not all vegetable oils are extracted from seeds or fruits. Edible vegetable oils are used in food, both in cooking and as supplements or "nutraceuticals". In addition, edible and other plant oils are used as biofuels, in cosmetics, for medical purposes, and various industrial purposes as noted above.

The materials and methods employed in the examples below are for illustrative purposes only, and are not intended to limit the practice of the present embodiments thereto. Any materials and methods similar or equivalent to those described herein as would be apparent to one of ordinary skill in the art can be used in the practice or testing of the present embodiments.

Example 1 pPLAIIIδ Increases Seed Oil Content

To investigate the function of pPLAIIIs in seed oil production, we isolated T-DNA insertional knockout (KO) mutants for all four pPLAIIIs (FIG. 1).

Generation of pPLAIII Knockouts, Overexpressing, and Complementation Plants

T-DNA insertional mutants for pPLAIIIα (Salk_040363), β (Salk_057212), γ (Salk_088404), and δ (Salk_029470) were identified from the Salk *Arabidopsis* T-DNA knockout collection obtained from the Ohio State University ABRC. The homozygous T-DNA insertion mutant for individual pPLAIIIs was verified by PCR-based screening using a T-DNA left border primer and gene-specific primers as listed in Table 1.

TABLE 1

PCR Primers for Mutant Screening and Molecular Cloning

| Gene | AGI | Real time PCR primers |
|---|---|---|
| pPLAIIIα | At2g39220 | Screening for T-DNA insertional mutant of Salk_040363:<br>Forward 5'-CCGAGCATCGAGACTGATAAG-3'<br>(SEQ ID NO: 1);<br>Reverse 5'-AGTATCAGCTGCTCCATCAGC-3'<br>(SEQ ID NO: 2);<br>T-DNA LB primer<br>5'-GCGTGGACCGCTTGCTGCAACT-3' (SEQ ID NO: 3) |
| pPLAIIIβ | At3g54950 | Screening for T-DNA insertional mutant of Salk_057212:<br>Forward 5'-TTGACGGATATGCAGGAACCAA-3'<br>(SEQ ID NO: 4);<br>Reverse 5'-ATGCGTGATTGCAGCCGCTGT-3'<br>(SEQ ID NO: 5);<br>T-DNA LB primer<br>5'-GCGTGGACCGCTTGCTGCAACT-3' (SEQ ID NO: 6) |
| pPLAIIIγ | At4g29800 | Screening for T-DNA insertional mutant of Salk_088404:<br>Forward 5'-GAAAGCTTCCACAATCTAACTG-3'<br>(SEQ ID NO: 7);<br>Reverse 5'-GGCGATTCGAGCGTTTGGATC-3'<br>(SEQ ID NO: 8);<br>T-DNA LB primer<br>5'-GCGTGGACCGCTTGCTGCAACT-3' (SEQ ID NO: 9) |
| pPLAIIIδ | At3g63200 | Screening for T-DNA insertional mutant of Salk_029470:<br>Forward 5'-TCGCAGTGAGAGAGCCATTTCT-3'<br>(SEQ ID NO: 10);<br>Reverse<br>5'-CAAGCAACAAATATTAGCTGCCCAAAC-3'<br>(SEQ ID NO: 11);<br>T-DNA LB primer<br>5'-GCGTGGACCGCTTGCTGCAACT-3' (SEQ ID NO: 12) |
| pPLAIIIδ | At3g63200 | Cloning of pPLAIIIδ gene into pEC291 vector for generation of complementation lines:<br>Promoter region primer<br>5'-AGGCGCGCCAAACTATCTCGTGTCGC-3'<br>(SEQ ID NO: 13);<br>Terminator region primer<br>5'-AGGCGCGCCACTCTGTGCTGGCTATC-3'<br>(SEQ ID NO: 14) |
| pPLAIIIδ | At3g63200 | Cloning of pPLAIIIδ gene into pMDC83 vector for generation of overexpression lines (35S:: pPLAIIIδ):<br>Forward<br>5'-ATTTAATTAAATGGAGATGGATCTCAGCAAGGTT-3'<br>(SEQ ID NO: 15);<br>Reverse<br>5'-ATGGCGCGCCAACGGCCGTCAGCGAGAGGGTTAA-3'<br>(SEQ ID NO: 16) |

TABLE 1-continued

PCR Primers for Mutant Screening and Molecular Cloning

| Gene | AGI | Real time PCR primers |
|---|---|---|
| pPLAIIIδ | At3g63200 | Cloning of pPLAIIIδ cDNA into pET28a vector for protein expression in E. Coli: Forward 5'-TTTGGATCCATGGAGATGGATCTCAGCAAGGTT-3' (SEQ ID NO: 17); Reverse 5'-AAGGCGGCCGCACGGCCGTCAGCGAGAGG-3' (SEQ ID NO: 18) |
| pPLAIIIδ | At3g63200 | Cloning of β-conglycinin promoter into pZY101 vector for generation of seed-specific expression lines (CON::pPLAIIIδ): Forward 5'-ATGTTTAAACAAGCTTTTGATCCATGCCCTTCAT-3' (SEQ ID NO: 19); Reverse 5'-ATTTAATTAAGCGGCCGCAGTATATCTTAAATTCT-3' (SEQ ID NO: 20) |

The isolation of pPLAIIIβ-KO was reported previously (Li et al., 2011). The loss of gene transcripts in pPLAIII-KO was confirmed by real-time PCR. To generate the complementation lines (pPLAIIIδ-COM), the genomic DNA sequence of pPLAIIIγ from the promoter region to the terminator region was cloned using two primers as listed in Table 1 and fused into a binary vector pEC291 for plant transformation.

Figure 1A:
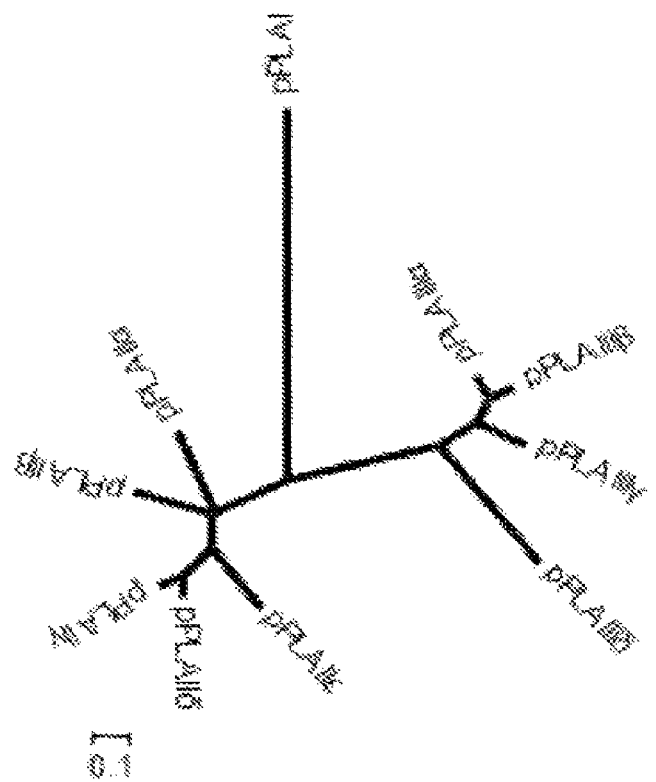
FIG. 1(A) Phylogenetic tree of the 10 patatin-related phospholipase As (pPLAs) in *Arabidopsis* generated with MEGA5 (Tamura et al., 2011). The branch lengths of the tree are proportional to divergence. The 0.1 scale represents 10% change.
Figure 1B:
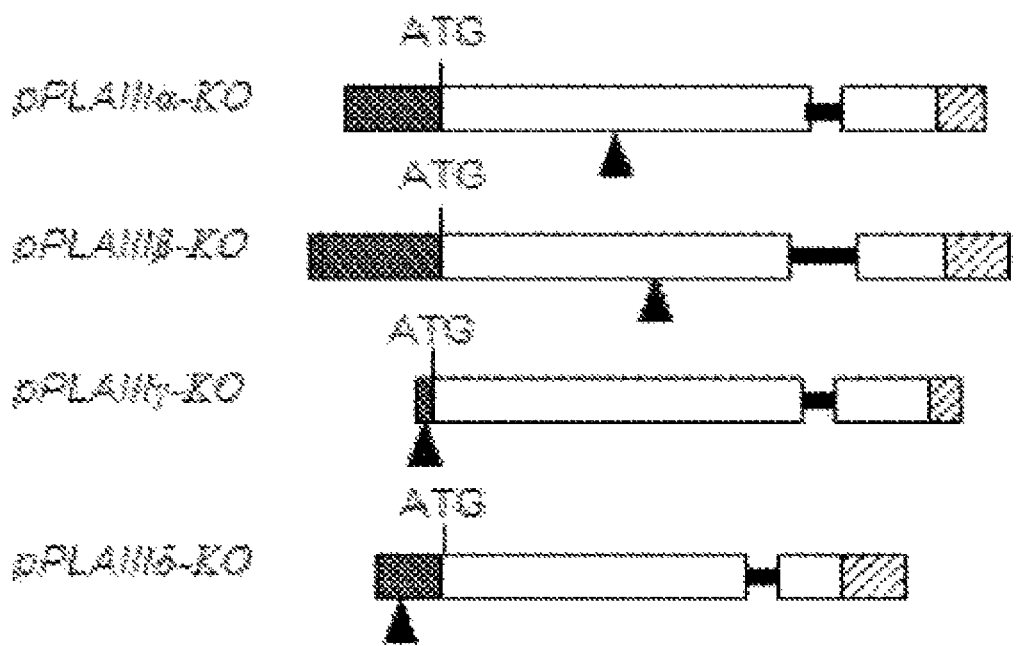
FIG. 1(B) T-DNA insertion sites in the knockout mutants of pPLAIIIα, pPLAIIIβ, pPLAIIIγ, and pPLAIIIδ. The arrowhead indicates the position of the T-DNA insertion. The filled boxes, empty boxes, and hatched boxes denote 5'-UTR (untranslated region), exons, and 3'-UTR, respectively. The bold line denotes an intron.
Figure 1C:
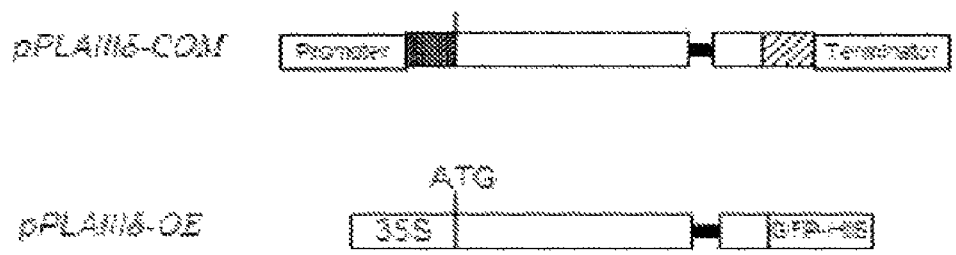
FIG. 1(C) Constructs for generating overexpression and complementation mutants of pPLAIIIδ. In the pPLAIIIδ overexpressors (pPLAIIIδ-OE), the *Arabidopsis* pPLAIIIδ gene was driven by the cauliflower mosaic virus 35S promoter and tagged on the C-terminus with green fluorescence protein and 6×Histidine. In the pPLAIIIδ complementation lines (pPLAIIIδ-COM), *Arabidopsis* pPLAIIIδ genomic DNA sequence, cloned from promoter to terminator, was transferred into T-DNA of the T-DNA insertional knockout mutant of pPLAIIIδ. The empty boxes and filled boxes denote exons and untranslated regions, respectively. Ten independent lines of pPLAIIIδ-COM were generated and they were indistinguishable from wild-type. Fifteen independent lines of pPLAIIIδ-OE were generated; plans of these OE lines were consistently smaller in plant stature than WT plants.
Figure 1C:
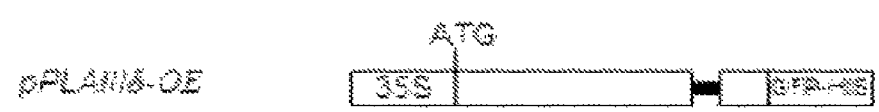
Figure 2A:
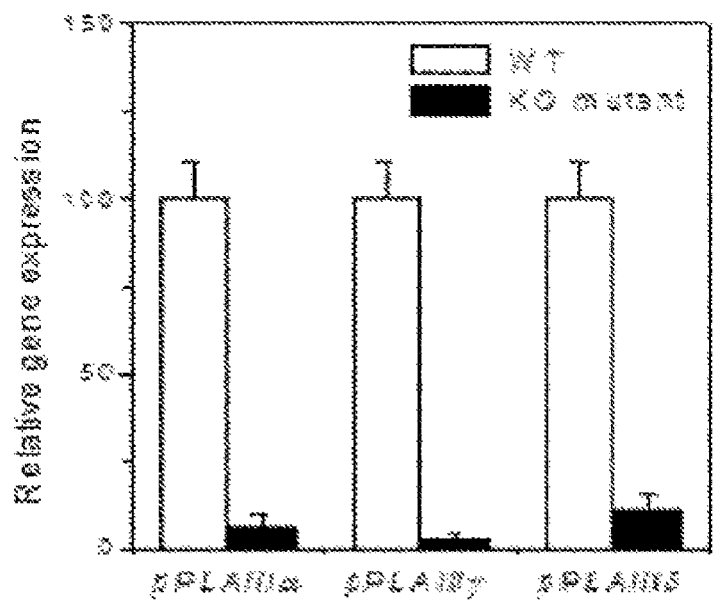
FIG. 2(A) Transcript levels of pPLAIIIα, -γ, and -δ in 2-week-old rosettes. The RNA levels were determined by real time PCR and normalized to the level of wild type. Values are means±SE (n=3).
Figure 2B:
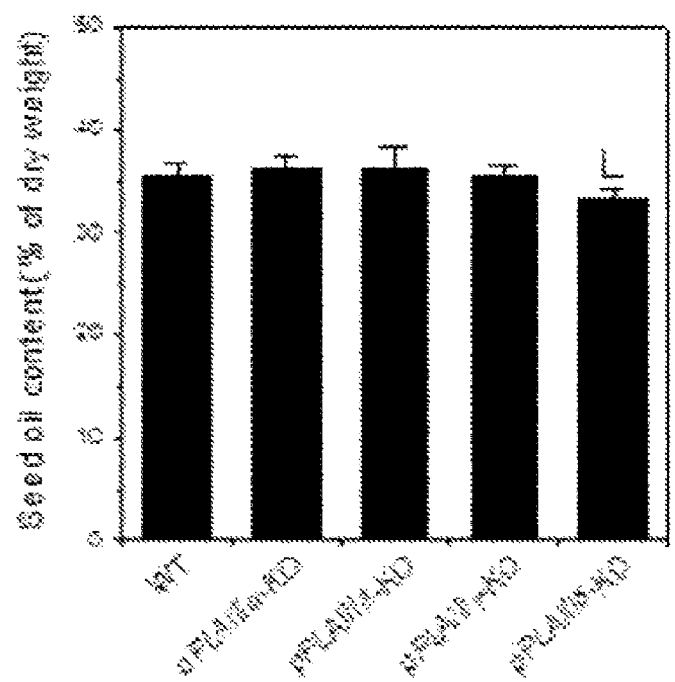
FIG. 2(B) Seed oil content in T-DNA insertion mutants of pPLAIIIα-KO, pPLAIIIβ-KO, pPLAIIIγ-KO, and pPLAIIIδ-KO. KO, knockout. Values are means±SE (n=3). $^L$Signifcantly lower at P<0.05 compared with the WT, based on Student's t test.

The T-DNA insertion sites of pPLAIIIα and pPLAIIIβ are in the first exon, while the insertion sites of pPLAIIIγ and pPLAIIIδ are located in the 5'-UTR region (FIG. 1B). All of these insertional mutants have a negligible level of transcript as measured by real-time PCR of pPLAIIIα, pPLAIIIγ, and pPLAIIIδ (FIG. 2A). The loss of pPLAIIIβ expression in pPLAIIIβ-KO was described previously (Li et al., 2011). However, only the pPLAIIIδ-KO seeds, not the other pPLAIIIs, displayed a significant change in oil content compared to WT seeds; the oil contents of pPLAIIIδ-KO and WT seeds were 33% and 35.5% of the seed weight, respectively (FIG. 2B). To confirm the effect of pPLAIIIδ on seed oil production, we genetically complemented the KO by transferring pPLAIIIδ with its native promoter and terminator sequences into the KO mutant (designated as COM; FIG. 1C). Expression of pPLAIIIδ in the COM lines was restored to the WT level (FIG. 2C), and the oil content in COM seeds was the same as that of WT (FIG. 2D).

Analysis of mRNA accumulation patterns for pPLAIIIs in seeds indicate that pPLAIIIα, β, and γ were expressed in tissues that do not accumulate large amounts of TAG in developing seeds (see Supplemental FIG. 2 of Li et al. (May, 2013) Plant Physiology 162:39-51). In mature green seeds, pPLAIIIγ was expressed mostly in seed coat, pPLAIIIβ mostly in chalazal seed coat, and pPLAIIIα mostly in seed coats and peripheral endosperm (see Supplemental FIG. 2 of Li et al., supra).

In contrast, pPLAIIIδ was expressed in developing radicle and in cotyledons, the major storage tissue for seed oil in Arabidopsis (see Supplemental FIG. 2F of Li et al., supra). As noted above, Huang et al. (2001) did not report any data on pPLAIIIδ expression in seeds.

The mRNA accumulation pattern of the pPLAIII genes is consistent with a pPLAIIIδ-specific effect on seed oil content and, thus, further analysis was focused on pPLAIIIδ.

To further investigate pPLAIIIδ function, we produced multiple overexpressing (OE) Arabidopsis lines by placing pPLAIIIδ under the control of cauliflower mosaic virus 35S promoter (35S::pPLAIIIδ-OE; FIG. 1C).

To overexpress pPLAIIIδ, the genomic sequence of pPLAIIIδ was obtained by PCR using Col-0 Arabidopsis genomic DNA as a template and primers listed in Table 1. The genomic DNA was cloned into the pMDC83 vector before the GFP-His coding sequence. The expression of pPLAIIIδ was under the control of the 35S cauliflower mosaic virus promoter or the promoter of soybean β-conglycinin. The sequences of the fusion constructs were verified by sequencing before they were introduced into the Agrobacterium tumefaciens strain C58C1. Col-0 Arabidopsis plants were transformed, and transgenic plants were screened and confirmed by antibiotic selection and PCR. Over 15 independent transgenic lines were obtained (pPLAIIIδ-OE) with similar plant stature. Five independent lines of pPLAIIIδ-OE were further verified by immunoblotting with anti-GFP antibody.

RNA Extraction and Real-Time PCR

Real-time PCR was performed as described previously (Li et al., 2006; 2011). The real time PCR primers are listed in Table 2. Briefly, total RNA was extracted from different tissues using the cetyl-trimethylammonium bromide method (Stewart and Via, 1993). DNA contamination in RNA samples was removed with RNase-free DNase. An iScript kit (Bio-Rad) was used to synthesize cDNA from isolated RNA template by reverse transcription. The MyiQ sequence detection system (Bio-Rad) was used to detect products during quantitative real-time PCR by monitoring SYBR green fluorescent labeling of double-stranded DNA. Efficiency was normalized to a control gene UBQ10. The data were expressed as mean±SE (n=3 replicates). PCR conditions were as follows: one cycle of 95° C. for 1 min; 40 cycles of DNA melting at 95° C. for 30 s, DNA annealing at 55° C. for 30 s, and DNA extension at 72° C. for 30 s; and final extension of DNA at 72° C. for 10 min.

TABLE 2

Real time PCR Primers for Quantitative Measurement of Transcript Levels

| Gene | AGI | Real time PCR primers |
|---|---|---|
| AAPT1 | At1g13560 | Forward 5'-GCCCTTGGAATCTACTGCTT-3' (SEQ ID NO: 21); Reverse 5'-ACATAACTTCACCTATCCTG-3' (SEQ ID NO: 22) |
| AAPT2 | At3g25585 | Forward 5'-CGAACCAAAAGGATTGAAAA-3' (SEQ ID NO: 23); Reverse 5'-TCCACAAGAGGAACCCCGTC-3' (SEQ ID NO: 24) |
| CCT1 | At2g32260 | Forward 5'-GCCACTTCTACTAAACTCCC-3' (SEQ ID NO: 25); Reverse 5'-CACACACAAACAAACACATC-3' (SEQ ID NO: 26) |
| CCT2 | At4g15130 | Forward 5'-CTGACGATTTCCAAAGACAA-3' (SEQ ID NO: 27); Reverse 5'-TTCAATCCCTTTGTTGCTCA-3' (SEQ ID NO: 28) |
| DGAT1 | At2g19450 | Forward 5'-GGTTCATCTTCTGCATTTTCGGA-3' (SEQ ID NO: 29); Reverse 5'-TTTTCGGTTCATCAGGTCGTGGT-3' (SEQ ID NO: 30) |
| DGAT2 | At3g51520 | Forward 5'-TGTTTGAGAGGCACAAGTCCCGA-3' (SEQ ID NO: 31); Reverse 5'-AGTCCAAATCCAGCTCCAAGGTA-3' (SEQ ID NO: 32) |
| GPAT | At1g32200 | Forward 5'-CAAGTCGGTGAATGAACAATACG-3' (SEQ ID NO: 33); Reverse 5'-TGATTGTGTTTGTGTATCCCTAA-3' (SEQ ID NO: 34) |
| LPAT2 | At3g57650 | Forward 5'-CAAGAACAGAACATTGGCCGTCC-3' (SEQ ID NO: 35); Reverse 5'-GCCCAGTGTAGGAACTTTATTGC-3' (SEQ ID NO: 36) |
| LPAT3 | At1g51260 | Forward 5'-ATTTATCACCAAGGATGCTCAAC-3' (SEQ ID NO: 37); Reverse 5'-TGAAACCACCGAATACAAGGAAA-3' (SEQ ID NO: 38) |
| LPAT4 | At1g75020 | Forward 5'-CGTTCGGCGAGTTCTACTAAAGG-3' (SEQ ID NO: 39); Reverse 5'-TCTTCTTCTGGTCTTTGATTGGG-3' (SEQ ID NO: 40) |
| LPAT5 | At3g18850 | Forward 5'-GATTGCCTTCACCACCATCTGTA-3' (SEQ ID NO: 41); Reverse 5'-AGCAGAGGTCAAGTAGACACAGG-3' (SEQ ID NO: 42) |
| LPCAT1 | At1g63050 | Forward 5'-TGCGGTTCAGATTCCGCTTTTCT-3' (SEQ ID NO: 43); Reverse 5'-GTTGCCACCGGTAAATAGCTTTCG-3' (SEQ ID NO: 44) |
| PAH1 | At3g09560 | Forward 5'-ACCCGTTCTATGCCGGATTTGG-3' (SEQ ID NO: 45); Reverse 5'-TCCTGTTGCCACTTCTCCCTTTG-3' (SEQ ID NO: 46) |
| PDAT1 | At5g13640 | Forward 5'-GGAGTGGGGATACCAACGGAACG-3' (SEQ ID NO: 47); Reverse 5'-GAAAGGGGATGCAACTGTCGGGA-3' (SEQ ID NO: 48) |
| pPLAIIIα | At2g39220 | Forward 5'-GTAGCAGAGGAGATGCTGAAGCAGAA-3' (SEQ ID NO: 49); Reverse 5'-TACAGTGGGAGCGATTCTACAACTCC-3' (SEQ ID NO: 50) |

TABLE 2-continued

Real time PCR Primers for Quantitative Measurement of Transcript Levels

| Gene | AGI | Real time PCR primers |
|---|---|---|
| pPLAIIIγ | At4g29800 | Forward 5'-CACGGATCCAAGAGCAGAGAATGTGA-3' (SEQ ID NO: 51); Reverse 5'-CTAACACTTCGTCGCTGCTGCTCAAT-3' (SEQ ID NO: 52) |
| pPLAIIIδ | At3g63200 | Forward 5'-CAACGTCTTGTTGCGTCAGGAAAGTC-3' (SEQ ID NO: 53); Reverse 5'-ATTAACTCGAAGATGCTGGCTGGG-3' (SEQ ID NO: 54) |
| UBQ10 | At4g05320 | Forward 5'-CACACTCCACTTGGTCTTGCGT-3' (SEQ ID NO: 55); Reverse 5'-TGGTCTTTCCGGTGAGAGTCTTCA-3' (SEQ ID NO: 56) |

Figure 2C:
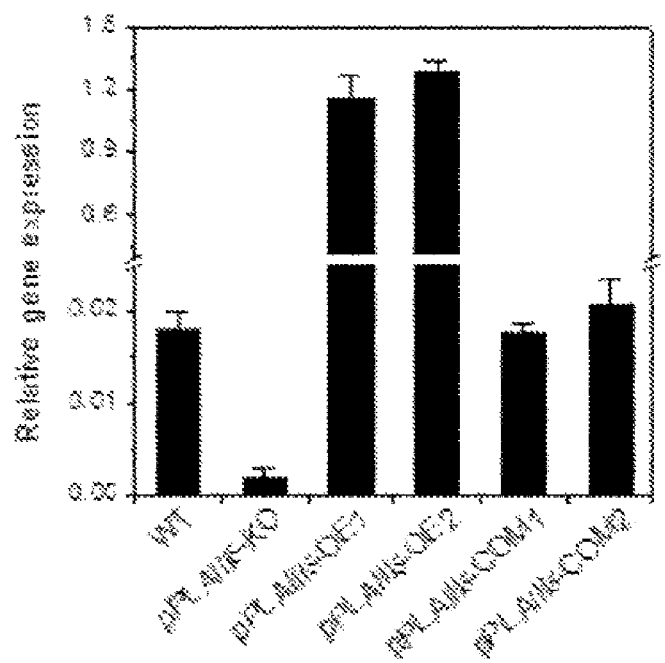
FIG. 2(C) Transcript levels of pPLAIIIδ in WT, pPLAIIIδ-KO, OE, and COM plants. pPLAIIIδ-OE1, -2 and pPLAIIIδ-COM1, -2 are two independent lines of T3 generation of pPLAIIIδ-OE and pPLAIIIδ-COM. The RNA levels were determined by real time PCR and normalized in comparison to UBQ10. Values are means±SE (n=3).
Figure 2D:
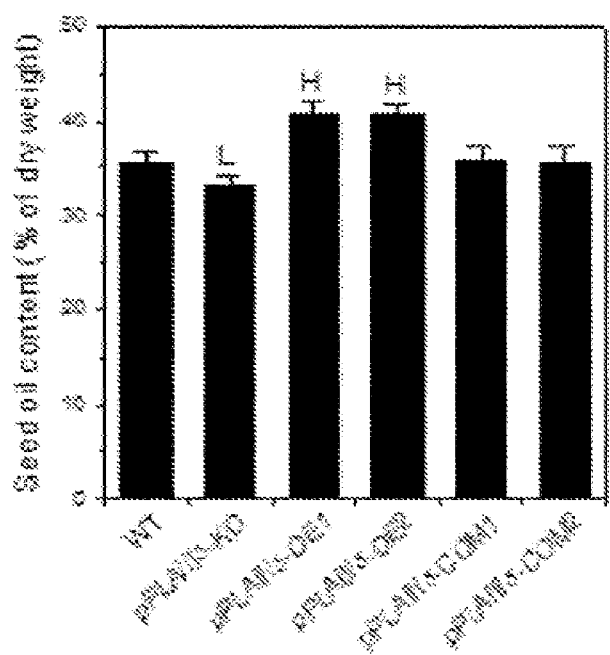
FIG. 2(D) Seed oil content in pPLAIIIδ-OE and pPLAIIIδ-COM T3 seeds. pPLAIIIδ expression in OE lines was under the control of the cauliflower mosaic virus 35S promoter, while in the COM lines, it was under the control of its own promoter. Values are means±SE (n=3). $^H$Significantly higher and $^L$Signifcantly lower, each at P<0.05 compared with the WT, based on Student's t test.
Figure 2E:
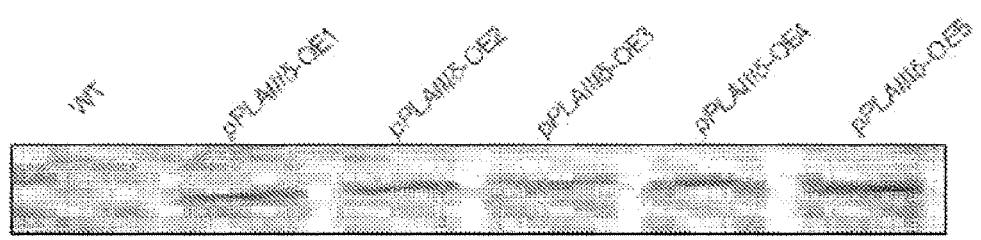
FIG. 2(E) Immunoblotting of GFP-tagged pPLAIIIδ in *Arabidopsis*. Leaf proteins extracted from plants were separated by 8% SDS-PAGE and transferred to a polyvinylidene difluoride membrane and visualized with alkaline phosphatase conjugated to a secondary anti-mouse antibody after blotting with GFP antibody. Five independent T3 lines of pPLAIIIδ-OE mutants were examined.

The mRNA level of pPLAIIIδ was increased substantially in OE over WT plants (FIG. 2C). The presence of the introduced green fluorescence protein (GFP) tagged pPLAIIIδ was detected by immunoblotting with a GFP antibody (FIG. 2E). Seed oil content in two OE lines was approximately 40.5%, which was 5% higher than that of WT (35.5%; FIG. 2D).

Taken together, these data indicate that pPLAIIIδ plays a positive role in seed oil accumulation.

Example 2 pPLAIIIδ Increases 20-Carbon Fatty Acid Content at the Expense of 18-Carbon Fatty Acids The effect of pPLAIIIδ on 18C and 20C fatty acid content in seeds was determined as follows.

Analysis of Fatty Acid Composition and Oil Content

Ten milligrams of Arabidopsis seeds were placed in glass tubes with Teflon-lined screw caps and 1.5 mL 5% (v/v) $H_2SO_4$ in methanol with 0.2% butylated hydroxytoluene was added. The samples were incubated for 1 h at 90° C. for oil extraction and transmethylation. Fatty acid methyl esters (FAMEs) were extracted with hexane. FAMEs were quantified using gas chromatography on a SUPELCOWAX-10 (0.25 mm×30 m) column with helium as a carrier gas at 20 mL/min and detection by flame ionization. The oven temperature was maintained at 170° C. for 1 min and then ramped to 210° C. at 3° C. per min. FAMEs from TAG were identified by comparing their retention times FAMEs in a standard mixture. Heptadecanoic acid (17:0) was used as the internal standard to quantify the amounts of individual fatty acids. Fatty acid composition is expressed in weight percentage.

FIG. 3A shows that the fatty acid composition was significantly altered in pPLAIIIδ-KO and 35S::pPLAIIIδ-OE seeds. The levels of 18 carbon-fatty acids tended to increase in KO and decrease in OE seeds compared to WT seeds. For example, 18:1 was increased by 10% in KO but decreased 6% in OE1. Conversely, the amounts of 20-carbon fatty acids 20:0 and 20:2 were decreased by 12% and 12% in KO, while 20:0 and 20:1 were increased by 12% and 15% in OE lines, compared to WT. The 22-carbon species, 22:1, showed a trend similar to the 20-carbon species. The ratio of 20- to 18-carbon fatty acids was decreased by 10% in KO and increased by 19% in OE compared with WT (FIG. 3B). The fatty acid composition in COM seeds was similar to that of WT seeds (FIG. 3B). Thus, increased mRNA level of pPLAIIIδ promoted accumulation of longer chain fatty acids at the expense of 18-carbon fatty acids, 18:1 and 18:2, whereas pPLAIIIδ KO decreased the production of longer chains with increased accumulation of 18-carbon fatty acids.

Fatty acids in Arabidopsis seeds occur primarily in esterified form in TAGs. TAGs include many different molecular species with varied carbon chain length and degrees of unsaturation in the three acyl chains. Three acyl chains in TAG are not randomly distributed. Since pPLAIIIδ affects 18:1 and 20:1 acuumulation in TAG, we wondered if pPLAIIIδ alters the distribution of three acyl chains and thus produces some unique TAG molecule species. We therefore analyzed the TAG species in WT, KO, and OE seeds by electrospray ionization-tandem mass spectrometry.

Analysis of TAG Species in WT, KO, and OE Seeds by Electrospray Ionization-Tandem Mass Spectrometry An automated, direct-infusion electrospray ionization-tandem mass spectrometry approach was used for TAG analysis. A precise amount of internal standard (0.5 nmol tri17:1-TAG, Avanti Polar Lipids) was added to around 25 mg of dry Arabidopsis seeds, which were ground with mortar and pestle in 1.0 mL of chloroform/methanol (2:1). The mixture were extracted with shaking for 1 h at room temperature and centrifuged to pellet the debris. Fifty microliters of the supernatant were combined with 310 µL chloroform, and 840 µL of chloroform/methanol/300 mM ammonium acetate in water (300:665:35). The final volume was 1.2 mL.

Unfractionated lipid extracts were introduced by continuous infusion into the ESI source on a triple quadruple MS (API4000, Applied Biosystems, Foster City, Calif.). Samples were introduced using an autosampler (LC Mini PAL, CTC Analytics AG, Zwingen, Switzerland) fitted with the required injection loop for the acquisition time and presented to the ESI needle at 30 l/min. TAGs were detected by a series of neutral loss scans that detected TAG species as $[M+NH_4]^+$ ions. The scans targeted losses of various fatty acids as neutral ammoniated fragments: NL 285.2 (17:1, for the TAG internal standard); NL 273.2 (16:0); NL 301.2 (18:0); NL 299.2 (18:1); NL 297.2 (18:2); NL 295.2 (18:3); NL 329.2 (20:0); NL 327.2 (20:1); NL 325.2 (20:2); NL 357.2 (22:0); NL 355.2 (22:1). The scan speed was 100u per sec. The collision energy, with nitrogen in the collision cell, was +20 V, declustering potential was +100 V, entrance potential was +14 V, and exit potential was +14 V. Sixty continuum scans were averaged in MCA mode (multiple channel analyzers).

For all analyses the collision gas pressure was set on "low", and the mass analyzers were adjusted to a resolution of 0.7u full width at half height. The source temperature (heated nebulizer) was 100° C., the interface heater was on, +5.5 kV was applied to the electrospray capillary, the curtain gas was set at 20 (arbitrary units), and the two ion source gases were set at 45 (arbitrary units).

For TAG analyses, the background of each spectrum was subtracted, the data were smoothed, and peak areas integrated using a custom script and Applied Biosystems Analyst software. Peaks corresponding to the target lipids in these spectra were identified, and the data were corrected for A+2 isotopic overlap (based on the m/z of the charged fragments) within each spectra. Signals were also corrected for isotopic overlap across spectra, based on the A+2 overlaps and masses of the neutral fragments. All signals for each sample were normalized to the signal of the internal standard. A sample containing internal standard alone, run through the same series of scans, was used to correct for chemical or instrumental noise: amounts of each target lipid detected in the "internal standards-only" sample were subtracted from the molar amounts of each target lipid calculated from the plant lipid spectra. The "internal standards-only" spectra were used to correct the data from the following five samples run on the instrument.

The corrected data from all fatty acyl (NL) scans for each TAG species, as defined by m/z, which corresponds to total acyl carbons: total double bonds (e.g. 52:3), were used to calculate the amount of each individual TAG species. As described by Han and Gross, formulas were developed to assign particular signals from the NL scans to particular TAGs (Han and Gross, 2001). Once values for all TAGs were calculated, the amount of each TAG was expressed as a percentage of the total values for all TAG species. Because there is variation in ionization efficiency among acyl glycerol species with different fatty acyl groups (Han and Gross, 2001) and, here, no response factors for individual species were determined, the values are not directly proportional to the TAG content of each species. However, the amounts of particular TAG species can be meaningfully compared across samples.

The major fatty acyl chain carbon numbers (C) in seed TAGs are 16C, 18C, and 20C, and the major TAG species have total C of C50 (e.g., 16-16-18), C52 (e.g., 16-18-18), C54 (e.g., 18-18-18), C56 (e.g., 18-18-20), C58 (e.g., 18-20-20), and C60 (e.g., 20-20-20) (FIG. 4). The percentages of C50, C52, and C54 TAG species in total TAGs, as indicated by their relative mass spectral signals, tended to be higher in KO while lower in OE mutants when compared with WT, while the levels of C56, C58, and C60 TAG species were changed in the opposite manner in KO and OE lines of pPLAIIIδ (FIG. 4 and FIG. 5). For example, the percentages of some 16C and 18C-containing TAGs (16:0-16:0-18:3, 16:0-18:1-18:3, 18:2-18:2-18:3) were significantly lower in OE mutants than in WT (FIG. 4A). While certain TAG species could not be quantified individually and thus their compositional percentages were expressed in combination, the percentages of 20C-containing TAGs and TAG groups tended to be or were significantly lower in KO and higher in OE mutants compared with WT (FIG. 4A).

Overall, the relative amounts of C50, C52, and C54 TAGs tended to be lower, while the amounts of C56, C58, and C60 TAGs tended to be higher in OE mutant seeds compared to WT (FIG. 4B). Measurement of 113 additional TAG species and 8 TAG species groups confirmed the trend for the percentages of 18C-containing TAGs to be lower and the 20C-containing TAGs to be higher in OEs compared with WT (FIG. 5A-E).

Taken together, these data indicate that pPLAIIIδ promotes the accumulation of 20C-containing TAG species.

Example 3 pPLAIIIδ-OE Increases the Transcript Levels of Genes in TAG and PC Synthesis

To gain insight into how pPLAIIIδ facilitates TAG accumulation and modification, we measured the mRNA levels of selected genes in TAG and PC synthesis and metabolism in developing *Arabidopsis* siliques (FIG. 6).

RNA Extraction and Real-Time PCR

Real-time PCR was performed as described previously (Li et al., 2006; 2011). Briefly, total RNA was extracted from different tissues using the cetyl-trimethylammonium bromide method (Stewart and Via, 1993). DNA contamination in RNA samples was removed with RNase-free DNase. An iScript kit (Bio-Rad) was used to synthesize cDNA from isolated RNA template by reverse transcription. The MyiQ sequence detection system (Bio-Rad) was used to detect products during quantitative real-time PCR by monitoring SYBR green fluorescent labeling of double-stranded DNA. Efficiency was normalized to a control gene UBQ10. The real time PCR primers are listed in Table 2 in Example 1. The data were expressed as mean±SE (n=3 replicates). PCR conditions were as follows: one cycle of 95° C. for 1 min; 40 cycles of DNA melting at 95° C. for 30 s, DNA annealing at 55° C. for 30 s, and DNA extension at 72° C. for 30 s; and final extension of DNA at 72° C. for 10 min.

In the Kennedy pathway of TAG biosynthesis, glycerol-3-phosphate (G3P) is sequentially acylated by glycerol phosphate acyltransferase (GPAT) and lysophosphatidic acid acyltransferase (LPAT), followed by PA phosphohydrolase (PAH) and diacylglycerol acyltransferase (DGAT). The transcript levels for the genes in the Kennedy pathway, including GPAT, LPAT2, LPAT3, PAH, and DGAT1 were increased two to five-fold in pPLAIIIδ-OE lines (FIG. 6A). By comparison, mRNA levels of both DGAT2 and LPAT5 were the same in WT, pPLAIIIδ-KO, and 35S::pPLAIIIδ-OE siliques (FIG. 6). Phospholipid:diacylglycerol acyltransferase (PDAT) catalyzes the transfer of a fatty acid from PC to diacylglycerol (DAG) to produce TAG. The mRNA level of PDAT1 was increased by almost three fold in OE lines compared to WT (FIG. 6B).

In the Kennedy pathway of PC biosynthesis, choline phosphate:CTP cytidylyltransferase (CCT) synthesizes CDP-choline using CTP and phosphocholine, and aminoalcohol-phosphotransferase (AAPT) catalyzes the last step of PC synthesis by transferring phosphocholine to DAG from CDP-choline. There are two CCTs and AAPTs in *Arabidopsis*. Compared to WT, the mRNA levels of CCT2 and AAPT1 were increased almost by ten-fold, whereas the increase in CCT1 and AAPT2 was about two-fold in pPLAIIIγ-OE siliques (FIG. 6B). The mRNA abundance of LPC:acyl-CoA acyltransferase (LPCAT1) was also increased 3-fold in OE lines (FIG. 6B).

These data demonstrate that pPLAIIIγ overexpression increases the mRNA level of genes involved TAG and PC synthesis. On the other hand, in KO siliques, the mRNA level for the lipid-metabolizing genes was not significantly different from that of WT, even though the mRNA level for several of these genes tended to be lower than that of WT (FIG. 6), These results suggest that the loss of pPLAIIIγ may be partially compensated for by other members of pPLAs.

Example 4 pPLAIIIγ Hydrolyzes Phosphatidylcholine and Acyl-CoA and Affects Acyl-CoA Levels in *Arabidopsis* pPLAIIIγ is more distantly related to the other three pPLAIIIγ than they are to each other (FIG. 1A). pPLAIIIγ has an aspartic acid (D) in the DGG catalytic dyad motif, similar to pPLAs in the other groups, whereas in pPLAIIIβ and pPLAIIIγ the aspartic acid is replaced by glycine (G) (Li et al., 2011).

To determine the enzymatic function of pPLAIIIγ, we expressed 6×His-tagged pPLAIIIγ in *E. coli* and purified it to near homogeneity (FIG. 7A). The PC (phosphatidylcholine)-hydrolyzing activity of pPLAIIIγ was examined because PC is the most abundant phospholipid and serves as a key intermediate for TAG synthesis.

pPLAIIIδ Cloning and Protein Purification from *Escherichia coli*

The full-length cDNA of pPLAIIIγ was obtained by PCR using an *Arabidopsis thaliana* cDNA library as a template and a pair of primers listed in Table 1. The cDNA was cloned into the pET28a vector before the 6×His coding sequence. The 6×His fusion construct was sequenced and confirmed to be error free before it was introduced into *E. coli* strain Rosetta (DE3) (Amersham Biosciences). The bacteria were grown to an $OD_{600}$ of 0.7 and induced with 0.1 mM isopropyl 1-thio-β-D-galactopyranoside for 16 h at 16° C. The pPLAIIIγ-6×His fusion protein was purified as described previously (Pappan et al., 2004). Briefly, the bacterial pellet was resuspended in STE buffer containing 1 mg/mL lysozyme (50 mM Tris-HCl, pH 8.0, 150 mM NaCl, and 1 mM EDTA). The samples were kept on ice for 30 min. DTT and N-laurylsarcosine (Sarkosyl) were added to a final concentration of 5 mM and 1.5% (w/v), respectively. The suspension was vortexed and sonicated on ice for 5 min. After centrifugation at 10,000 g for 20 min, the supernatant was transferred to a new tube. Triton X-100 was added to a final concentration of 4% (v/v) and 6×His agarose beads were added (10%, w/v). The solution was gently rotated at 25° C. for 1 h. The fusion proteins bound to agarose beads were washed with 20 volumes of STE buffer. The amount of purified protein was measured with a protein assay kit (Bio-Rad).

Enzyme Assays

Phospholipids and acyl-CoAs were purchased from Avanti Polar Lipids. PC or 18:3-CoA in chloroform was dried under a nitrogen stream and emulsified in reaction buffer (25 mM HEPES, pH 7.5, 10 mM $CaCl_2$, and 10 mM $MgCl_2$) by vortexing, followed by 5 min sonication on ice. Acyl hydrolyzing activities were assayed in a reaction mixture containing 25 mM HEPES, pH 7.5, 10 mM $CaCl_2$, 10 mM $MgCl_2$, and 60 μmol PC as substrate. Ten micrograms of purified protein was added to the mixture in a final volume of 500 μL. The reaction was incubated at 30° C. for indicated minutes, and stopped by adding 2 mL of chloroform/methanol (2:1, v/v) and 500 μL 25 mM LiCl. After vortexing and separation by centrifugation, the lower phase was transferred to a new glass tube. The upper phase was extracted twice more by adding 1 mL of chloroform each time, and the three lower phases were combined. Lipid internal standards were added, and lipid quantification was performed by mass spectrometry as described below.

Lipid Quantification

In in vitro enzyme assays, lipids were extracted for analysis as previously described (Li et al., 2011). Twenty microliters of lipid sample were combined with 340 μL chloroform, and 840 μL of chloroform/methanol/300 mM ammonium acetate in water (300:665:35). FFAs were determined by ESI-MS on a electrospray ionization triple quadruple mass spectrometer (API4000, Applied Biosystems), using the deuterated internal standard (7,7,8,8-d4-16:0 fatty acid) (Sigma-Aldrich), by scanning in negative ion mode from m/z 200 to m/z 350 (Li et al., 2011). LPC was determined with the same instrument as previously described (Li et al., 2011). Plants for acyl-CoA measurement were grown in growth chambers with a 12 h-light/12 h-dark cycle, at 23/21° C., 50% humidity, at 200 μmol $m^{-2}$ $s^{-1}$ of light intensity, and watered with fertilizer once a week. Acyl-CoAs were extracted and analyzed by LC-ESI-MS/MS as described previously (Magnes et al., 2005; Han et al., 2010). TAG molecular species were analyzed by ESI-MS/MS using neutral loss scan modes (Lee et al., 2011; 2012). The TAG analysis is described in detail in Example 2.

Incubation of pPLAIIIδ with 16:0-18:2-PC resulted in the production of free fatty acid (FFA) and LPC. pPLAIIIδ hydrolysis at the sn-1 position produces 16:0-FFA and 18:2-LPC (FIG. 7B) whereas pPLAIIIδ hydrolysis at the sn-2 position produces 18:2-FFA and 16:0-LPC (FIG. 7C). The production of 18:2-FFA was approximately five-fold more than that of 16:0-FFA, and correspondingly much more 16:0-LPC was formed than 18:2-LPC.

These data indicate that pPLAIIIδ hydrolyzes PC at both sn-1 and sn-2 positions and that pPLAIIIδ preferentially releases 18:2 from the sn-2 position.

In addition, we determined whether pPLAIIIδ could hydrolyze acyl-CoA because our previous study showed that another pPLAIII member, pPLAIIIβ, has thioesterase activity (Li et al., 2011).

Incubation of pPLAIIIδ with 18:3-CoA resulted in the steady production of 18:3-FFA with increasing reaction time (FIG. 8A), indicating that pPLAIIIδ possesses a thioesterase activity. We then determined whether the alterations of pPLAIIIδ expression impacted the acyl-CoA content in *Arabidopsis*. In siliques that included developing seeds with active storage lipid biosynthesis, the level of total acyl-CoA was 19% higher in KO and 18% lower in OE mutants than in WT (FIG. 8B). The major acyl-CoA species are 18:3-CoA and 18:2-CoA, followed by 16:0-CoA. The levels of 18:1-CoA, 18:2-CoA and 18:3-CoA were significantly higher in KO and 16:0-CoA and 18:2-CoA were significantly lower in OE than in WT siliques (FIG. 8C).

The data are consistent with pPLAIIIδ functioning as an acyl-CoA thioesterase activity in vivo.

Example 5 pPLAIIIδ is Associated with the Plasma and Intracellular Membranes

To determine its subcellular association, a GFP-tagged pPLAIIIδ was expressed in *Arabidopsis*, and the location of the green fluorescence signal of pPLAIIIδ-GFP was determined.

Microscopy Imaging and Subcellular Fractionation

The subcellular location of GFP-tagged protein was determined using a Zeiss LSM 510 confocal microscope equipped with a X40 differential interference contrast, 1.2-numerical aperture water immersion lens, with excitation using the 488 nm line of an argon gas laser and a 500-550 nm band pass emission filter. Plasmolysis in primary root cells was induced by immersing roots in 0.5 M NaCl for 1, 3, and 5 min. Developing seeds from *Arabidopsis* siliques were imaged using a Nikon Eclipse 800 widefield microscope and a X60 differential interference contrast, 1.2-numerical aperture objective, with mercury lamp excitation and a 492/18 BP excitation filter and a 535/40 B emission filter. For subcellular fractionation, proteins were extracted from leaves of 4-week-old plants using buffer (30 mM HEPES, pH 7.5, 400 mM NaCl, and 1 mM phenylmethanesulfonyl fluoride), followed by centrifugation at 6,000 g for 10 min. The supernatant was centrifuged at 100,000 g for 60 min. The resultant supernatant is referred to as the soluble cytosol fraction, and the pellet is referred to as the microsomal fraction. The microsomal fraction was separated further into the plasma and intracellular membrane fractions, using two-phase partitioning as described previously (Fan et al., 1999).

SDS-PAGE and Immunoblotting

Leaf samples, each weighing approximately 1 g, were harvested and ground in 3 mL buffer of 30 mM HEPES, pH 7.5, 400 mM NaCl, 1.0 mM phenylmethanesulfonyl fluoride, 1 mM dithiothreitol. Proteins were separated by 8% SDS-PAGE and transferred to a polyvinylidene difluoride membrane. The membrane was visualized with alkaline phosphatase conjugated to a secondary anti-mouse antibody after blotting with GFP antibody.

The green fluorescence signal of pPLAIIIδ-GFP was mostly detected on the inner cell boundary of leaf epidermal cells (see FIG. 7A at page 46 of Li et al. (May, 2013) Plant Physiology 162:39-51 for the color photographs). Plasmolysis by applying saline solution to the roots showed that the GFP signal in root epidermal cells was shrinking along with the plasma membrane (see FIG. 7B in Li et al., supra).

To further analyze the intracellular association, total leaf proteins were fractionated into cytosolic and microsomal fractions. All pPLAIIIδ-GFP was associated with the microsomal membranes but not cytosol (see FIG. 7C in Li et al., supra). The microsomal proteins were further partitioned into the plasma membrane and intracellular membrane fractions. Approximately 80% pPLAIIIδ-GFP was associated with the plasma membrane whereas 20% was associated with intracellular membranes based on the intensity of the protein bands (see FIG. 7C in Li et al., supra).

These data indicate pPLAIIIδ is associated with both the plasma and intracellular membranes.

Example 6

Seed-Specific Overexpression of pPLAIIIδ Increases Oil Content

The increased oil content in seeds raises the question of whether increased pPLAIIIδ expression can be used to increase seed oil production as constitutive overexpression of pPLAIIIδ resulted in a decrease in plant height and overall seed yield (FIGS. 9A and 9B). The seed yield per 35S::pPLAIIIδ-OE plants was approximately 50% of that of WT plants (FIG. 9B).

To explore whether the improved oil content could be uncoupled from decreased seed production, we placed pPLAIIIδ under the control of the seed-specific promoter of soybean β-conglycinin (CON::pPLAIIIδ; FIG. 10A).

FIG. 10A shows constructs for generating seed specific expression mutants of pPLAIIIδ. *Arabidopsis* pPLAIIIδ genomic DNA cloned from start codon to stop codon (stop codon removed) was driven by soybean β-conglycinin promoter and tagged on C-terminus by green fluorescence protein and 6×Histidine. The resulting transgenic *Arabidopsis* were designated as CON::pPLAIIIδ. Ten independent lines of T3 generation mutants were obtained. The growth of the CON::pPLAIIIδ mutants was comparable with that of wild-type.

FIG. 10B shows detection of the green fluorescence signal in developing seeds of CON::pPLAIIIδ mutants. Developing seeds from *Arabidopsis* siliques were imaged using a Nikon Eclipse 800 widefield microscope and a X60 differential interference contrast, 1.2-numerical aperture objective, with mercury lamp excitation and a 492/18 BP excitation filter and a 535/40 B emission filter.

FIG. 10C shows the ratio of the level of fatty acids with 20 carbons over 18 carbons in seeds of WT and CON::pPLAIIIδ mutants. Values are means±SE (n=3). $^H$Significantly higher at $P<0.05$ compared with the WT, based on Student's t test.

FIG. 10D shows the ratio of the level of fatty acids of 20:1 over 18:1 in seeds of WT and CON::pPLAIIIδ mutants. Values are means±SE (n=3). $^H$Significantly higher at $P<0.05$ compared with the WT, based on Student's t test.

The level of pPLAIIIδ expression in developing siliques was 25 fold higher in CON::pPLAIIIδ than that in WT (FIG. 9C). The presence of the pPLAIIIδ-GFP protein was detectable by visualizing the GFP fluorescence (FIG. 10B). CON::pPLAIIIδ plant height and seed yield were comparable with WT (FIGS. 9A and 9B). In three CON::pPLAIIIδ lines tested, seed oil content was increased over that in WT seeds (39% vs 35%; FIG. 9D). While oil content per CON::pPLAIIIδ seed weight was lower than that per 35S::pPLAIIIδ seed weight (FIG. 2D vs. 9D), the overall seed oil production per CON::pPLAIIIδ plant was significantly higher than that per 35S::pPLAIIIδ, due to the higher seed yield per plant (FIG. 9B), and per WT plant, due to the increased oil content without change in seed yield (FIGS. 9B and 9D).

The seed specific overexpression of pPLAIIIδ resulted in changes in fatty acid composition, and the changes in CON::pPLAIIIδ were similar to those in 35S::pPLAIIIδ seeds. The percentages of 18:1 and 18:2 were lower, while those of 20:0, 20:1, 20:2, and 22:1 were higher, in CON::pPLAIIIδ lines than WT (FIG. 9E). The ratio of 20:1 to 18:1 was 30% higher in CON::pPLAIIIδ lines than WT (FIG. 10C), and the same pattern was observed when total 20 carbon-fatty acids were compared with total 18-carbon fatty acids (FIG. 10D).

These results indicate that pPLAIIIδ affects TAG metabolism in the same manner regardless of the promoter used, and that the use of seed specific expression of pPLAIIIδ has the potential to be applied for increased seed oil production. While a constitutive promoter can be used to express pPLAIIIδ, use of a seed specific promoter, which produces the same results, but with more seeds, may be preferred for producing more oil/plant.

In conclusion, the data presented above show that pPLAIIIδ hydrolyzes PC to generate FFA and LPC, and genetic alterations of pPLAIIIδ expression change seed oil content and fatty acid composition in *Arabidopsis* seeds. Our large scale of TAG species analysis reveals that pPLAIIIδ promotes the production of 20:1-TAG. We propose that pPLAIIIδ plays a role in fatty acyl flux from the plastid to ER and/or PC fatty acyl remodeling for TAG synthesis. Furthermore, the present results indicate that the use of seed-specific expression of pPLAIIIδ has the potential to improve seed oil production in crops.

The disclosure being thus described, it will be obvious that the same may be varied in many ways. Such variations are not to be regarded as a departure from the spirit and scope of the disclosure, and all such modifications as would be obvious to one skilled in the art are intended to be included within the scope of the following claims.

ACCESSION NUMBERS

Sequence data from this disclosure can be found in the *Arabidopsis* Genome Initiative database under the following accession numbers: AAPT1, At1g13560; AAPT2, At3g25585; CCT1, At2g32260; CCT2, At4g15130; DGAT1, At2g19450; DGAT2, At3g51520; GPAT, At1g32200; LPAT2, At3g57650; LPAT3, At1g51260; LPAT4, At1g75020; LPAT5, At3g18850; LPCAT1, At1g63050; PAH1, At3g09560; PDAT1, At5g13640; pPLAI, At1g61850; pPLAIIα, At2g26560; pPLAIIβ, At4g37050; pPLAIIγ, At4g37070; pPLAIIδ, At4g37060; pPLAIIε, At5g43590; pPLAIIIα, At2g39220; pPLAIIIβ, At3g54950; pPLAIIIγ, At4g29800; pPLAIIIδ, At3g63200; and UBQ10, At4g05320.

LITERATURE CITED

Andersson M X, Kelly A A (2010) Plastid glycerolipid synthesis. Acyl-Lipid Metabolism. The *Arabidopsis* Book 8: e0133

Bafor M, Smith M A, Jonsson L, Stobart K, Stymne S (1991) Ricinoleic acid biosynthesis and triacylglycerol assembly in microsomal preparations from developing castor-bean (*Ricinus communis*) endosperm. Biochem J 280: 507-514

Bassel G W, Fung P, Chow T F, Foong J A, Provart N J, Cutler S R (2008) Elucidating the germination transcriptional program using small molecules. Plant Physiol 147: 143-155

Bates P D, Browse J (2011) The pathway of triacylglycerol synthesis through phosphatidylcholine in *Arabidopsis* produces a bottleneck for the accumulation of unusual fatty acids in transgenic seeds. *Plant J* 68: 387-399

Bates P D, Browse J (2012) *The significance of different diacylglycerol synthesis pathways on plant oil composition and bioengineering*. Front Plant Sci 3: 147

Bates P D, Durrett T P, Ohlrogge J B, Pollard M (2009) Analysis of acyl fluxes through multiple pathways of triacylglycerol synthesis in developing soybean embryos. Plant Physiol 150: 55-72

Bates P D, Fatihi A, Snapp A R, Carlsson A S, Browse J, Lu C (2012) *Acyl editing and headgroup exchange are the major mechanisms that direct polyunsaturated Fatty Acid flux into triacylglycerols*. Plant Physiol 160: 1530-1539

Bates P D, Ohlrogge J B, Pollard M (2007) Incorporation of newly synthesized fatty acids into cytosolic glycerolipids in pea leaves occurs via acyl editing. J Biol Chem 282: 31206-31216

Bourgis F, Kilaru A, Cao X, Ngando-Ebongue G F, Drira N, Ohlrogge J B, Arondel V (2011) *Comparative transcriptome and metabolite analysis of oil palm and date palm mesocarp that differ dramatically in carbon partitioning*. Proc Natl Acad Sci USA 108: 12527-12532

Chapman K D, Ohlrogge J B (2012) Compartmentation of triacylglycerol accumulation in plants. *J Biol Chem* 287: 2288-2294

Dyer J M, Stymne S, Green A G, Carlsson A S (2008) High-value oils from plants, Plant J 54: 640-655

Fan, L., Zheng, S., Cui, D., and Wang, X. (1999). Subcellular distribution and tissue expression of phospholipase Dα, β and γ in *Arabidopsis*. Plant Physiol. 119: 1371-1378.

Han J, Clement J M, Li J, King A, Ng S, Jaworski J G (2010) *The cytochrome P450CYP86A22 is a fatty acyl-CoA omega-hydroxylase essential for estolide synthesis in the stigma of Petunia hybrida*. J Biol Chem 285: 3986-3996

Han X, Gross R W (2001) Quantitative analysis and molecular species fingerprinting of triacylglyceride molecular species directly from lipid extracts of biological samples by electrospray ionization tandem mass spectrometry. Anal Chem 295: 88-100

Harwood J L (1996) *Recent advances in the biosynthesis of plant fatty acids*. Biochim Biophys Acta 1301: 7-56

Hayden D M, Rolletschek H, Borisjuk L, Corwin J, Kliebenstein D J, Grimberg A, Stymne S, Dehesh K (2011) *Cofactome analyses reveal enhanced flux of carbon into oil for potential biofuel production*. Plant J 67: 1018-1028

Huang S, Cerny R E, Bhat D S, Brown S M (2001) Cloning of an *Arabidopsis* patatin-like gene, STURDY, by activation T-DNA tagging. Plant Physiol 125: 573-584

Joubès J, Raffaele S, Bourdenx B, Garcia C, Laroche-Traineau J, Moreau P, Domergue F, Lessire R (2008) The VLCFA elongase gene family in *Arabidopsis thaliana*: phylogenetic analysis, 3D modelling and expression profiling. *Plant Mol Biol* 67: 547-566

La Camera S, Geoffroy P, Samaha H, Ndiaye A, Rahim G, Legrand M, Heitz T (2005) *A pathogen-inducible patatin-like lipid acyl hydrolase facilitates fungal and bacterial host colonization in Arabidopsis*. Plant J 44: 810-825

Lee J, Welti R, Roth M, Schapaugh W T, Li J, Trick H N (2012) Enhanced seed viability and lipid compositional changes during natural ageing by suppressing phospholipase Dα in soybean seed. Plant Biotechnol J 10: 164-173

Lee J, Welti R, Schapaugh W T, Trick H N (2011) *Phospholipid and triacylglycerol profiles modified by PLD suppression in soybean seed*. Plant Biotechnology J 9: 359-372

Li M, Bahn S C, Guo L, Musgrave W, Berg H, Welti R, Wang X (2011) *Patatin-related phospholipase pPLAIIIβ-induced changes in lipid metabolism alter cellulose content and cell elongation in Arabidopsis*. Plant Cell 23: 1107-1123

Li M, Qin C, Welti R, Wang X (2006) Double knockouts of phospholipase Dζ1 and ζ2 in *Arabidopsis* affect root elongation during phosphate-limited growth but do not affect root hair patterning. Plant Physiol 140: 761-770

Li-Beisson Y, Shorrosh B, Beisson F, Andersson M X, Arondel V, Bates P D, Baud S, Bird D, DeBono A, Durrett T P, Franke R B, Graham I A, Katayama K, Kelly A A, Larson T, Markham J E, Miguel M, Molina I, Nishida I, Rowland O, Samuels L, Schmid K M, Wada H, Welti R, Xu C, Zallot R, Ohlrogge J B (2010) Acyl-lipid metabolism. The *Arabidopsis* Book 8: e0133

Loewen C J, Gaspar M L, Jesch S A, Delon C, Ktistakis N T, Henry S A, Levine T P. (2004) Phospholipid metabolism regulated by a transcription factor sensing phosphatidic acid. *Science* 304: 1644-1647.

Lu C, Xin Z, Ren Z, Miguel M, Browse J (2009) An enzyme regulating triacylglycerol composition is encoded by the ROD1 gene of *Arabidopsis*. *Proc Natl Acad Sci USA* 106: 18837-18842

Magnes C, Sinner F M, Regittnig W, Pieber T R (2005) LC/MS/MS method for quantitative determination of long-chain fatty acyl-CoAs. *Anal Chem* 77: 2889-2294

Murakami M, Taketomi Y, Mild Y, Sato H, Hirabayashi T, Yamamoto K (2011) *Recent progress in phospholipase $A_2$ research: from cells to animals to humans*. Prog Lipid Res 50: 152-192

Nishida I, Bates P D (2010) Eukaryotic phospholipid synthesis. Acyl-Lipid Metabolism. The *Arabidopsis* Book 8: e0133

Pappan K, Zheng L, Krishnamoorthi R, Wang X (2004) Evidence for and characterization of $Ca^{2+}$ binding to the catalytic region of *Arabidopsis thaliana* phospholipase Dβ. J Biol Chem 279: 47833-47839

Pidkowich M S, Nguyen H T, Heilmann I, Ischebeck T, Shanklin J (2007) Modulating seed beta-ketoacyl-acyl carrier protein synthase II level converts the composition of a temperate seed oil to that of a palm-like tropical oil. Proc Natl Acad Sci USA 104: 4742-4747

Rietz S, Dermendjiev G, Oppermann E, Tafesse F G, Effendi Y, Holk A, Parker J E, Teige M, Scherer G F (2010) *Roles of Arabidopsis patatin-related phospholipases a in root development are related to auxin responses and phosphate deficiency*. Mol Plant 3: 524-538

Rietz S, Holk A, Scherer G F (2004) *Expression of the patatin-related phospholipase A gene AtPLA IIA in Arabidopsis thaliana is up-regulated by salicylic acid, wounding, ethylene, and iron and phosphate deficiency*. Planta 219: 743-753

Rogalski M, Carrer H (2011) *Engineering plastid fatty acid biosynthesis to improve food quality and biofuel production in higher plants*. Plant Biotechnol J 9: 554-564

Rowland O, Bird D (2010) Cuticular waxes. Acyl-Lipid Metabolism. The *Arabidopsis* Book 8: e0133

Scherer G F, Ryu S B, Wang X, Matos A R, Heitz T (2010) *Patatin-related phospholipase A: nomenclature, subfamilies and functions in plants*. Trends Plant Sci 15: 693-700

Stewart C N Jr, Via L E (1993) A rapid CTAB DNA isolation technique useful for RAPD fingerprinting and other PCR applications. Biotechniques 14: 748-758

Stymne S, Stobart A K (1984) Evidence for the reversibility of the acyl-coA-lysophosphatidylcholine acyltransferase in microsomal preparations from developing safflower (*Carthamus tinctorius* L) cotyledons and rat-liver. Biochem J 223: 305-314

Tamura K, Peterson D, Peterson N, Stecher G, Nei M, Kumar S (2011) MEGA5: Molecular evolutionary genetics analysis using maximum likelihood, evolutionary distance, and maximum parsimony methods. Mol Biol Evol 28: 2731-2739

Tjellström H, Yang Z, Allen D K, Ohlrogge J B (2012) *Rapid kinetic labeling of Arabidopsis cell suspension cultures: implications for models of lipid export from plastids*. Plant Physiol 158: 601-611

Wang L, Shen W, Kazachkov M, Chen G, Chen Q, Carlsson A S, Stymne S, Weselake R J, Zou J (2012) *Metabolic interactions between the lands cycle and the kennedy pathway of glycerolipid synthesis in Arabidopsis developing seeds*. Plant Cell 24: 4652-4669

Wang Z, Benning C (2012) *Chloroplast lipid synthesis and lipid trafficking through ER-plastid membrane contact sites*. Biochem Soc Trans 40: 457-463

Wang Z, Xu C, Benning C (2012) *TGD4 involved in endoplasmic reticulum-to-chloroplast lipid trafficking is a phosphatidic acid binding protein*. Plant J 70: 614-623

Welti R, Li W, Li M, Sang Y, Biesiada H, Zhou H E, Rajashekar C B, Williams T D, Wang X (2002) Profiling membrane lipids in plant stress responses. Role of phospholipase Dα in freezing-induced lipid changes in *Arabidopsis*. J Biol Chem 277: 31994-32002

Weselake R J, Taylor D C, Rahman M H, Shah S, Laroche A, McVetty P B, Harwood J L (2009) Increasing the flow of carbon into seed oil. Biotechnol Adv 27: 866-878

Winter D, Vinegar B, Nahal H, Ammar R, Wilson G V, Provart N J (2007) An 'electronic fluorescent pictograph' browser for exploring and analyzing large-scale biological data sets. PLoS One 2: e718

Xiao S, Gao W, Chen Q F, Chan S W, Zheng S X, Ma J, Wang M, Welti R, Chye M L (2010) Overexpression of *Arabidopsis* acyl-CoA binding protein ACBP3 promotes starvation-induced and age-dependent leaf senescence. Plant Cell 22: 1463-1482

Yang W, Devaiah S P, Pan X, Isaac G, Welti R, Wang X (2007) AtPLAI is an acyl hydrolase involved in basal jasmonic acid production and *Arabidopsis* resistance to *Botrytis cinerea*. J Biol Chem 282: 18116-18128

Yang W, Zheng Y, Bahn S C, Pan X, Li M, Vu H, Roth M, Scheu B, Welti R, Hong Y, Wang X (2012) *The patatin-containing phospholipase A pPLAIIα modulates oxylipin formation and water loss in Arabidopsis thaliana*. Mol Plant 5: 452-460

---

What is claimed is:

1. A method selected from the group consisting of:
    (i) producing an enhanced amount of oil in seeds of an oilseed plant compared to the amount of oil produced in seeds by an otherwise identical control oilseed plant grown under the same conditions;
    (ii) producing oil in seeds of an oilseed plant containing an enhanced amount of C20 and C22 fatty acids compared to the amount of C20 and C22 fatty acids in oil produced in seeds by an otherwise identical control oilseed plant grown under the same conditions;
    (iii) producing oil in seeds of an oilseed plant containing an enhanced amount of C56, C58, and C60 triacylglycerols compared to the amount of C56, C58, and C60 triacylglycerols in oil produced in seeds by an otherwise identical control oilseed plant grown under the same conditions;
    (iv) producing an enhanced amount of oil in seeds of an oilseed plant containing an enhanced amount of C20 and C22 fatty acids compared to the amount of oil and C20 and C22 fatty acids produced in seeds by an otherwise identical control oilseed plant grown under the same conditions;
    (v) producing an enhanced amount of oil in seeds of an oilseed plant containing an enhanced amount of C56, C58, and C60 triacylglycerols compared to the amount of oil and C56, C58, and C60 triacylglycerols produced in seeds by an otherwise identical control oilseed plant grown under the same conditions;
    (vi) producing an enhanced amount of oil in seeds of an oilseed plant containing an enhanced amount of C20 and C22 fatty acids and an enhanced amount of C56, C58, and C60 triacylglycerols compared to the amount of oil, C20 and C22 fatty acids, and C56, C58, and C60 triacylglycerols, respectively, produced in seeds by an otherwise identical control oilseed plant grown under the same conditions; and
    (vii) producing enhanced levels of mRNA transcripts for one or more genes selected from the group consisting of glycerol-3-phosphate acyltransferase (GPAT), lysophosphatidic acid acyltransferase (LPAT), phosphatidic acid phosphohydrolase (PAH), and diacylglycerol acyltransferase (DGAT) in seeds of an oilseed plant compared to the levels of mRNA transcripts for said genes produced in seeds by an otherwise identical control oilseed plant grown under the same conditions,
    wherein said oilseed plant is a plant other than *Arabidopsis*,
    wherein said method comprises expressing a pPLAIIIδ protein from a heterologous nucleotide sequence in the genome of the plant, the pPLAIIIδ protein having at least 95% sequence similarity to an *Arabidopsis* pPLAIIIδ protein of SEQ ID NO: 57, and
    wherein said pPLAIIIδ protein exhibits enzymatic activity in the range of from about 75% to about 125% or more of the enzymatic activity of said *Arabidopsis* pPLAIIIδ protein of SEQ ID NO 57.

2. The method of claim 1, wherein said heterologous nucleotide sequence that encodes said pPLAIIIδ protein is expressed under the control of a seed-specific promoter.

3. The method of claim 1, wherein said oilseed plant is selected from the group consisting of plants of the genera *Brassica* (e.g., rapeseed/canola (*Brassica napus*; *Brassica carinata*; *Brassica nigra*; *Brassica oleracea*), *Camelina*, *Miscanthus*, and *Jatropha*; Jojoba (*Simmondsia chinensis*), coconut; cotton; peanut; rice; safflower; sesame; soybean; mustard other than *Arabidopsis*; wheat; flax (linseed); sunflower; olive; corn; palm; palm kernel; sugarcane; castor bean; switchgrass; *Borago officinalis*; *Echium plantagineum*; *Cuphea hookeriana*; *Cuphea pulcherrima*; *Cuphea lanceolata*; *Ricinus communis*; *Coriandrum sativum*; *Crepis alpina*; *Vernonia galamensis*; *Momordica charantia*; and *Crambe abyssinica*.

4. The method of claim 1, wherein said enhanced amount of oil is about 5% higher than that compared to the amount of oil in seeds of an otherwise identical control oilseed plant grown under the same conditions.

5. The method of claim 1, wherein said C20 fatty acids comprise C20:0, C20:1, C20:2, and said C22 fatty acid is C22:1.

6. The method of claim 1, wherein said enhanced amount of said C20 and C22 fatty acids in said oil is increased by about 10% to about 20% compared to the amount of said fatty acids in seed oil produced by an otherwise identical control oilseed plant grown under the same conditions.

7. The method of claim 1, wherein said enhanced amount of C56, C58, and C60 triacylglycerols is about 10% to about 20% higher than that compared to the amount of C56, C58, and C60 triacylglycerols produced by an otherwise identical control oilseed plant grown under the same conditions.

8. The method of claim 1, wherein said enhanced amount of oil is about 5% higher, and said enhanced amount of C20 and C22 fatty acids is about 10% to about 20% higher, than that compared to the amount of oil or C20 and C22 fatty acids, respectively, produced by an otherwise identical control oilseed plant grown under the same conditions.

9. The method of claim 1, wherein said enhanced amount of oil is about 5% higher, and said enhanced amount of C56, C58, and C60 triacylglycerols is about 10% to about 20% higher, than that compared to the amount of oil or C56, C58, and C60 triacylglycerols, respectively, produced by an otherwise identical control oilseed plant grown under the same conditions.

* * * * *

SEQUENCE LISTING

<160> NUMBER OF SEQ ID NOS: 58

<210> SEQ ID NO 1
<211> LENGTH: 21
<212> TYPE: DNA
<213> ORGANISM: Artificial Sequence
<220> FEATURE:
<223> OTHER INFORMATION: Forward primer for screening for T-DNA
      insertional mutant of Salk_040363

<400> SEQUENCE: 1
ccgagcatcg agactgataa g                                        21

<210> SEQ ID NO 2
<211> LENGTH: 21
<212> TYPE: DNA
<213> ORGANISM: Artificial Sequence
<220> FEATURE:
<223> OTHER INFORMATION: Reverse primer for screening for T-DNA
      insertional mutant of Salk_040363

<400> SEQUENCE: 2
agtatcagct gctccatcag c                                            21

<210> SEQ ID NO 3
<211> LENGTH: 22
<212> TYPE: DNA
<213> ORGANISM: Artificial Sequence
<220> FEATURE:
<223> OTHER INFORMATION: T-DNA LB primer for screening of T-DNA
      insertional mutant of Salk_040363

<400> SEQUENCE: 3
gcgtggaccg cttgctgcaa ct                                           22

<210> SEQ ID NO 4
<211> LENGTH: 22
<212> TYPE: DNA
<213> ORGANISM: Artificial Sequence
<220> FEATURE:
<223> OTHER INFORMATION: Forward primer for screening for T-DNA
      insertional mutant of Salk_057212

<400> SEQUENCE: 4
ttgacggata tgcaggaacc aa                                           22

<210> SEQ ID NO 5
<211> LENGTH: 21
<212> TYPE: DNA
<213> ORGANISM: Artificial Sequence
<220> FEATURE:
<223> OTHER INFORMATION: Reverse primer for screening for T-DNA
      insertional mutant of Salk_057212

<400> SEQUENCE: 5
atgcgtgatt gcagccgctg t                                            21

<210> SEQ ID NO 6
<211> LENGTH: 22
<212> TYPE: DNA
<213> ORGANISM: Artificial Sequence
<220> FEATURE:
<223> OTHER INFORMATION: T-DNA LB primer for screening for T-DNA
      insertional mutant of Salk_057212

<400> SEQUENCE: 6
gcgtggaccg cttgctgcaa ct                                           22

<210> SEQ ID NO 7
<211> LENGTH: 22
<212> TYPE: DNA
<213> ORGANISM: Artificial Sequence
<220> FEATURE:
<223> OTHER INFORMATION: Forward primer for screening for T-DNA
      insertional mutant of Salk_088404

<400> SEQUENCE: 7
gaaagcttcc acaatctaac tg                                           22

<210> SEQ ID NO 8
<211> LENGTH: 21
<212> TYPE: DNA
<213> ORGANISM: Artificial Sequence
<220> FEATURE:
<223> OTHER INFORMATION: Reverse primer for screening for T-DNA
      insertional mutant of Salk_088404

<400> SEQUENCE: 8
ggcgattcga gcgtttggat c                                            21

<210> SEQ ID NO 9
<211> LENGTH: 22
<212> TYPE: DNA
<213> ORGANISM: Artificial Sequence
<220> FEATURE:
<223> OTHER INFORMATION: T-DNA LB primer for screening for T-DNA
      insertional mutant of Salk_088404

<400> SEQUENCE: 9
gcgtggaccg cttgctgcaa ct                                             22

<210> SEQ ID NO 10
<211> LENGTH: 22
<212> TYPE: DNA
<213> ORGANISM: Artificial Sequence
<220> FEATURE:
<223> OTHER INFORMATION: Forward primer for screening for T-DNA
      insertional mutant of Salk_029470

<400> SEQUENCE: 10
tcgcagtgag agagccattt ct                                             22

<210> SEQ ID NO 11
<211> LENGTH: 27
<212> TYPE: DNA
<213> ORGANISM: Artificial Sequence
<220> FEATURE:
<223> OTHER INFORMATION: Reverse primer for screening for T-DNA
      insertional mutant of Salk_029470

<400> SEQUENCE: 11
caagcaacaa atattagctg cccaaac                                        27

<210> SEQ ID NO 12
<211> LENGTH: 22
<212> TYPE: DNA
<213> ORGANISM: Artificial Sequence
<220> FEATURE:
<223> OTHER INFORMATION: T-DNA LB primer for screening for T-DNA
      insertional mutant of Salk_029470

<400> SEQUENCE: 12
gcgtggaccg cttgctgcaa ct                                             22

<210> SEQ ID NO 13
<211> LENGTH: 26
<212> TYPE: DNA
<213> ORGANISM: Artificial Sequence
<220> FEATURE:
<223> OTHER INFORMATION: Promoter region primer for cloning of
      pPLAIIIdelta gene into pEC291 vector

<400> SEQUENCE: 13
aggcgcgcca aactatctcg tgtcgc                                         26

<210> SEQ ID NO 14
<211> LENGTH: 26
<212> TYPE: DNA
<213> ORGANISM: Artificial Sequence
<220> FEATURE:
<223> OTHER INFORMATION: Terminator region primer for cloning of
      pPLAIIIdelta gene into pEC291 vector

<400> SEQUENCE: 14
aggcgcgcca ctctgtgctg gctatc                                         26

<210> SEQ ID NO 15
<211> LENGTH: 34
<212> TYPE: DNA
<213> ORGANISM: Artificial Sequence
<220> FEATURE:
<223> OTHER INFORMATION: Forward primer for cloning of pPLAIIIdelta
      gene into pMDC83 vector

<400> SEQUENCE: 15
atttaattaa atggagatgg atctcagcaa ggtt                              34

<210> SEQ ID NO 16
<211> LENGTH: 34
<212> TYPE: DNA
<213> ORGANISM: Artificial Sequence
<220> FEATURE:
<223> OTHER INFORMATION: Reverse primer for cloning of pPLAIIIdelta
      gene into pMDC83 vector

<400> SEQUENCE: 16
atggcgcgcc aacggccgtc agcgagaggg ttaa                              34

<210> SEQ ID NO 17
<211> LENGTH: 33
<212> TYPE: DNA
<213> ORGANISM: Artificial Sequence
<220> FEATURE:
<223> OTHER INFORMATION: Forward primer for cloning of pPLAIIIdelta
      cDNA into pET28a vector

<400> SEQUENCE: 17
tttggatcca tggagatgga tctcagcaag gtt                               33

<210> SEQ ID NO 18
<211> LENGTH: 29
<212> TYPE: DNA
<213> ORGANISM: Artificial Sequence
<220> FEATURE:
<223> OTHER INFORMATION: Reverse primer for cloning of pPLAIIIdelta
      cDNA into pET28a vector

<400> SEQUENCE: 18
aaggcggccg cacggccgtc agcgagagg                                    29

<210> SEQ ID NO 19
<211> LENGTH: 34
<212> TYPE: DNA
<213> ORGANISM: Artificial Sequence
<220> FEATURE:
<223> OTHER INFORMATION: Forward primer for cloning of Beta-conglycinin
      promoter into pZY101 vector

<400> SEQUENCE: 19
atgtttaaac aagcttttga tccatgccct tcat                              34

<210> SEQ ID NO 20
<211> LENGTH: 35
<212> TYPE: DNA
<213> ORGANISM: Artificial Sequence
<220> FEATURE:
<223> OTHER INFORMATION: Reverse primer for cloning of Beta-conglycinin
      promoter into pZY101 vector

<400> SEQUENCE: 20
atttaattaa gcggccgcag tatatcttaa attct                             35

```
<210> SEQ ID NO 21
<211> LENGTH: 20
<212> TYPE: DNA
<213> ORGANISM: Artificial Sequence
<220> FEATURE:
<223> OTHER INFORMATION: Real time PCR Primer

<400> SEQUENCE: 21
gcccttggaa tctactgctt                                              20

<210> SEQ ID NO 22
<211> LENGTH: 20
<212> TYPE: DNA
<213> ORGANISM: Artificial Sequence
<220> FEATURE:
<223> OTHER INFORMATION: Real time PCR Primer

<400> SEQUENCE: 22
acataacttc acctatcctg                                              20

<210> SEQ ID NO 23
<211> LENGTH: 20
<212> TYPE: DNA
<213> ORGANISM: Artificial Sequence
<220> FEATURE:
<223> OTHER INFORMATION: Real time PCR Primer

<400> SEQUENCE: 23
cgaaccaaaa ggattgaaaa                                              20

<210> SEQ ID NO 24
<211> LENGTH: 20
<212> TYPE: DNA
<213> ORGANISM: Artificial Sequence
<220> FEATURE:
<223> OTHER INFORMATION: Real time PCR Primer

<400> SEQUENCE: 24
tccacaagag gaaccccgtc                                              20

<210> SEQ ID NO 25
<211> LENGTH: 20
<212> TYPE: DNA
<213> ORGANISM: Artificial Sequence
<220> FEATURE:
<223> OTHER INFORMATION: Real time PCR Primer

<400> SEQUENCE: 25
gccacttcta ctaaactccc                                              20

<210> SEQ ID NO 26
<211> LENGTH: 20
<212> TYPE: DNA
<213> ORGANISM: Artificial Sequence
<220> FEATURE:
<223> OTHER INFORMATION: Real time PCR Primer

<400> SEQUENCE: 26
cacacacaaa caaacacatc                                              20

<210> SEQ ID NO 27
<211> LENGTH: 20
<212> TYPE: DNA
<213> ORGANISM: Artificial Sequence
<220> FEATURE:
<223> OTHER INFORMATION: Real time PCR Primer
```

<400> SEQUENCE: 27
ctgacgattt ccaaagacaa					20

<210> SEQ ID NO 28
<211> LENGTH: 20
<212> TYPE: DNA
<213> ORGANISM: Artificial Sequence
<220> FEATURE:
<223> OTHER INFORMATION: Real time PCR Primer

<400> SEQUENCE: 28
ttcaatccct tgttgctca					20

<210> SEQ ID NO 29
<211> LENGTH: 23
<212> TYPE: DNA
<213> ORGANISM: Artificial Sequence
<220> FEATURE:
<223> OTHER INFORMATION: Real time PCR Primer

<400> SEQUENCE: 29
ggttcatctt ctgcattttc gga				23

<210> SEQ ID NO 30
<211> LENGTH: 23
<212> TYPE: DNA
<213> ORGANISM: Artificial Sequence
<220> FEATURE:
<223> OTHER INFORMATION: Real time PCR Primer

<400> SEQUENCE: 30
ttttcggttc atcaggtcgt ggt				23

<210> SEQ ID NO 31
<211> LENGTH: 23
<212> TYPE: DNA
<213> ORGANISM: Artificial Sequence
<220> FEATURE:
<223> OTHER INFORMATION: Real time PCR Primer

<400> SEQUENCE: 31
tgtttgagag gcacaagtcc cga				23

<210> SEQ ID NO 32
<211> LENGTH: 23
<212> TYPE: DNA
<213> ORGANISM: Artificial Sequence
<220> FEATURE:
<223> OTHER INFORMATION: Real time PCR Primer

<400> SEQUENCE: 32
agtccaaatc cagctccaag gta				23

<210> SEQ ID NO 33
<211> LENGTH: 23
<212> TYPE: DNA
<213> ORGANISM: Artificial Sequence
<220> FEATURE:
<223> OTHER INFORMATION: Real time PCR Primer

<400> SEQUENCE: 33
caagtcggtg aatgaacaat acg				23

<210> SEQ ID NO 34
<211> LENGTH: 23

<212> TYPE: DNA
<213> ORGANISM: Artificial Sequence
<220> FEATURE:
<223> OTHER INFORMATION: Real time PCR Primer

<400> SEQUENCE: 34
tgattgtgtt tgtgtatccc taa                                          23

<210> SEQ ID NO 35
<211> LENGTH: 23
<212> TYPE: DNA
<213> ORGANISM: Artificial Sequence
<220> FEATURE:
<223> OTHER INFORMATION: Real time PCR Primer

<400> SEQUENCE: 35
caagaacaga acattggccg tcc                                          23

<210> SEQ ID NO 36
<211> LENGTH: 23
<212> TYPE: DNA
<213> ORGANISM: Artificial Sequence
<220> FEATURE:
<223> OTHER INFORMATION: Real time PCR Primer

<400> SEQUENCE: 36
gcccagtgta ggaactttat tgc                                          23

<210> SEQ ID NO 37
<211> LENGTH: 23
<212> TYPE: DNA
<213> ORGANISM: Artificial Sequence
<220> FEATURE:
<223> OTHER INFORMATION: Real time PCR Primer

<400> SEQUENCE: 37
atttatcacc aaggatgctc aac                                          23

<210> SEQ ID NO 38
<211> LENGTH: 23
<212> TYPE: DNA
<213> ORGANISM: Artificial Sequence
<220> FEATURE:
<223> OTHER INFORMATION: Real time PCR Primer

<400> SEQUENCE: 38
tgaaaccacc gaatacaagg aaa                                          23

<210> SEQ ID NO 39
<211> LENGTH: 23
<212> TYPE: DNA
<213> ORGANISM: Artificial Sequence
<220> FEATURE:
<223> OTHER INFORMATION: Real time PCR Primer

<400> SEQUENCE: 39
cgttcggcga gttctactaa agg                                          23

<210> SEQ ID NO 40
<211> LENGTH: 23
<212> TYPE: DNA
<213> ORGANISM: Artificial Sequence
<220> FEATURE:
<223> OTHER INFORMATION: Real time PCR Primer

<400> SEQUENCE: 40

```
tcttcttctg gtctttgatt ggg                                              23

<210> SEQ ID NO 41
<211> LENGTH: 23
<212> TYPE: DNA
<213> ORGANISM: Artificial Sequence
<220> FEATURE:
<223> OTHER INFORMATION: Real time PCR Primer

<400> SEQUENCE: 41
gattgccttc accaccatct gta                                              23

<210> SEQ ID NO 42
<211> LENGTH: 23
<212> TYPE: DNA
<213> ORGANISM: Artificial Sequence
<220> FEATURE:
<223> OTHER INFORMATION: Real time PCR Primer

<400> SEQUENCE: 42
agcagaggtc aagtagacac agg                                              23

<210> SEQ ID NO 43
<211> LENGTH: 23
<212> TYPE: DNA
<213> ORGANISM: Artificial Sequence
<220> FEATURE:
<223> OTHER INFORMATION: Real time PCR Primer

<400> SEQUENCE: 43
tgcggttcag attccgcttt tct                                              23

<210> SEQ ID NO 44
<211> LENGTH: 24
<212> TYPE: DNA
<213> ORGANISM: Artificial Sequence
<220> FEATURE:
<223> OTHER INFORMATION: Real time PCR Primer

<400> SEQUENCE: 44
gttgccaccg gtaaatagct ttcg                                             24

<210> SEQ ID NO 45
<211> LENGTH: 22
<212> TYPE: DNA
<213> ORGANISM: Artificial Sequence
<220> FEATURE:
<223> OTHER INFORMATION: Real time PCR Primer

<400> SEQUENCE: 45
acccgttcta tgccggattt gg                                               22

<210> SEQ ID NO 46
<211> LENGTH: 23
<212> TYPE: DNA
<213> ORGANISM: Artificial Sequence
<220> FEATURE:
<223> OTHER INFORMATION: Real time PCR Primer

<400> SEQUENCE: 46
tcctgttgcc acttctccct ttg                                              23

<210> SEQ ID NO 47
<211> LENGTH: 23
<212> TYPE: DNA
<213> ORGANISM: Artificial Sequence
```

<220> FEATURE:
<223> OTHER INFORMATION: Real time PCR Primer

<400> SEQUENCE: 47
ggagtgggga taccaacgga acg                                              23

<210> SEQ ID NO 48
<211> LENGTH: 23
<212> TYPE: DNA
<213> ORGANISM: Artificial Sequence
<220> FEATURE:
<223> OTHER INFORMATION: Real time PCR Primer

<400> SEQUENCE: 48 gaaagggat gcaactgtcg gga                                               23

<210> SEQ ID NO 49
<211> LENGTH: 26
<212> TYPE: DNA
<213> ORGANISM: Artificial Sequence
<220> FEATURE:
<223> OTHER INFORMATION: Real time PCR Primer

<400> SEQUENCE: 49
gtagcagagg agatgctgaa gcagaa                                           26

<210> SEQ ID NO 50
<211> LENGTH: 26
<212> TYPE: DNA
<213> ORGANISM: Artificial Sequence
<220> FEATURE:
<223> OTHER INFORMATION: Real time PCR Primer

<400> SEQUENCE: 50
tacagtggga gcgattctac aactcc                                           26

<210> SEQ ID NO 51
<211> LENGTH: 26
<212> TYPE: DNA
<213> ORGANISM: Artificial Sequence
<220> FEATURE:
<223> OTHER INFORMATION: Real time PCR Primer

<400> SEQUENCE: 51
cacggatcca agagcagaga atgtga                                           26

<210> SEQ ID NO 52
<211> LENGTH: 26
<212> TYPE: DNA
<213> ORGANISM: Artificial Sequence
<220> FEATURE:
<223> OTHER INFORMATION: Real time PCR Primer

<400> SEQUENCE: 52
ctaacacttc gtcgctgctg ctcaat                                           26

<210> SEQ ID NO 53
<211> LENGTH: 26
<212> TYPE: DNA
<213> ORGANISM: Artificial Sequence
<220> FEATURE:
<223> OTHER INFORMATION: Real time PCR Primer

<400> SEQUENCE: 53
caacgtcttg ttgcgtcagg aaagtc                                           26

<210> SEQ ID NO 54
<211> LENGTH: 24
<212> TYPE: DNA
<213> ORGANISM: Artificial Sequence
<220> FEATURE:
<223> OTHER INFORMATION: Real time PCR Primer

<400> SEQUENCE: 54
attaactcga agatgctggc tggg                                          24

<210> SEQ ID NO 55
<211> LENGTH: 22
<212> TYPE: DNA
<213> ORGANISM: Artificial Sequence
<220> FEATURE:
<223> OTHER INFORMATION: Real time PCR Primer

<400> SEQUENCE: 55
cacactccac ttggtcttgc gt                                            22

<210> SEQ ID NO 56
<211> LENGTH: 24
<212> TYPE: DNA
<213> ORGANISM: Artificial Sequence
<220> FEATURE:
<223> OTHER INFORMATION: Real time PCR Primer

<400> SEQUENCE: 56
tggtctttcc ggtgagagtc ttca                                          24

<210> SEQ ID NO 57
<211> LENGTH: 384
<212> TYPE: PRT
<213> ORGANISM: Arabidopsis thaliana

<400> SEQUENCE: 57

Met Glu Met Asp Leu Ser Lys Val Thr Leu Asp Ile Phe Thr Lys Leu
1               5                   10                  15

Glu Gln Lys Trp Leu Ser His Cys Asp Ser Ser Arg Lys Thr Arg Ile
            20                  25                  30

Leu Ser Ile Asp Gly Gly Gly Thr Gly Ile Val Ala Ala Ala Ser
        35                  40                  45

Ile Leu His Leu Glu His Gln Ile Arg Leu Gln Thr Gly Asp Pro His
    50                  55                  60

Ala His Ile Ser Asp Phe Phe Asp Ile Val Ala Gly Thr Gly Ile Gly
65                  70                  75                  80

Gly Ile Leu Ala Ala Leu Leu Val Ala Asp Asp Gly Ser Gly Arg Pro
                85                  90                  95

Met Phe Thr Ala Arg Asp Ala Val Lys Phe Val Ala Glu Lys Asn Ser
            100                 105                 110

Glu Leu Phe Glu Ile Arg Tyr Thr Gly Val Phe Arg Arg Asn Lys Arg
        115                 120                 125

Tyr Ser Gly Lys Ser Met Glu Arg Val Leu Glu Thr Ala Phe Arg Arg
    130                 135                 140

Glu Asp Gly Lys Val Leu Thr Met Lys Asp Thr Cys Lys Pro Leu Leu
145                 150                 155                 160

Val Pro Cys Tyr Asp Leu Lys Thr Ser Ala Pro Phe Val Phe Ser Arg
                165                 170                 175

Ala Gly Ala Ser Glu Ser Pro Ser Phe Asp Phe Glu Leu Trp Lys Val
            180                 185                 190

```
Cys Arg Ala Thr Ser Ala Thr Pro Ser Leu Phe Lys Pro Phe Ser Val
            195                 200                 205

Val Ser Val Asp Gly Lys Thr Ser Cys Ser Ala Val Asp Gly Gly Leu
210                 215                 220

Val Met Asn Asn Pro Thr Ala Ala Val Thr His Val Leu His Asn
225                 230                 235                 240

Lys Arg Asp Phe Pro Ser Val Asn Gly Val Asp Leu Leu Val Leu
            245                 250                 255

Ser Leu Gly Asn Gly Pro Ser Thr Met Ser Ser Ser Pro Gly Arg Lys
            260                 265                 270

Leu Arg Arg Asn Gly Asp Tyr Ser Thr Ser Ser Val Val Asp Ile Val
            275                 280                 285

Val Asp Gly Val Ser Asp Thr Val Asp Gln Met Leu Gly Asn Ala Phe
290                 295                 300

Cys Trp Asn Arg Thr Asp Tyr Val Arg Ile Gln Ala Asn Gly Leu Thr
305                 310                 315                 320

Ser Gly Gly Ala Glu Glu Leu Leu Lys Glu Arg Gly Val Glu Thr Ala
                325                 330                 335

Pro Phe Gly Val Lys Arg Ile Leu Thr Glu Ser Asn Gly Glu Arg Ile
            340                 345                 350

Glu Gly Phe Val Gln Arg Leu Val Ala Ser Gly Lys Ser Ser Leu Pro
            355                 360                 365

Pro Ser Pro Cys Lys Glu Ser Ala Val Asn Pro Leu Ala Asp Gly Arg
            370                 375                 380

<210> SEQ ID NO 58
<211> LENGTH: 1663
<212> TYPE: DNA
<213> ORGANISM: Arabidopsis thaliana

<400> SEQUENCE: 58
gaatcactca taaacccttt cttcttcctt gttcaaatcc actcactctt ggagagagac      60
gactcaaacg catagtctct cctctgtatt tactcgttat cgtcactgtg agagagagag     120
agagagcgcg cgcattcccc caattaaagc ctctctgctc caaaccgtga tatactcttt     180
acgttgtttg tttttgcctt tatccttccc tagttgtgta taattttgtt cttttcttat     240
ggagatggat ctcagcaagg ttactcttga cattttcaca aagcttgaac agaaatggct     300
ctctcactgc gactcctccc ggaagactcg tatccttagc atcgacggtg cggtaccac      360 tggcattgtc gccgctgctt ctattctcca cctcgagcac cagatccgcc ttcaaaccgg     420
cgaccctcac gctcacatct ctgatttctt cgacattgtc gccggaactg catcggagg      480 cattctcgcc gccctccttg tcgccgacga cggctccggc aggccgatgt tcactgccag     540
agacgcggtt aagtttgtcg cggagaagaa ctcggagctc ttcgagatca ggtacaccgg     600
agttttcagg aggaacaaga gatactcggg gaagagcatg gagagggttt ggagacggc      660 gtttaggaga gaggacggta aggtgttgac gatgaaggac acgtgtaagc ctctccttgt     720
tccttgctac gacctcaaaa cctctgctcc tttcgttttc tcacgcgccg gcgcgtctga     780
gtctccgagc ttcgacttcg agctgtggaa agtctgccgt gccacgtcag caacaccaag     840
cctcttcaag ccgttcagtg tagtgtcggt ggacgggaaa acctcatgct cagccgtaga     900
cggcggtttg gtgatgaaca atccaacagc agctgccgtc acgcacgtgc tacacaacaa     960
acgagatttc ccgtcagtaa acggcgtaga tgacttgctt gtactgtcgt tgggaaacgg    1020
```

-continued

```
tccgtcgacc atgtcatcat caccagggag gaaactccgt cgtaacggag actattcaac     1080
gtcaagtgtg gtggacatag tggttgacgg cgtttccgat accgtcgatc agatgctggg     1140
gaacgctttc tgctggaacc gtactgatta cgttagaatc caggtacgta ttctcaactt     1200
ttctcgtcac cacagagatc accgatcaaa atgtctcgaa tatattaaaa tgtggtggat     1260
gcatgcaggc gaacggtttg acgagcggcg gagcggagga gttgctgaaa gagagaggtg     1320
tggaaacggc gccgtttggg gtaaaacgga tactaacgga gagtaacgga gaaagaatag     1380
agggtttcgt gcaacgtctt gttgcgtcag gaaagtcaag tctacctcca agtccttgca     1440
aggaatctgc cgttaaccct ctcgctgacg gccgttaagt ttcctttatt attataaccc     1500
tccccgtccg tgatgtaaga agtttgtaac caaacccctg ggttaatttt ttaaccccag     1560
ccagcatctt cgagttaatt aattagcctt tcttttttttc taatgactttt agttgaggaa    1620 ttaataatgg ttaatgaatg atagtcttta cttatttatc act                       1663
```